US011873510B2

(12) United States Patent
Prabhakar

(10) Patent No.: US 11,873,510 B2
(45) Date of Patent: *Jan. 16, 2024

(54) T-REG CELL EXPANSION

(71) Applicant: The Board of Trustees of the University of Illinois, Urbana, IL (US)

(72) Inventor: Bellur Prabhakar, Oak Brook, IL (US)

(73) Assignee: BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 304 days.

This patent is subject to a terminal disclaimer.

(21) Appl. No.: 16/879,923

(22) Filed: May 21, 2020

(65) Prior Publication Data

US 2020/0354678 A1    Nov. 12, 2020

Related U.S. Application Data

(63) Continuation of application No. 15/803,232, filed on Nov. 3, 2017, now Pat. No. 10,696,946, which is a continuation-in-part of application No. 14/186,766, filed on Feb. 21, 2014, now abandoned.

(60) Provisional application No. 61/768,204, filed on Feb. 22, 2013.

(51) Int. Cl.
  *C12N 5/0783*  (2010.01)
  *A61P 37/02*   (2006.01)
  *A61K 35/17*   (2015.01)
  *A61K 35/28*   (2015.01)

(52) U.S. Cl.
  CPC ............ *C12N 5/0637* (2013.01); *A61K 35/17* (2013.01); *A61K 35/28* (2013.01); *A61P 37/02* (2018.01); *C12N 2501/22* (2013.01); *C12N 2501/415* (2013.01); *C12N 2501/998* (2013.01); *C12N 2501/999* (2013.01); *C12N 2502/08* (2013.01); *C12N 2502/1121* (2013.01)

(58) Field of Classification Search
  None
  See application file for complete search history.

(56) References Cited

U.S. PATENT DOCUMENTS

| | | | |
|---|---|---|---|
| 6,379,906 B1 | 4/2002 | Tsang et al. | |
| 6,716,974 B1* | 4/2004 | Maciag | C12N 15/1138 435/254.2 |
| 2006/0128619 A1 | 6/2006 | Champion et al. | |
| 2006/0217531 A1 | 9/2006 | Godfrey | |
| 2010/0028995 A1 | 2/2010 | Graversen | |
| 2010/0303811 A1 | 12/2010 | Ochi | |
| 2014/0294792 A1* | 10/2014 | Prabhakar | C12N 5/0637 435/375 |

FOREIGN PATENT DOCUMENTS

| | | |
|---|---|---|
| EP | 1153131 | 11/2001 |
| WO | WO 03082919 A2 | 10/2003 |
| WO | WO2004073732 | 9/2004 |
| WO | WO2014121099 | 8/2014 |

OTHER PUBLICATIONS

Marek-Trzonkowska et al., "Clinical application of regulatory T cells in type 1 diabetes", Pediatr Diabetes, 14(5):322-32 (2013).
D. Lundsgaard, et al., "In Vivo Control of Diabetogenic T-Cells by Regulatory CD4+CD25+ T-Cells Expressing Foxp3", Diabetes, 54 (2005).
C. Mottet, et al., "Cutting Edge" Cure of Colitis by CD4+CD25+ Regulatory T Cells, J Immunol, 170 (2003).
A.P. Kohm, et al., "Cutting Edge: CD4+CD25+ Regulatory T Cells Suppress Antigen-Specific Nervous System Inflammation During Active Experimental autoimmune Encephalomyelitis", J Immunol, 169, pp. 4712-4716 (2002).
Brunstein CG, et al., "Infusion of ex vivo expanded T regulatory cells in adults transplanted with umbilical cord blood: safety profile and detection kinetics", Blood, 117(3):1061-70 (2011).
Humrich JY et al., "Rapid induction of clinical remission by lowdose interleukin-2 in a patient with refractory SLE", Ann Rheum Dis., 74(4):791-2 (2015).
Salek-Ardakani, et al., "OX40:OX40L Axis: Emerging Targets for Immunotherapy of Human Disease," Current Immunology Reviews, 2:37-53(2006.).
Boyer-Di Ponio, et al., "Biological function of mutant forms of JAGGED1 proteins in Alagille syndrome: inhibitory effect on Notch Signaling," Human Molecular Genetics, 16:2683-2692 (2007).
Hammond, et al., "Human OX40 ligand fusion protein (MEDI6383) as a potent OX40 agonist and immune-modulator in vitro and in vivo," Journal of Clinical Oncology, 33:1 (2015).
Benedito, et al., "The Notch Ligans Dll4 and Jagged 1 Have Opposing Effects on Angiogenesis," Cell, 137:1124-1135 (2009).
Voo, et al., "Antibodies Targeting Human OX40 Expand Effector T Cells and Block inducible and Natural Regulatory Cell Function," The Journal of Immunology, 191:3641-3650 (2013).
Sugamura, et al., "Therapeutic Targeting of The Effector T-Cell Co-Stimulatory Molecule OX40," Nature Reviews | Immunology, 4:420-431 (2004).
Progress in Autoimmune Disease Research, pp. 1-26 (2005).
Vas, et al., "Soluble Jagged-1 is able to inhibit the function of its multivalent form to induce hematopoietic stem cell self-renewal in a surrogate in vitro assay," Journal of Leukocyte Biology, 75:714-720 (2004).
Whisstock, et al., "Prediction of protein function from protein sequence and structure," Quarterly Review of Biophysics, 26:307-340 (2003).
Wang, et al., "A Single Amino Acid Determines Lysophospholipid Specificity of the S1P1 (EDG1) and LPA1 (EDG2) Phospholipid Growth Factor Receptors," J. Biological Chemistry, 276:49213-49220 (2001).

(Continued)

*Primary Examiner* — Amy E Juedes
(74) *Attorney, Agent, or Firm* — McDonnell Boehnen Hulbert & Berghoff LLP

(57) ABSTRACT

This invention relates to methods of expanding T regulatory cells through OX40L and Jagged-1 induced signaling. The methods can be used for treating autoimmune diseases.

3 Claims, 35 Drawing Sheets

Specification includes a Sequence Listing.

(56) References Cited

OTHER PUBLICATIONS

Müller, et al., "Activity of soluble OX40 ligand is enhanced by oligomerization and cell surface immobilization," FEBS Journal, 275:2296-2304 (2008).
Abbas, et al., "Functional diversity of helper T lymphocytes", Nature, 383:787-793 (1996).
Allan, et al., "The role of 2 FOXP3 isoforms in the generation of human CD4+ Tregs", The Journal of Clinical Investigation, 115:3276-3284 (2005).
Amsen, et al., "Instruction of Distinct CD4 T Helper Cell Fates by Different Notch Ligands on Antigen-Presenting Cells", Cell, 117:515-526 (2004).
Anastasi, et al., "Expression of Activated Notch3 in transgenic Mice Enhances Generation of T Regulatory Cells and Protects against Experimental Autoimmune Diabetes", The Journal of Immunology, 171:4504-4511 (2003).
Barbarulo, et al., "Notch3 and Canonical NF-kB Signaling Pathways Cooperatively Regulate Foxp3 Transcription", J Immunol, 186:6199-6206 (2011).
Bassil, et al., "Notch Ligand Delta-Like 4 Blockade Alleviates Experimental Autoimmune Encephalomyelitis by Promoting Regulatory T Cell Development", J Immunol., 187: 2322-2328 (2011).
Bernasconi, et al., "Granulocyte-Macrophage Colony-Stimulating Factor Elicits Bone Marrow-Derived Cells that Promote Efficient Colonic Mucosal Healing", Inflamm Bowel Dis., 16:428-441 (2010).
Bhattacharya, et al., "GM-CSF-induced, bone-marrow-derived dendritic cells can expand natural Tregs and Induce adaptive Tregs by different mechanisms", Journal of Leukocyte Biology, 89:235-249 (2011).
Campese, et al., "Notch3 and pTa/pre-TCR sustain the in vivo function of naturally occurring regulatory T cells", International Immunology, 21:727-743 (2009).
Cheatem, et al., "Modulation of Dendritic Cells Using Granulocyte-Macrophage Colony-Stimulating Factor (GM-CSF) Delays type 1 diabetes by Enhancing CD4+CD25+ Regulatory T Cell Function", Clin. Immunol. 131:260-270 (2009).
Elyaman, et al., "Jagged1 and Delta1 Differentially Regulate the outcome of Experimental Autoimmune Encephalomyelitis", J Immunol, 179:5990-5998 (2007).
Esquivel, et al., "Induction of Autoimmunity in Good and Poor Responder Mice with mouse Thyroglobulin and Lipopolysaccharide", The Journal of Experimental Medicine, 145:1250-1263 (1977).
Fortini, "Notch Signaling: The Core pathway and Its Post-translational Regulation", Developmental Cell, 16:633-647 (2009).
Ganesh, et al., "GM-CSF-induced CD11c1CD8a—dendritic cells facilitate Foxp31 and IL-101 regulatory T cell expansion resulting in suppression of autoimmune thyroiditis", International Immunology, 21:269-282 (2009).
Gangi, et al., "IL-10-Producing CD4+ CD25+ Regulatory T Cells Play a Critical Role in Granulocyte-Macrophage Colony-Stimulating Factor-Induced Suppression of Experimental Autoimmune Thyroiditis", J Immunol, 174:7006-1013 (2005).
Gaudreau, et al., "Granulocyte-Macrophage Colony-Stimulating Factor Prevents Diabetes Development in NOD Mice by Inducing Tolerogenic Dendritic Cells that Sustain the Suppressive Function of CD4+ CD25+ Regulatory T Cells", J Immunol, 179:3638-3647 (2007).
Godfrey, et al., "Identification of a Human OX-40 Ligand, a Costimulator of CD4+ T Cells with Homology of Tumor Necrosis Factor", J. Exp. Med., 180:757-762 (1994).
Griseri, et al., "OX40 is required for regulatory T cell-mediated control of colitis", J. Exp. Med., 207:699-709 (2010).
Hoyne, et al,. "Serrate 1-induced Notch signalling regulates the decision between immunity and tolerance made by peripheral CD4+ T cells", International Immunology, 12:177-185 (2000).
Joetham, et al., "Antigen Specificity Is not Required for Modulation of Lung Allergic Responses by Naturally Occurring Regulatory T Cells", The Journal of Immunology, 183:1821-1827 (2009).
Kared, et al., "Jagged2-Expressing Hematopoietic Progenitors Promote Regulatory T Cell Expansion in the Periphery through Notch Signaling", Immunity, 25:823-834 (2006).
Lee, et al., "Arachidonic acid potentiates hypoxia-induced VEGF expression in mouse embryonic stem cells: involvement of Notch, Wnt, and HIF-1α", Am J. Phsiol Cell Physiol, 297:C207-C216 (2009).
Minter, et al., "Inhibitors of γ-secretase block in vivo and in vitro T helper type 1 polarization by preventing Notch upregulation of Tbx21", Nature Immunology, 6:680-688 (2005).
Okamoto, et al., "Jagged1 on Dendritic Cells and Notch on CD4+ T Cells Initiate Lung Allergic Responsiveness by Inducing IL-4 Production", J Immunol, 183:2995-3003 (2009).
Rogers, et al., "OX40 Promotes Bcl-XL and Bcl-2 Expression and Is Essential for Long-Term Survival of CD4 T Cells", Immunity, 15:445-455 (2001).
Ruby, et al., "OX40 Agonists can drive Treg expansion if the cytokine milieu is right", J. Immunol., 183(4853-4857 (2009).
Sakaguchi, "Naturally Arising CD4+ Regulatory T Cells for Immunologic Self-Tolerance and Negative Control of Immune Responses", Ann. Rev. Immunol., 22:531-62 (2004).
Sakaguchi, et al., "Organ-Specific Autoimmune Diseases Induced in Mice by Elimination of T Cell Subset", J. Exp. Med., 161:72-87 (1985).
Samon, et al., "Notch1 and TGFß1 cooperatively regulate Foxp3 expression and the maintenance of peripheral regulatory T cells", Blood, 112:1813-1821 (2008).
Sheng, et al., "Suppression of Experimental Autoimmun Myasthenia Gravis by Granulocyte-Macrophage Colony-Stimulating Factor Is Associated with an Expansion of FoxP3+ Regulatory T Cells", J Immunol, 177:5296-5306 (2006).
Shevach, et al., "The lifestyle of naturally occurring CD4+CD25+ Foxp3+ regulatory T cells", Immunological Reviews 212:60-73 (2006).
So, et al., "OX40 Complexes with PI3K and PKB to Augment TCRDependent PKB Signaling", J Immunol. 186:3547-3555 (2011).
Song, et al., "The costimulation-regulated duration of PKB activation controls T cell longevity", Nature Immunology, 5:150-158 (2004).
Tang, et al., "In Vitro-expanded Antigen-specific Regulatory T Cells Suppress Autoimmune Diabetes", J. Exp. Med., 199:1455-1465 (2004).
Vacca, et al., "Notch3 and pre-TCR interaction unveils distinct NF-kB pathways in T-cell development and leukemia", The EMBO Journal, 25:1000-1008 (2006).
Vasu, et al., "Selective Induction of Dendritic Cells Using Granulocyte Macrophage-Colony Stimulating Factor, But Not fms-Like Tyrosine Kinase Receptor 3-Ligand, Activates Thyroglobulin-Specific CD4+/CD25+ T Cells and Suppresses Experimental Autoimmune Thyroiditis1", J Immunol. 170:5511-5522 (2003).
Vigouroux, et al., "Induction of Antigen-Specific Regulatory T Cells following Overexpression of a Notch Ligand by Human B Lymphocytes", Journal of Virology, 10872-10880 (2003).
Vu, et al., "OX40 costimulation turns off Foxp3+ Tregs", Blood, 110:2501-2510 (2007).
Yvon, et al., "Overexpression of the Notch ligand, Jagged-1, induces alloantigen-specific human regulatory T cells"., 102:3815-3821 (2003).
Zwar, et al., "CD4+CD25+ Regulatory T Cells Inhibit the Antigen-Dependent Expansion of Self-Reactive T Cells in Vivo"., 176:1609-1617 (2006).
Shimizu, et al., "Mouse Jagged1 Physically interacts with Notch2 and Other Notch Receptors"., The Journal of Biological Chemistry, 274:32961-32969 (1999).
Sadun, et al., "Fc-mOX4OL Fusion Protein Produces Complete Remission and Enhanced Survival in 2 Murine Tumor Models"., J. Immunoterapy, 31:235-245 (2008).
Compaan, et al., "The Crystal Structure of the Costimulatory OX40-OX40L Complex", Structure 14:1321-1330 (2006).
Hippen, et al., Umbilical cord blood regulatory T-cell expansion and functional effects of tumor necrosis factor receptor family members OX40 and 4-1BB expressed on artificial antigen-presenting cells, Blood, 112:2847-2857 (2008).

(56) References Cited

OTHER PUBLICATIONS

Bresson et al., "Antigen-specific prevention of type 1 diabetes in NOD mice is ameliorated by OX40 agonist treatment," J Autoimmun 37: 342-351 (2011).
Burchill et al., "IL-2 receptor beta-dependent STAT5 activation is required for the development of Foxp3+ regulatory T cells," J Immunol 178: 280-290 (2007).
Charbonnier et al., "Control of peripheral tolerance by regulatory T cell-intrinsic Notch signaling," Nat Immunol. 16: 1162-1173 (2015).
Choi et al., "Jagged-1 and Notch3 juxtacrine loop regulates ovarian tumor growth and adhesion," Cancer Res 68: 5716-5723 (2008).
Denes et al., "Autoantigens plus interleukin-10 suppress diabetes autoimmunity," Diabetes Technol Ther 12: 649-661 (2010).
Du et al., "Foxp3+ Treg expanded from patients with established diabetes reduce Helios expression while retaining normal function compared to healthy individuals," PLoS One 8: e56209 (2013).
Fletcher et al., "CD39+ Foxp3+ regulatory T Cells suppress pathogenic Th17 cells and are impaired in multiple sclerosis," J Immunol 183: 7602-7610 (2009).
Gopisetty et al., "OX40L/Jagged1 cosignaling by GM-CSF-induced bone marrowderived dendritic cells is required for the expansion of functional regulatory T cells," J Immunol 190: 5516-5525 (2013).
Haddad et al., "Age-dependent divergent effects of OX40L treatment on the development of diabetes in NOD mice," Autoimmunity 49: 1-14 (2016).
Hoffmann et al., "Loss of FOXP3 expression m natural human CD4+ CD25+ regulatory T cells upon repetitive in vitro stimulation," Eur J Immunol 39: 1088-1097 (2009).
Joller et al., "Treg cells expressing the coinhibitory molecule TIGIT selectively inhibit proinflammatory Th1 and Th17 cell responses," Immunity 40: 569-581 (2014).
Kawamata et al., "Activation of OX40 signal transduction pathways leads to tumor necrosis factor receptor-associated factor (TRAF) 2- and TRAF5-mediated NF-kappaB activation," J Biol Chem 273: 5808-5814 (1998).
Kieback et al., "Thymus-Derived Regulatory T Cells are Positively Selected on Natural Self-Antigen through Cognate Interactions of High Functional Avidity," Immunity 44:1114-1126 (2016).
Lal et al, "Epigenetic regulation of Foxp3 expression in regulatory T cells by DNA methylation," J Immunol 182: 259-273 (2009).
Mahmud et al., 2013. Interleukin-2 and STAT5 in regulatory T cell development and function, JAKSTAT 2: e23154 (2013).
Murawski et al., "Upregulation of Foxp3 expression in mouse and human Treg is IL-2/STAT5 dependent: implications for the NOD STAT5B mutation in diabetes pathogenesis," Ann NY Acad Sci 1079: 198-204 (2006).
Piconese et al., "OX40 triggering blocks suppression by regulatory T cells and facilitates tumor rejection," J Exp Med 205: 825-839 (2008).
Piconese et al., "A non-redundant role for OX40 in the competitive fitness of Treg in response to IL-2," Eur J Immunol 40: 2902-2913 (2010).
Rapoport et al., "Interleukin 4 reverses T cell proliferative unresponsiveness and prevents the onset of diabetes in nonobese diabetic mice," J Exp Med 178:87-99 (1993).
Rudra et al., "Runx-CBFbeta complexes control expression of the transcription factor Foxp3 in regulatory T cells," Nat Immunol 10: 1170-1177 (2009).
So et al., "Antigen-independent signalosorne of CARMA I, PKCtheta, and TNF receptorassociated factor 2 (TRAF2) determines NF-kappaB signaling in T cells," Proc Natl Acad Sci USA 108: 2903-2908 (2011).
Song et al., "Activation of NF-kappaBI by OX40 contributes to antigen-driven T cell expansion and survival," J Immunol 180:7240-7248 (2008).
Stephens et al., "Curing CNS autoimmune disease with myelin-reactive Foxp3+ Treg," Eur J Immunol 39, 1108-1117 (2009).
Takatori et al., "Helios Enhances Treg Cell Function in Cooperation With FoxP3," Arthritis Rheumatol 67: 1491-1502 (2015).
Valzasina et al., Triggering of OX40 (CD134) on CD4(+)CD25+ T cells blocks their inhibitory activity: a novel regulatory role for OX40 and its comparison with GITR. Blood 105: 2845-2851 (2005).
VanValkenburgh et al., "Critical role of Bcl11b m suppressor function of T regulatory cells and prevention of inflammatory bowel disease," J Exp Med 208: 2069-2081 (2011).
Wohlfert et al., "GATA3 controls Foxp3(+) regulatory T cell fate during inflammation in mice," J Clin Invest 121. 4503-4515 (2011).
Xiao et al., "New insights on OX40 in the control of T cell immunity and immune tolerance in vivo," J Immunol 188: 892-901 (2012).
Zaccone et al, "Interleukin-13 prevents autoimmune diabetes m NOD mice," Diabetes 48: 1522-1528 (1999).
Zorn et al., "IL-2 regulates FOXP3 expression in human CD4+ CD25+ regulatory T cells through a STAT-dependent mechanism and induces the expansion of these cells in vivo," Blood 108. 1571-1579 (2006).
Bhattacharya, et al,. "Dual Role of GM-CSF as Pro-Inflammatory and a Regulatory Cytokine: Implications for Immune Therapy", Journal of Interferon & Cytokine Research, 35:585-599 (2015).
Challener, "Fusion proteins pose manufacturability challenges," BioPharm Int. vol. 30(5), pp. 30-31 (2017).
Shimizu et al., "Physical interaction of Delta1, Jagged1, and Jagged2 with Notch1 and Notch3 receptors," Biochem. and Biophys. Res. Comm. vol. 276: 385-389 (2000).

\* cited by examiner

A

B

Control

OX40L/J-1

T-REG CELL EXPANSION

This application claims priority to U.S. patent application Ser. No. 14/186,766 filed Feb. 21, 2014, which claims priority to U.S. Provisional Patent application 61/768,204 filed Feb. 22, 2013, the contents of which are incorporated herein by reference in the entirety.

STATEMENT OF GOVERNMENT INTEREST

This invention was made with Government support under grant number A1 058190 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 3, 2017, is named 13-1803-US-CIP.txt and is 65.9 KB in size.

TECHNICAL FIELD

This application relates to the field of immunology. Particularly, this invention relates to methods of expanding T regulatory cells through OX40L and Jagged-1 induced signaling.

BACKGROUND OF THE INVENTION

T regulatory cells (Tregs) are important cells required for modulation of the immune system, maintaining tolerance to self-antigens and suppression of autoimmune diseases. The emergence of Tregs as a significant component of immune homeostasis provides a potential therapeutic opportunity for active immune regulation and long-term tolerance induction. Indeed, deficiency of naturally occurring T-regulatory cells (nTregs) has been observed in a variety of autoimmune conditions (36, 37). Moreover, adoptive transfer of polyclonal or antigen selected nTregs has been found to overcome autoimmune and allergic conditions (38-40). However, a limitation that prevents therapeutic utilization of Tregs in autoimmune diseases is the relative difficulty in obtaining large numbers of Tregs. Although much is known about T-cell receptor (TCR) mediated T cell activation and proliferation (25), signaling required for Treg proliferation in the absence of TCR stimulation remains largely unknown. Thus, an effective method for expanding Tregs is still needed.

SUMMARY OF THE INVENTION

This invention provides methods for expanding T regulatory cells through OX40L and Jagged-1 signaling. In accordance with the invention, methods are provided for expanding T regulatory cells comprising co-culturing said T-regulatory cells with one or more of a OX40L+ bone marrow derived dendritic cell culture differentiated in the presence of GM-CSF, a Jagged-1+ bone marrow derived dendritic cell culture differentiated in the presence of GM-CSF and a OX40L+Jagged-1+bone marrow derived dendritic cell culture differentiated in the presence of GM-CSF.

In another aspect, the invention provides methods of treating an autoimmune disease in a patient in need of such treatment comprising administering to the patient a therapeutically effective amount of T-regulatory cells prepared by co-culturing said T-regulatory cells with one or more of a OX40L+ bone marrow derived dendritic cell culture differentiated in the presence of GM-CSF, a Jagged-1+ bone marrow derived dendritic cell culture differentiated in the presence of GM-CSF and a OX40L+Jagged-1+ bone marrow derived dendritic cell culture differentiated in the presence of GM-CSF.

In yet another aspect, the invention provides methods for expanding T-regulatory cells comprising co-culturing said T-regulatory cells with one or more of soluble OX40L and soluble Jagged-1. In particular embodiments the OX40L and Jagged-1 are recombinantly produced. In particular embodiments one or more of soluble OX40L comprises the amino acid sequence set forth in any one of SEQ ID NOs:51 and 54, and one or more of soluble Jagged-1 comprises the gene encoded by the amino acid sequence set forth in any one of SEQ ID NOs:61 and 63.

In another aspect, the invention provides methods for treating an autoimmune disease in a patient in need of such treatment comprising administering to the patient a therapeutically effective amount of one or more of soluble OX40L and soluble Jagged-1. In particular embodiments the autoimmune disease is an autoimmune thyroid disease such as Grave's disease or Hashimoto disease. In other embodiments the autoimmune disease is Type 1 Diabetes mellitus. In other embodiments the OX40L and Jagged-1 are recombinantly produced. In yet other embodiments the patient is a human patient. In particular embodiments one or more of soluble OX40L comprises the amino acid sequence set forth in any one of SEQ ID NOs:51 and 54, and one or more of soluble Jagged-1 comprises the gene encoded by the amino acid sequence set forth in any one of SEQ ID NOs:61 and 63.

In another aspect, the invention provides methods treating an autoimmune disease in a patient in need of such treatment comprising administering to the patient a therapeutically effective amount of one or more of OX40L+ bone marrow derived dendritic cells differentiated in the presence of GM-CSF, Jagged-1+ bone marrow derived dendritic cells differentiated in the presence of GM-CSF and OX40L+ Jagged-1+bone marrow derived dendritic cells differentiated in the presence of GM-CSF. In particular embodiments the autoimmune disease is an autoimmune thyroid disease such as Grave's disease or Hashimoto disease. In other embodiments the autoimmune disease is Type 1 Diabetes mellitus. In other embodiments the OX40L and Jagged-1 are recombinantly produced. In yet other embodiments the patient is a human patient. In particular embodiments one or more of soluble OX40L comprises the amino acid sequence set forth in any one of SEQ ID NOs:51 and 54, and one or more of soluble Jagged-1 comprises the gene encoded by the amino acid sequence set forth in any one of SEQ ID NOs:61 and 63.

DETAILED DESCRIPTION OF THE INVENTION

Figure 1:
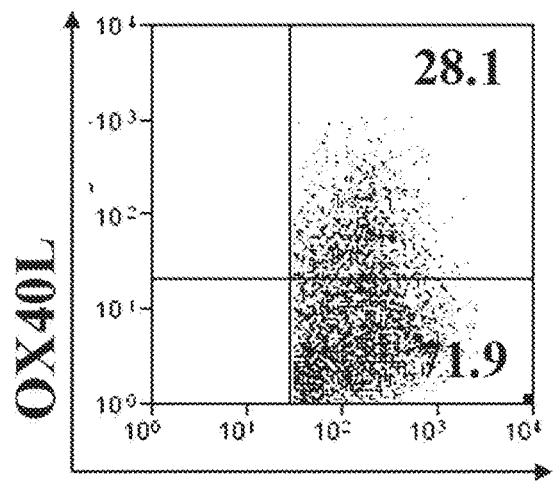
FIG. 1. OX40L is necessary but not sufficient for GM-BMDC directed ex vivo expansion of Tregs. (A). Percentage of OX40L' bone marrow derived dendritic cells (GM-BMDCs) differentiated in the presence of granulocyte macrophage colony stimulating factor (GM-CSF) gated on CD11c+ cells. (B) GM-BMDCs derived ex vivo from bone marrow cells of WT C57B6/j mice were sorted after 7 days of differentiation with GM-CSF. Nave carboxy fluorescein succinimidyl ester (CFSE) labelled CD4+ T-cells were co-cultured with either splenic dendritic cells (SpDCs), or total, OX40L⁺ or OX40L⁻ enriched GM-BMDCS for 5 days without exogenous antigen and analyzed by FACS. (C). Total, OX40L⁺ or OX40L⁻ GM-BMDCs were co-cultured with Cell-Trace violet labelled sorted GFP+ and GFP− T-cells from Foxp3-GFP mice after CD4⁺ based enrichment for 5 days without exogenous antigen and analyzed by FACS. Co-cultures of GFP⁺ (Foxp3⁺) cells without IL-2 (upper panel) and with IL-2 (lower panel) are shown. (D). Co-cultures of GFP⁻ (Foxp3⁻) cells without IL-2 (upper panel) and with IL-2 (lower panel) are shown. Each scatter plot is representative of five independent experiments, gated over 3500 live CD4⁺ T-cells. Each in vitro experiment was conducted with T-cells, SpDCs and GM-BMDCs pooled from 3 mice. (E) Sorted OX40L⁺ or OX40L⁻ GM-BMDCs were co-cultured with CFSE labelled CD4⁺ T-cells and supplemented with OX40 agonist. Co-cultures were analyzed by FACS on day 5 to determine T-cell proliferation.
Figure 1:
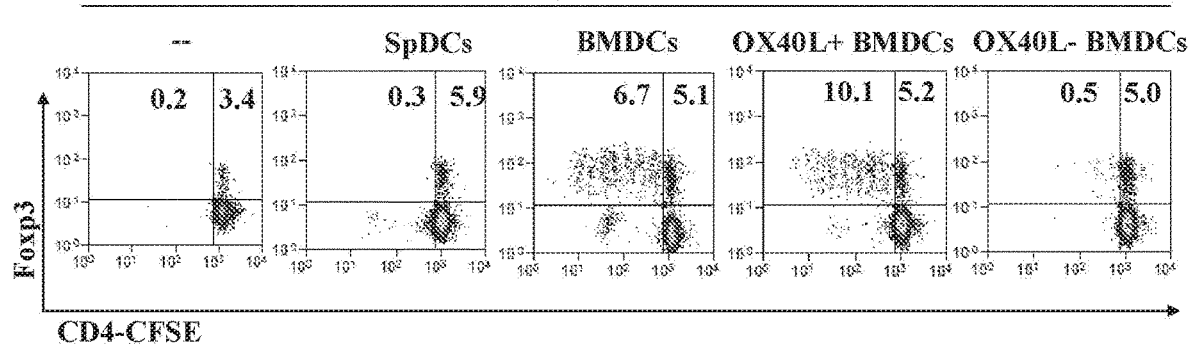
Figure 1:
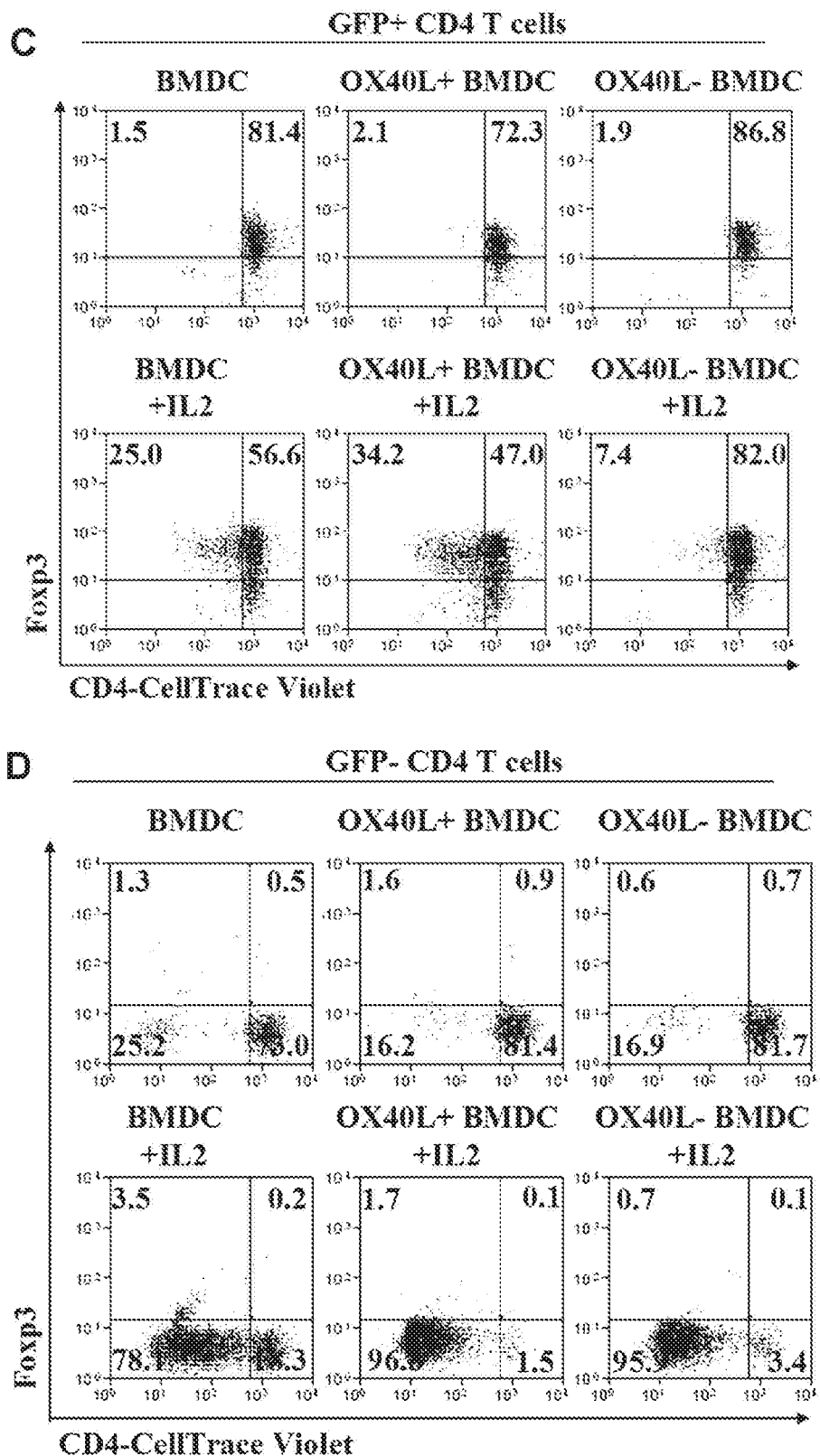
Figure 1:
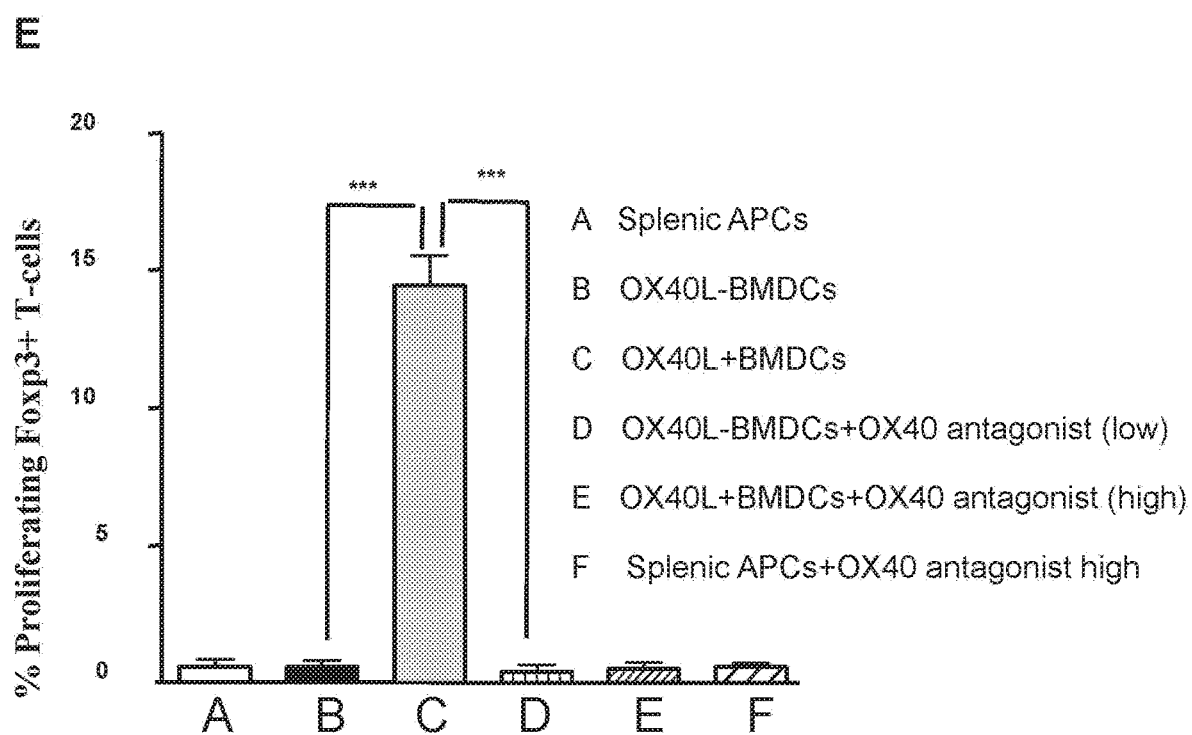

The invention provides methods for expanding T-regulatory cells (Tregs) using OX40L and Jagged-1 induced signaling. In particular embodiments, the OX40L and/or Jagged-1 are expressed on bone marrow derived dendritic cells differentiated in the presence of GM-CSF (GM-BMDC). Additionally, OX40L and Jagged-1 can be used in the soluble form for expansion of Tregs. The invention also provides methods for treating autoimmune diseases by increasing the number of Tregs as a result of OX40L and Jagged-1 induced signaling.

Unless otherwise explained, all technical and scientific terms used herein have the same meaning as commonly understood by one of ordinary skill in the art to which a disclosed disclosure belongs.

The singular terms "a," "an," and "the" include plural referents unless context clearly indicates otherwise. Similarly, the word "or" is intended to include "and" unless the context clearly indicates otherwise.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms "T regulatory cell" or "Tregs" as used herein refer to a cell that can modulate a T cell response. Tregs express the transcription factor Foxp3, which is not upregulated upon T cell activation and discriminates Tregs from activated effector cells. Tregs are classified into natural or adaptive (induced) Tregs on the basis of their origin. Foxp3 natural Tregs (nTregs) are generated in the thymus through MHC class II dependent T cell receptor. Adaptive Tregs are non-regulatory CD4+ T-cells which acquire CD25 (IL-2R alpha) expression outside of the thymus, and are typically induced by inflammation and disease processes, such as autoimmunity and cancer. The methods described herein can employ Tregs that expresses one or more of CD4, CD25 and Foxp3.

OX40L belongs to the tumor necrosis factor superfamily with co-stimulatory function. OX40L when expressed on antigen-presenting cells binds to OX40 expressed on T-cells.

The Jagged members (Jagged-1 and Jagged-2) of Notch family ligands have been shown to play important role in Treg expansion (12, 13). The Notch family has 4 known receptors, Notch-1, -2, -3 and -4, and five known Notch ligands namely, DLL1, DLL3 and DLL4, and Jagged-1 and Jagged-2. Upon ligand binding, Notch receptors undergo two proteolytic cleavages. The first cleavage is catalysed by ADAM-family metalloproteases and is followed by the gamma-secretase mediated release of Notch intracellular domain (NICD). The NICD translocates to the nucleus where it forms a heterodimeric complex with various co-activator molecules and acts as a transcriptional activator (15). Expression of specific Notch ligands on dendritic cells (DCs) is known to activate specific T-cell responses (14). While Jagged ligands have been shown to direct naive T-cells toward Th2 and/or Treg type of responses, Delta like ligands (DLL) have been shown to skew them towards a Th1 response (16). Of relevance to the current invention are earlier reports of Treg expansion by hematopoietic progenitors expressing Jagged-2 and APCs over-expressing Jagged-1 (12, 13, 17, 18). Similarly, DLL4 blockade ameliorated experimental autoimmune encephalomyelitis (EAE) (20).

While OX40 is constitutively expressed on Tregs (27), Notch 3 is preferentially expressed on Tregs (24). In the context of TCR signaling, OX40 mediated-signaling can increase T cell proliferation by activating PI3 kinase (PI3K) and Akt, which are upstream activators of mTOR (28). GM-BMDCs derived from MHC class-II knockout mice were also able to expand Tregs and indicated that TCR signaling was not necessary (8). OX40 activation can form a signalosome consisting of CARMAI. PKC-Q and TRAF2 and cause enhanced NF-KB activation and contribute to cell survival and expansion (29, 30). Notch 3 has been reported to activate both the alternate and the canonical NF-KB pathways. It can activate the alternative (ReB) NF-KB pathway in murine thymocytes (31) via cytoplasmic IKKa and cooperate with canonical NF-KB in stimulating FoxP3 expression (32). Thus NF-KB may be an important point of convergence between OX40 and Notch 3 signaling in Tregs.

Notch 1 has been reported to maintain expression of FoxP3 in peripheral Tregs in collaboration with TGFβ (33). Therefore, it is possible that different Notch paralogs can maintain FoxP3 expression depending on other signals and cellular context. It is well known that Foxp3+ Tregs are unable to proliferate or proliferate poorly when stimulated (34, 35) and upon proliferation they lose Foxp3 expression. Notch 3 has been shown to co-operatively regulate Foxp3 expression through trans-activation of the Foxp3 promoter (32). Therefore, it is likely that the interaction of Jagged-1 with Notch 3 helps sustain Foxp3 transcription while OX40 signalosome formation, in the absence of TCR signaling, may drive Foxp3+ Treg cell-proliferation. Thus, concurrent signals from Notch 3 and OX40 can allow Treg proliferation while sustaining Foxp3 expression.

A growing body of evidence demonstrates the protective role for Foxp3+ Tregs in various autoimmune diseases (39,41,42). However, translation of Treg cell therapy to clinical settings is impeded by several limitations. One of these limitations is the inability of TCR-dependent approaches to cause selective in vivo expansion of Tregs (43). Unlike stimulation with anti-CD3/CD28 which activated both Tregs and Teff cells, stimulation with OX40L-JAG1 caused selective proliferation of Tregs without activating Teffs as evidenced by no significant change in the expression of activation markers such as CD25, CD44 and CD69 on Teff cells. Differential gene expression analysis between resting vs proliferating Tregs showed up-regulation of expression of Foxp3 and its functional partners Gata3, Runx1, Cnot3, Cbb, Cebpz and Bcl11b in proliferating Tregs. These molecules are known to increase the functional fitness of Tregs. For example, expression of Gata3 by Tregs is essential for their migration towards the site of inflammation and to sustain Foxp3 expression under inflammatory conditions (44). Runx and CBF-β complex have been shown to directly bind to Foxp3 promoter and increase its transcription (45). Similarly, transcription factor Bcl11b can bind to both Foxp3 and IL-10 promoters, and regulate their expression and help confer Treg mediated protection against IBD (46).

Regarding observance of up-regulation of suppressive and stable phenotypic markers of Tregs, including Ctla-4, Helios, Tigit, Icos, Cd39, Pdcd1 and Tgf-β1, CTLA-4 is one of the most widely accepted mediators of Treg suppressive functions (42). CD39, an ectonucleotidase that can hydrolyze ATP, is considered as a stability marker for Tregs and $CD39^+$ Foxp3+ Tregs have been shown to suppress both Th1 and Th17 cells (47). TIGIT is another Treg cell specific coinhibitory molecule. TIGIT+ subset of Tregs have been shown to predominantly inhibit Th1 and Th17 cells without affecting Th2 cells (48). Helios, an Ikoras transcription factor family member, has also been reported to be associated with Treg functions (49) and suppression of autoimmune diabetes (50). Increased expression of these suppressive markers in OX40L-JAG1 expanded Tregs could help sustain their suppressive functions. Furthermore, the functional competency of these expanded Tregs was also confirmed in ex vivo suppressive assays.

It has been observed that treatment of 6-week old NOD mice with either OX40L or an anti-OX40 agonistic antibody (OX86) can increase CD4+CD25+ Foxp3+Treg cells and protect NOD mice from developing diabetes (51,52). However, treating 12-week old NOD mice with OX40L accelerated diabetes development, likely due to an increased pro-inflammatory environment associated with aging in these mice (52). Previous reports have demonstrated the protective effects of anti-inflammatory cytokines such as IL-4, IL-10 and IL-13 in autoimmune diabetes (53-55). Together, these results suggested that OX40L and JAG1 co-treatment might have restored the balance between anti- and pro-inflammatory cytokines, and created a favorable cytokine milieu in which Tregs could proliferate and retain their suppressive functions.

The relevance of OX40L induced signaling in Treg expansion and function has remained elusive. OX40 expression has been shown to be essential for Treg migration to inflamed sites (56-58). While OX40L-OX40 stimulation can cause Treg proliferation, it could also adversely affect Foxp3 expression and Treg suppressive functions depending upon the local cytokine milieu (27,59). During TCR stimulation OX40L-OX40 interaction has been shown to activate PI3K (PI-3-kinase)/PKB (protein kinase B/Akt) and NF-κ B1 pathways (28,60). Two members of the TRAF family of proteins such as TRAF2 and TRAF5 have been identified as key adaptor proteins recruited by OX40 to drive NF-kB1 activation (61). In the absence of TCR stimulation, OX40 has been shown to form a signalosome containing TRAF2, CARMAI, MALT1, BCL10, PKCBθ, RIP and IKKα/β/γ to cause NF-kB activation required for T-cell survival (62). Several lines of evidence suggest that Notch signaling plays a positive role in Treg homeostasis by increasing Treg numbers in thymus and periphery, and by maintaining Foxp3 expression (12,24,26). In particular, Notch3 has been shown to positively regulate nTreg development and Foxp3 expression (26). It has been shown that Notch3 and canonical NF-κ B signaling pathways could co-operatively regulate Foxp3 expression (32). Hence, JAG1 induced Notch3 signaling, along with transactivation of NF-κ B-p65 by OX40L, could co-operatively regulate Treg proliferation and Foxp3 expression.

The role of IL-2 induced STAT5 signaling in Treg survival and stable Foxp3 expression is well established (63). Foxp3 promoter has a STAT5 binding site (64) through which Foxp3 expression is regulated in both human and mouse Tregs (65). In addition, Foxp3 gene has a T-Cell Specific Demethylated Region (TSDR) in its promoter which can be demethylated through IL-2/STAT5 signaling to sustain Foxp3 expression (66,67).

Using GM-BMDC from MHC class-II deficient mice, OX40L mediated ex vivo expansion of Tregs has been shown not to require T-cell receptor (TCR) stimulation per se although it was critically depended on exogenous IL-2 (8). Notch 3 mediated signaling has been reported to sustain regulatory phenotype on Tregs (26). Furthermore, thymocytes and T cells from transgenic mice expressing Notch 3 NICD (N3-μg mice) in which Notch3 is constitutively active contain a significantly higher proportion of CD4'CD25+ cells (24).

In particular aspects of the invention, the method includes expanding T-regulatory cells by co-culturing T-regulatory cells with a bone marrow-derived dendritic cell differentiated in the presence of GM-CSF that expresses a co-stimulatory molecule such as OX40L and/or Jagged-1. The term "expanding" as used herein refers to increasing the number of cells in the cell population due to cell replication.

Treatment with low dose GM-CSF has been found to be sufficient to prevent the development of Experimental Autoimmune Thyroiditis (EAT) in CBA mice, Experimental Autoimmune Myasthenia Gravis (EAMG) in C57BL mice and Type 1 Diabetes (T1D) in NOD mice (1-3). Moreover, such treatment reversed ongoing EAT and EAMG, and restored normal thyroid and neuromuscular conduction respectively (1, 2). Others have shown similar protective effect of GM-CSF in T1D and Irritable Bowel Disease (IBD) (4, 5). Additionally, the therapeutic effect of GM-CSF was primarily mediated through the mobilization of $CD11c^+$ $CD8\alpha^-$ DCs (6), which caused expansion of regulatory Tregs. These expanded Tregs suppressed the disease through increased IL-10 production (7).

Additionally, GM-CSF can differentiate bone marrow derived DC precursors ex vivo and cause a selective expansion of $CD11c^+CD11b^+CD8\alpha^-$DCs (GM-BMDCs) (8). Unlike DCs isolated from the spleen (SpDCs), these ex vivo developed GM-BMDCs were able to directly and specifically expand Tregs upon co-culture with $CD4^+$ T-cells. Furthermore, treatment of mice with GM-CSF led to an increase in $CD11c^+CD11b^+CD8\alpha^-$DCs in vivo with concomitant increase in $Foxp3^+$ Tregs, suggesting a parallel mechanism of $CD11c^+CD11b^+CD8\alpha^-$DCs mediated Treg expansion ex vivo and in vivo.

Using GM-BMDCs from MHC class-II$^{-/-}$ mice, it has been shown that Treg expansion by these DCs did not require canonical antigen presentation to TCR but required exogenous IL-2 (8). Using blocking antibodies to co-stimulatory molecules expressed on the surface of GM-BMDCs, it was shown that the GM-BMDC mediated Treg proliferation was dependent upon GM-BMDC bound OX40L (8), a member of the tumor necrosis factor super family with co-stimulatory function (9). Studies by other groups have also suggested a novel role for OX40L-OX40 interaction in the expansion of Tregs (10, 11).

In other aspects of the invention, the methods include expanding T-regulatory cells by co-culturing the T-regulatory cells with soluble OX40L and/or soluble Jagged-1. In some aspects, one or more of soluble OX40L comprises the amino acid sequence set forth in any one of SEQ ID NOs:51-55, and wherein one or more of soluble Jagged-1 comprises the amino acid sequence set forth in any one of SEQ ID NOs:61-64. In other particular aspects, the one or more of soluble OX40L comprises the amino acid sequence set forth in any one of SEQ ID NOs:51 and 54, and wherein one or more of soluble Jagged-1 comprises the amino acid sequence set forth in any one of SEQ ID NOs:61 and 63.

The term "soluble" as used herein describes molecules that lack any transmembrane domain or protein domain that anchors or integrates the polypeptide into the membrane of a cell expressing such polypeptide.

In other aspects of the invention, the methods include treating an autoimmune disease using the Tregs produced through OX40L and/or Jagged-1 induced signaling. For example, an autoimmune disease in a patient in need of such treatment can be treated using the Tregs produced as a result of co-culturing Tregs with a therapeutically effective amount of one or more of a OX40L*GM-BMDC, a Jagged-1$^+$ GM-BMDC and a OX40L$^+$Jagged-1$^+$ GM-BMDC. Additionally, the Tregs produced by any of the methods disclosed herein can be used for treatment of an autoimmune disease in a patient in need thereof.

In other particular aspects, the method includes treating an autoimmune disease in a patient in need of such treatment comprising administering to the patient a therapeutically effective amount of one or more of soluble OX40L and soluble Jagged-1. In some aspects, one or more of soluble OX40L comprises the amino acid sequence set forth in any one of SEQ ID NOs:51-55, and wherein one or more of soluble Jagged-1 comprises the amino acid sequence set forth in any one of SEQ ID NOs:61-64. In other particular aspects, the one or more of soluble OX40L comprises the amino acid sequence set forth in any one of SEQ ID NOs:51 and 54, and wherein one or more of soluble Jagged-1 comprises the amino acid sequence set forth in any one of SEQ ID NOs:61 and 63.

The term "patient" as used herein refers to a mammal suffering from an autoimmune disease. In certain particular embodiments, the mammal is a human. In other certain embodiments, a patient is a human suffering from an autoimmune disease.

The term "autoimmune diseases" as used herein refers to a disease resulting from an immune response against a self-tissue or tissue component, including both self-antibody responses and cell-mediated responses. Exemplary autoimmune diseases that are suitable as targets for the inventive methods are type I diabetes mellitus (TD), Crohn's disease, ulcerative colitis, myasthenia gravis, vitiligo, Graves' disease, Hashimoto's disease, Addison's disease and autoimmune gastritis and autoimmune hepatitis, rheumatoid disease, systemic lupus erythematosus, progressive systemic sclerosis and variants, polymyositis and dermatomyositis, pernicious anemia including some of autoimmune gastritis, primary biliary cirrhosis, autoimmune thrombocytopenia, Sjogren's syndrome, multiple sclerosis and psoriasis. One skilled in the art understands that the methods of the invention can be applied to these or other autoimmune diseases, as desired.

As used herein, the term "amount effective," "effective amount" or a "therapeutically effective amount" refers to an amount of compound or composition sufficient to achieve the stated desired result, for example, treating or limiting development of autoimmune disease. The amount of the compound or composition which constitutes an "effective amount" or "therapeutically effective amount" may vary depending on the severity of the disease, the condition, weight, gender or age of the patient to be treated, the frequency of dosing, or the route of administration, but can be determined routinely by one of ordinary skill in the art. A clinician may titer the dosage or route of administration to obtain the optimal therapeutic effect.

In particular embodiments the autoimmune disease is an autoimmune thyroid disease (e.g., Grave's disease and Hashimoto disease). Autoimmune thyroid disease involves the dysfunction of the diseased thyroid gland and varies from hypothyroidism due to glandular destruction in Hashimoto's thyroiditis or blocking antibodies in primary myxedema to hyperthyroidism in Graves' disease due to thyroid simulating antibodies. In other particular aspects the autoimmune disease is Type 1 Diabetes Mellitus.

Cellular therapies for autoimmune diseases, including formulations and methods of administration are known in the art and can be applied to the T-regulatory cells and vectors described herein. See, for example, in EP1153131 A2, incorporated herein by reference.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used.

The foregoing may be better understood by reference to the following examples which are presented for purposes of illustration and are not intended to limit the scope of the invention.

EXAMPLES

Materials and Methods:
Animals:
Six to eight week old CBA/J mice were purchased from the Jackson Laboratory.

Mice were housed and provided food and water ad libitum. CD80−/−, CD86−/−, CD80−/− CD86−/− Foxp3GFP and WT (C57B6/j background) mice were kindly provided by Dr. Chenthamarakshan Vasu (Department of Surgery, Medical University of South Carolina). For some experiments, non-obese diabetic ("NOD"), C57BL/6 J, B6129SF1/J, OX40 and Notch3 deficient mice were purchased from Jackson Laboratories. MHC class-II deficient mice (ABBN12 (H2-Ab1)) were from Taconic biosciences. Breeding colonies were established and maintained in a pathogen-free facility of the biological resources laboratory (BRL) of the University of Illinois at Chicago (Chicago, IL).

GM-CSF, Antibodies and Thyroglobulin:

Recombinant GM-CSF and CFSE were purchased from Invitrogen (Carlsbad, USA). Phycoerythrin-conjugated anti-H-2K$^d$ (MHC class II), anti-Jagged-1, anti-DLL1, anti-DLL3, anti-DLL4, anti-Notch 1; Pacific blue conjugated anti-CD4, APC conjugated anti-CD11c, anti-CD11 b, anti-Foxp3, antiCD3, PE conjugated anti-IL-4, and IFN-γ antibodies, and OX40 agonist (OX86) were purchased from eBioscience (San Diego, CA). APC conjugated anti-OX40L antibody was purchased from Biolegend (San Diego, CA). Blocking antibodies to OX40L (AF1236), Jagged-1 (AF599), Notch 1 (AF1057) and Notch 3 (AF1308) and normal goat IgG control (AB-108-C) were purchased from R&D systems (Minneapolis, MN). Primary and secondary antibodies for staining intracellular Notch receptors (NICD) against Notch 1 (sc-23307) and Notch 3 (se-5593) (12, 21) were purchased from Santa Cruz Biotechnology (Santa Cruz, CA). Mouse thyroids were purchased from Pel-Freeze (Rogers, AR) and thyroglobulin was prepared as described earlier (22). In brief, thyroids were homogenized in 2.5 ml PBS with pestle-homogenizer (Wheaton, Millville, NJ) with overnight extraction at 4° C. The extract was clarified by centrifugation (15000×g) and fractionated on a Sephadex G-200 column (2.5 cm×90 cm) that had been equilibrated with 0.1 M phosphate buffer, pH 7.2. The concentration and purity of mTg was determined spectrophotometrically at 280 nm and by resolving on 7% SDS-PAGE followed by Coomassie blue staining. Gamma-secretase inhibitors (GSI) S-2188 and RO4929097 were purchased from Sigma-Aldrich (St. Louis, MO) and Selleck Chemicals (Houston, TX) respectively.

Isolation of DC and T-Cell Subpopulations:

Bone marrow cells were cultured in complete RPMI medium containing 10% heat-inactivated FBS in the presence of 20 ng/ml GM-CSF for 3 days. On days 4 and 6, fresh medium containing 20 ng/ml GM-CSF was added. Non-adherent CD11c$^+$ DCs from eight day old cultures were enriched using anti-CD11c coated magnetic beads according to the manufacturer's directions (Miltenyi Biotech, Auburn, CA). Specific sub-populations of GM-BMDCs and CD4+CD25+ T-cells were sorted using a MoFlo flow cytometer (Beckman/Coulter, Ranch Cucamonga, CA) following staining with appropriate antibodies (OX40L, Jagged-1, CD4, CD25). To obtain GFP+ and GFP− cells, total CD4+ cells were first separated using CD4 microbeads (Miltenyi Biotech) and then the cells were sorted based on GFP expression using a MoFlo flow cytometer (Beckman/Coulter). For some experiments, spleens were excised and single cell suspensions were prepared and over 90% pure total CD4$^+$ T-cells and CD4+CD25+ Tregs were isolated according to the manufacturer's protocol (Miltenyi Biotech, CA). To derive G-BMDCs, cells isolated from femoral bones were cultured in complete RPMI-1640 containing 10% FBS supplemented with GM-CSF (20 ng/ml) for seven days. From this culture CD11c+G-BMDCs were sorted and co-cultured with Cell-Trace Violet (Life technologies) labeled CD4$^+$ T-cells at 1:1 ratio for five days. For TCR stimulation, cells were cultured in anti-CD3 (2 μg/ml) coated plates in the presence of anti-CD28 (2 μg/ml) (eBioscience) and IL-2 (50 IU/ml) for 72 h. In some experiments splenocytes and CD4$^+$ T-cells (1×106/ml) were treated with recombinant mOX40 L (5 μg/ml) and mJAG1 (1 μg/ml) and mIL-2 (10 IU/ml) for 24-120 h. For proliferation experiments splenocytes and CD4$^+$ T-cells were stained with Cell-Trace violet and then treated with OX40L-JAG1-IL-2.

In Vitro Co-Cultures of DCs and T Cells:

Each in vitro experiment was conducted in triplicate with T-cells, SpDCs and GM-BMDCs pooled from 3 mice. GM-BMDCs (5×10$^4$) and CD11c$^+$ SpDCs were cultured with CD4$^+$, CD4$^+$CD25$^+$ and CD4+CD25$^+$ T-cells at a ratio of 1:2 for 5 days. For proliferation assays, T-cell subpopulations were labelled with CFSE at 10 μM according to manufacturer's instruction (Invitrogen, Carlsbad, CA) before co-culturing them with DCs. Some cultures were supplemented with IL-2 (IOU/ml) (R&D Systems), antiOX40L (up to 10 μg/ml) antibody, OX40 agonist (OX-86, 5-10 μg/ml), anti-Jagged-1 (10-20 μg/ml) antibody or anti-Notch3 (10-20 μg/m) antibody. For blocking experiments with anti-OX40L or anti-Jagged-1 antibodies, GM-BMDCs were pre-treated with the indicated antibodies for 30 min at 37° C. and then used in co-culture with naive CD4$^+$ T-cells. For blocking experiments with anti-Notch3 antibody, CD4+ T-cells isolated from mouse splenocytes were first treated with anti-Notch3 antibody at two different concentrations (10 and 20 μg/ml) or with 20 μg/m of an anti-Notch1 antibody, incubated at 37° C. for 30 minutes and then co-cultured with GM-BMDCs/SpDCs for 5 days. Some co-cultures were supplemented with different concentrations of gamma-secretase inhibitors (GSI) S-2188 (5 and 10 μM) or R04929097 (200 nM-5 μM).

Suppression Assay:

CD4$^+$CD25$^-$ effector T-cells were isolated from spleens, stained with CFSE and plated into flat bottom 96 well plates at 0.5×10$^6$ cells/well in the presence of either OVA or mTg (100 μg/m) and splenic antigen presenting cells (APCs). Sorted CD4$^+$CD25$^+$ Tregs from ex vivo co-cultures of naïve CD4$^+$ T-cells and GM-BMDC were added at different ratios to the co-culture containing CD4$^+$CD25$^-$ T-cells from primed mice.

Propidium Iodide (PI) and Intracellular Staining:

Briefly, at the end of co-culture experiments, T-cells were stained with Pacific blue labelled anti-mouse CD4 antibody and cells labelled with propidium iodide and subjected to FACS analysis to assess cell viability. For intracellular staining, surface stained cells were fixed and permeabilized using a commercial kit and according to the manufacturer's instructions (eBioscience) and incubated with specified antibodies.

Western Blot:

CD4+ T-cells (1×10$^6$ cells/ml) were treated with soluble OX40 L, JAG1 and IL-2 as mentioned above. In some experiments cells were pre-treated with inhibitors of Notch (GSI-RO4929097, Selleckchem), NF-κB (BAY-11-7082, Sigma-Aldrich) and STAT5 (CAS 285986-31-4, Calbiochem) signaling for 2 h and co-treated with soluble ligands for different time intervals. Cells were washed with PBS, and lysed in Laemmli buffer (Biorad) and resolved in 10% SDS-PAGE gels. Proteins were transferred to PVDF membranes (Biorad), blocked with 5% skimmed milk and incubated with primary anti-mouse Foxp3 (1:1000, ebioscience), anti-mouse phospho p65 (Ser536) and phospho STAT5 (Tyr694) (1:500, Cell Signaling Technology) antibodies. Blots were then washed, incubated with secondary anti-rabbit IgG-HRP and developed using ECL detection kit (Pierce Scientific). Blots were stripped and re-probed with anti-mouse β-actin-HRP antibody (1:5000; Santacruz Biotechnology), anti-mouse p65 and STAT5 (1:500, Cell Signaling Technology), and developed. Densitometry analysis was done using MyImage Analysis software (Thermo Scientific). Foxp3, pp65 and pSTAT5 signal intensities were normalized to β-actin, total p65 and STAT5 signal intensities and expressed as fold change over respective controls.

FACS:

Freshly isolated and ex vivo cultured cells were washed with PBS-BSA-EDTA or PBS containing 0.5% BSA. For surface staining, the cells were labelled with one of the following: specified FITC, PE, APC conjugated antibodies for 30 min, anti-CD4-eFluor-780, CD4-FITC (eBioscience), anti-CD25-PE, anti-CTLA4-PE, anti-CD39-PE, anti-Helios-PE, anti-TIGIT-PE or fixed, permeabilized, and stained with anti-, Anti-Ki67-PE, anti-Foxp3-APC and isotype controls antibodies (eBioscience) (1:100) in dark. For cell proliferation assays, the cells were labelled with CFSE, fixed, permeabilized and incubated with fluorescent coupled antibodies for intracellular staining. Stained cells were washed three times and analyzed by Cyan flow cytometer (Beckman/Coulter) and data analysis was done using Summit v4.3 software.

Suppression Assay:

CD4+CD25+ Tregs sorted from control and OX40L-JAG1 treated were co-cultured with CFSE-labeled CD4+ CD25− Teff cells at 1:16, 1:8, 1:4, 1:2 and 1:1 ratios and stimulated with anti-CD3/anti-CD28. Extent of proliferation was measured by cell trace violet dilution and percentage of suppression of Teff cell proliferation was calculated as described previously (68).

Cell Stimulation and Cytokine Expression Analysis:

Splenocytes from PBS and OX40L-JAG1 treated mice were stimulated with 500× cell stimulation cocktail (eBioscience) containing PMA and ionomycin with protein transport inhibitors for 16-24 h. mRNA expression of cytokines such as IFN-γ, IL-12α, IL-12β, TNF-α, IL-4, IL-5, IL-13, IL-10, IL-6 and IL-17 was analyzed by RT-qPCR as described above using primers listed in [0073].

siRNA Transfection into GM-BMDC:

A 21 bp si RNA sequence (Dharmacon, Lafayette, CO) specific to Jagged-1 (5'-CTCGTAATCCTTAATGGTT-3'; SEQ ID NO: 11) was used at a final concentration of 120 nM as previously described (23). Briefly, 3 µl of 20 µM annealed siRNA was incubated with 3 µl of GenePorter (Gene Therapy Systems) in a volume of 94 µl of serum-free RPMI 1640 at room temperature for 30 min. This mixture was added to each well containing GM-BMDC in avolume of 500 µl and incubated for 4 h at 37° C. 3 µl of GenePorter alone was used for mock transfection as anegative control. After incubation, 500 µl/well of RPMI 1640 supplemented with 20% FCS was added and twenty-four hours later, GM-BMDCs were washed and used.

RT-PCR:

Total RNA was extracted using TRIzol reagent (Invitrogen) and the first strand cDNA was synthesized using Superscript 2 (Invitrogen). Gene specific primers were used for semi quantitative PCR amplification (0.5 min at 94° C., 0.5 min at 55° C., and 0.5 min at 72° C. for 33 cycles) to detect relative amounts of different transcripts. The following primer sets were used to amplify the indicated products:

HPRT-F, SEQ ID NO: 1
GTTGGATACAGGCCAGACTTTGTTG

HPRT-R, SEQ ID NO: 2
TACTAGGCAGATGGCCAGGACTA

Notch1-F, SEQ ID NO: 3
TGTTAATGAGTGCATCTCCAA

Notch1-R, SEQ ID NO: 4
CATTCGTAGCCATCAATCTTGTC

Notch2-F, SEQ ID NO: 5
TGGAGGTAAATGAATGCCAGAG

Notch2-R, SEQ ID NO: 6
TGTAGCGATTGATGCCGTC

Notch3-F, SEQ ID NO: 7
ACACTGGGAGTTCTCTGT

Notch3-R, SEQ ID NO: 8
GTCTGCTGGCATGGGATA

Notch4-F, SEQ ID NO: 9
CACCTCCTGCCATAACACCTTG

Notch4-R, SEQ ID NO: 10
ACACAGTCATCTGGGTTCATCTCAC

Foxp3-F, SEQ ID NO: 11
CGAACATGCGAGTAAACCAATG

Foxp3-R, SEQ ID NO: 12
CTTTCACCTATGCCACCCTTA

GAPDH-F, SEQ ID NO: 13
GTGGAGTCATACTGGAACATGTA

GAPDH-R, SEQ ID NO: 14
AATGGTGAAGGTCGGTGTG

Notch3-F, SEQ ID NO: 15
AGTGCCGATCTGGTACAACTT

Notch3-R, SEQ ID NO: 16
CACTACGGGGTTCTCACACA

Prkcq-F, SEQ ID NO: 17
TATCCAACTTTGACTGTGGGACC

Prkcq-R, SEQ ID NO: 18
CCCTTCCCTTGTTAATGTGGG

NF-KB1-F, SEQ ID NO: 19
ATGGCAGACGATGATCCCTAC

NF-KB1-R, SEQ ID NO: 20
TGTTGACAGTGGTATTTCTGGTG

NE-KB2-F, SEQ ID NO: 21
GGCCGGAAAGACCTATCCTACT

NF-KB2-R, SEQ ID NO: 22
CTACAGACACAGCGCACACT

Il-2ra-F, SEQ ID NO: 23
AACCATAGTACCCAGTTGTCGG

| | |
|---|---|
| Il-2ra-R,<br>TCCTAAGCAACGCATATAGACCA | SEQ ID NO: 24 |
| Nras-F,<br>ACTGAGTACAAACTGGTGGTGG | SEQ ID NO: 25 |
| Nras-R,<br>TCGGTAAGAATCCTCTATGGTGG | SEQ ID NO: 26 |
| Dlgap5-F,<br>GTGTCACGTTTTGCCAGTCG | SEQ ID NO: 27 |
| Dlgap5-R,<br>TCTGTTTCGCTCATACACCCT | SEQ ID NO: 28 |
| OX40-F,<br>TACCTACCCCAGTGGTCACAA | SEQ ID NO: 29 |
| OX40-R,<br>ACGGATGACATAGAGTATCCCTG | SEQ ID NO: 30 |
| Bcl10-F,<br>ACCAACAACCTCTCTAGGTGC | SEQ ID NO: 31 |
| Bcl10-R,<br>CCCTCCGGGTGGGTACATGA | SEQ ID NO: 32 |
| IFN-γ-F,<br>ATGAACGCTACACACTGCATC | SEQ ID NO: 33 |
| IFN-γ-R,<br>CC ATCCTTTTGCCAGTTCCTC | SEQ ID NO: 34 |
| IL-12α-F,<br>CCCTTGCCCTCCTAAACCAC | SEQ ID NO: 35 |
| IL-12α-R,<br>AAGGAACCCTTAGAGTGCTTACT | SEQ ID NO: 36 |
| IL-12β-F,<br>TGGTTTGCCATCGTTTTGCTG | SEQ ID NO: 37 |
| IL-12β-R,<br>ACAGGTGAGGTTCACTGTTTCT | SEQ ID NO: 38 |
| TNF-α-F,<br>CCCTCACACTCAGATCATCTTCT | SEQ ID NO: 39 |
| TNF-α-R,<br>GCTACGACGTGGGCTACAG | SEQ ID NO: 40 |
| IL-4-F,<br>GGTCTCAACCCCCAGCTAGT | SEQ ID NO: 41 |
| IL-4-R,<br>GCCGATGATCTCTCTCAAGTGAT | SEQ ID NO: 42 |
| IL-5-F,<br>CTCTGTTGACAAGCAATGAGACG | SEQ ID NO: 43 |
| IL-5-R,<br>TCTTCAGTATGTCTAGCCCCTG | SEQ ID NO: 44 |
| IL-13-F,<br>CCTGGCTCTTGCTTGCCTT | SEQ ID NO: 45 |
| IL-13-R,<br>GGTCTTGTGTGATGTTGCTCA | SEQ ID NO: 46 |
| IL-6-F,<br>TAGTCCTTCCTACCCCAATTTCC | SEQ ID NO: 47 |
| IL-6-R,<br>TTGGTCCTTAGCCACTCCTTC | SEQ ID NO: 48 |
| IL-17-F,<br>TTTAACTCCCTTGGCGCAAAA | SEQ ID NO: 49 |
| IL-17-R,<br>CTTTCCCTCCGCATTGACAC | SEQ ID NO: 50 |

RNA Isolation, Micro-Array and RT-qPCR Analyses:

For some experiments, resting and proliferating Tregs were sorted based on cell trace violet dilution. Total RNA was isolated from these cells by using RNAeasy columns (Qiagen). The cDNA synthesized from total RNA was used for RT-qPCR analysis with Fast SYBR green master mix (Applied Biosystems) and gene specific primers by using AB ViiA7 RT-qPCR instrument (Applied Biosystems). Gene expression values were calculated by comparative Δ Ct method after normalization to GAPDH internal control and expressed as fold change over respective controls. Micro array analysis was performed in duplicate using the Affymetrix GeneChip Mouse Genome 430 2.0 microarray at Center for genomics core facility, University of Illinois at Chicago. Briefly, biotinylated cDNA was synthesized from total RNA using biotinylated dNTPs and allowed to hybridize with microarrays and scanned. Arrays which passed quality control tests were further subjected to gene expression analysis after normalization with housekeeping gene controls. Data were analyzed using the R-package software. Student's t-test was used to filter differentially expressed genes Micro array has been submitted to NCBI-Gene Expression Omnibus database and publicly available (Accession No. GSE81051).

Priming Mice with mTg and OVA:

Groups of CBA/J mice were immunized (3 mice per group for each experiment) subcutaneously with OVA (100 μg/mouse) or mTg (100 μg/mouse) emulsified in Complete Freund's Adjuvant (CFA) on day 1 and day 10. Various subsets of T cells from these mice were used in Treg expansion and proliferation assays.

Adopdve Transfer:

Three groups of 3 mice each were immunized twice, 10 days apart, with mTg (100 μg/ml) emulsified in CFA. Ten days after the $2^{nd}$ immunization, mice received i.v. injection of either i) PBS, ii) $2 \times 10^6$ purified CD11c DCs from untreated CBA/J mice or iii) $2 \times 10^6$ CD11c GM-BMDC purified and sorted from BM cultures. Two identical adoptive transfers were done for each group at 5 day intervals. Five-days after the 2° transfer, mice were sacrificed and spleen and thyroid draining lymph node cells were analyzed for Treg percentages.

Animal Experiments:

Six week old female NOD mice were divided into two groups each containing 13 mice. Mice were injected (i.p) with recombinant OX40 L (200 µg) and JAG1 (200 µg) on weeks 10, 11 and 12. Age and sex matched control mice received PBS. All the reagents used for animal experiments were endotoxin free (<0.1 EU/ml) when tested by using Pierce endotoxin quantification kit (Thermo scientific). Blood glucose levels were monitored weekly from week 9 to 28. On week 15, three mice from each group were sacrificed and analyzed for Treg cell numbers. At the end of week 28, all animals were sacrificed and tissue sections of pancreas were subjected to histopathological examination to determine lymphocyte infiltration and β-cell destruction.

Histopathology and Immunohistochemistry:

Pancreatic tissues from control and OX40L-JAG1 treated NOD mice were excised and fixed in 10% formalin overnight. Tissues were processed and stained with hematoxylin and eosin. Images captured in Aperio digital image scanner were analyzed with Aperio Image-scope viewer. Insulitis was scored independently by three individuals with the following scoring scheme: 0—no insulitis, 1—peri-islet insulitis, 2—intermediate insulitis, 3-intraislet insulitis, 4—complete islet insulitis67. For immunohistochemistry, sections were stained with anti-Insulin antibody (Abcam, MA), followed by TRITC-conjugated anti-guinea pig IgG Abs (T7153) and DAPI (D9542) purchased from Sigma-Aldrich (St. Louis, MO) and subjected to confocal microscopy (Zeiss Laser Scanning Microscope; LSM 710).

Statistical Analysis:

Mean, standard deviation, and statistical significance were calculated using the Graph pad software and MS-Excel application software. In some experiments, statistical analyses were performed using Prism GraphPad (V6.0). Data were expressed as Mean±SEM of multiple experiments. Paired Student's t-test was used to compare two groups, whereas ANOVA with multiple comparisons was used to compare more than two groups. Differences in the frequency of hyperglycemia were determined by Kaplan-Meier survival analysis using the log-rank test. Statistical significance was determined using the one tailed Students t-test. A p value ≤0.05 was considered as significant.

Example 1: OX40L is Necessary but not Sufficient for the Expansion of Tregs Mediated by GM-BMDC A blocking antibody against OX40L demonstrated a dose-dependent abrogation of Treg proliferation by GM-BMDC (8), which was restored upon addition of a soluble OX40 agonist. In a typical 7-day bone marrow culture with GM-CSF, ~30% CD11c$^+$GM-BMDCs were OX40L$^+$ (FIG. 1A). To determine if OX40L-induced signaling was sufficient for the expansion of Tregs, co-cultures with sorted populations of OX40L$^+$ and OX40L$^-$ GM-BMDCs with naive CD4$^+$ T-cells were established. Only OX40L$^+$ GM-BMDC drove the proliferation of Foxp3$^+$ Tregs (10.1±0.6%) relative to OX40L$^-$ GM-BMDC (0.5±0.1%, p=0.002) (FIG. 1B).

To specifically address the role of OX40L$^+$ GM-BMDCs on Foxp3$^+$ Tregs, Foxp3-GFP transgenic mice were used. Co-cultures of sorted OX40L$^+$ and OX40L$^-$ GM-BMDCs (FIG. 1) with sorted and Cell-Trace Violet labelled CD4$^+$GFP$^+$ (FIG. 1C) or CD4$^+$GFP$^-$ (FIG. 1D) T cells isolated from Foxp3-GFP mice (FIG. 1), in the presence or absence of IL-2 were established. The extent of Cell-Trace Violet dilution revealed that in the absence of IL-2, a very small fraction of GFP$^+$ T-cells proliferated after 5-days of co-culture with either total, OX40L$^+$ or OX40L$^-$ GM-BMDCs. However, in the presence of IL-2, Foxp3+ T-cells proliferated efficiently only when co-cultured with either total (25.0±1.7%) or OX40L$^+$ (34±3.2%), and not with OX40L$^-$, GM-BMDCs (7.4±1.0%). In contrast, GFP$^-$ T-cells (Foxp3$^-$) showed either modest or robust proliferation based on absence or presence of IL-2 irrespective of whether they were co-cultured in the presence of total, OX40L$^+$ or OX40L$^-$ GM-BMDCs. Most notably, there was not any adaptive conversion of Teff into Tregs in any cultures involving GFP– cells. It is important to note that none of these co-cultures were stimulated with anti-CD3 or any exogenous antigen. Thus, the data strongly suggested that only OX40L$^+$ GM-BMDCs can cause efficient proliferation Foxp3+ Tregs.

To determine if signaling by OX40L alone was sufficient to expand Tregs, CD4 T cells co-cultured with either OX40L$^-$ GM-BMDC or splenic DCs were supplemented with a functional OX40 agonist. Such a treatment failed to cause significant proliferation of Foxp3$^+$ Tregs (0.8±0.1%) when compared to the Treg proliferation noted in the presence of OX40L$^+$ GM-BMDC (13.5±0.7%, p<0.001) (FIG. 1E). These results suggested that OX40L, although required, may not be sufficient for the GM-BMDC mediated ex vivo expansion of Tregs.

Figure 2:
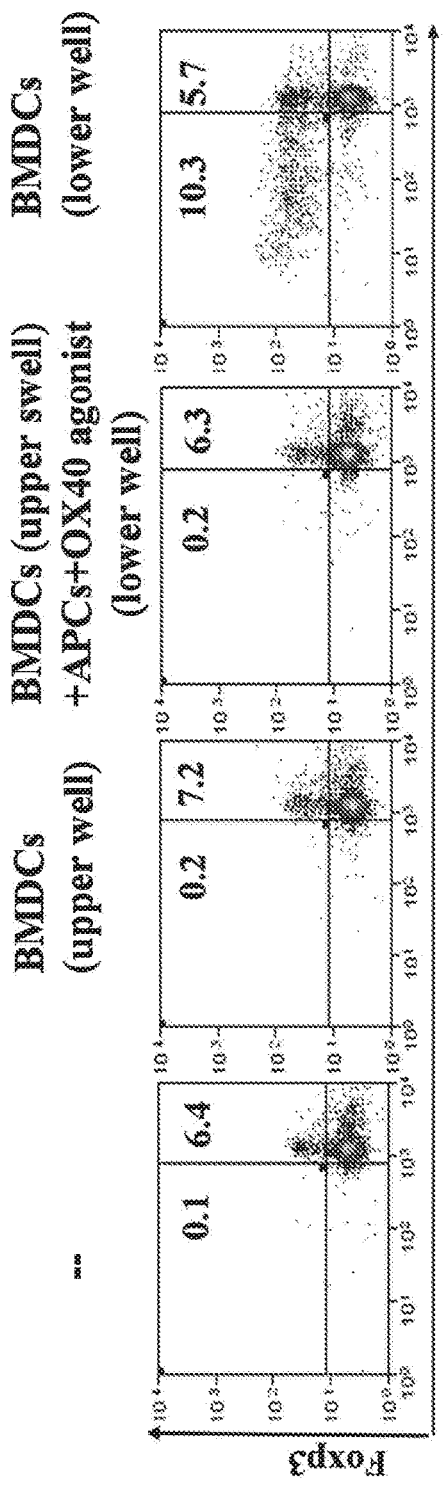
FIG. 2. OX40L is necessary but not sufficient in GM-BMDC mediated Treg expansion. (A) CD4⁺ cells from naïve mice were co-cultured with wild type GM-BMDCs either together or in transwells in which the T-cells were exposed to only the BM supernatant; in some cases the T-cells were supplemented with SpDCs and an OX40 agonist. Data were analyzed by FACS. (B) GM-BMDCs from CD80, CD86 and CD80/86 deficient mice were co-cultured with naïve CFSE labelled CD4⁺ T-cells without exogenous antigen and analyzed by FACS (lower panel). Experiments shown in Figures A and B were repeated three times with similar results.
Figure 2:
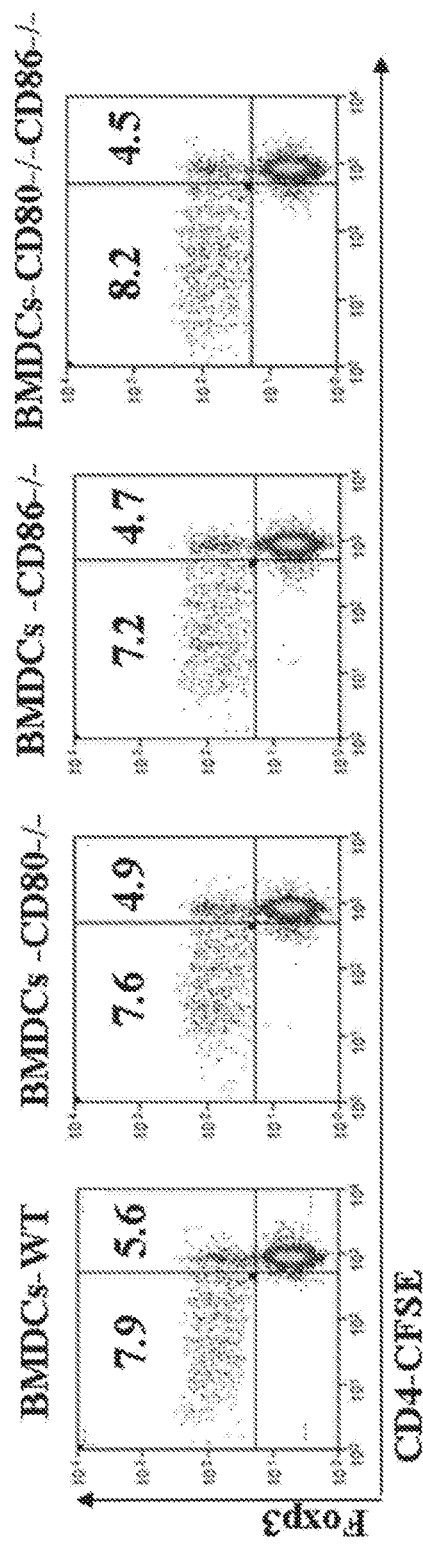

Example 2: Surface Bound Ligands Other than the B7 Family Co-Stimulatory Molecules are Involved in GM-BMDC Induced Treg Expansion Co-cultures of CD4$^+$ T-cells and DCs in trans-well plates were established to determine if, in addition to OX40L expressed on GM-BMDC, co-signaling by a soluble factor from, or a surface bound molecule on, GM-BMDC is required for Treg expansion. Splenic APCs and CD4$^+$ T-cells along with an OX40 agonist were physically separated from GM-BMDC cultured in trans-wells, which allowed for free exchange of soluble factors in culture medium. If soluble factors from GM-BMDC were contributing to Treg expansion, those factors would be expected to cross the trans-well barrier and aid in Treg expansion in the presence of OX40 agonist and splenic APCs. However, there was little or no proliferation of Tregs (0.20.1%) in the trans-well when compared to CD4+T-cell-GM-BMDC co-cultures (10.3±0.7%) (FIG. 2A). These results suggested that in addition to OX40L, co-signaling by other GM-BMDC surface bound molecule(s) was essential for GM-BMDC mediated Treg expansion.

To identify other cell surface molecule(s) involved in GM-BMDC mediated Treg proliferation, naive CD4+ T-cells were co-cultured with GM-BMDC derived from CD80 and CD86 knockout mice. Lack of expression of either CD80 or CD86 on GM-BMDC had little or no effect on their ability to induce Treg proliferation (7.6±1.0% and 7.2±0.8%) relative to GM-BMDC derived from WT mice (7.9±0.6%) (FIG. 2B). In fact, GM-BMDC developed ex vivo from CD80/CD86 double knock-out mice could cause robust Treg proliferation in co-cultures (8.1±0.9%). These data strongly suggested that a molecule(s) other than CD80 or CD86 was involved in signaling required for the GM-BMDC induced Treg expansion.

Figure 3:
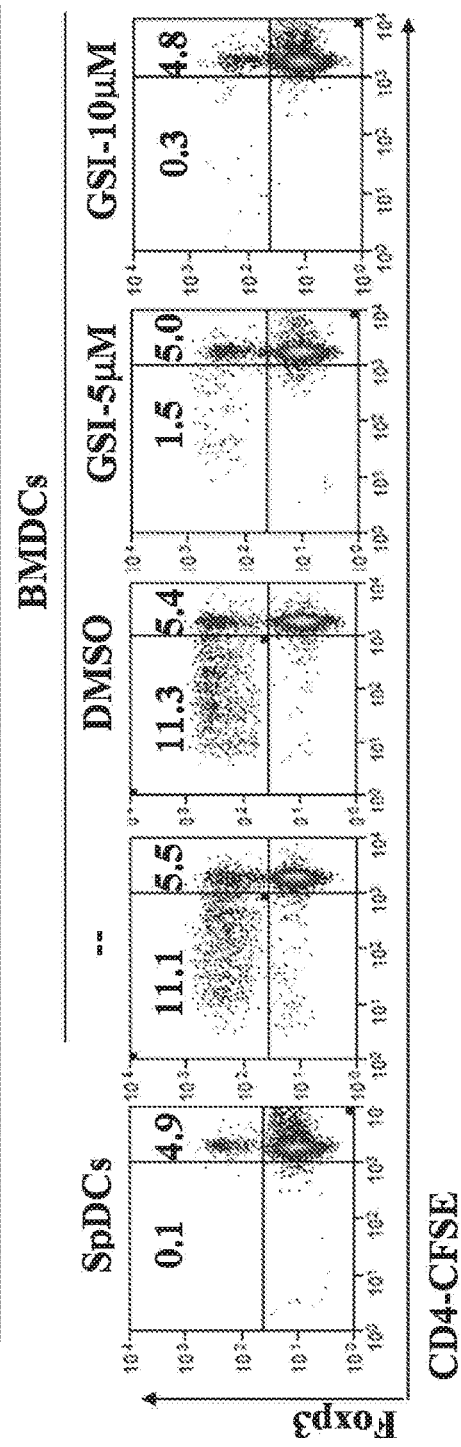
FIG. 3. Jagged-1 mediated Notch signaling is required for Treg expansion by GM-BMDCs. (A) Co-cultures of GM-BMDCs with CFSE labelled CD4⁺ T-cells were supplemented with Gamma-secretase-inhibitor (GSI), an inhibitor of Notch signaling, and analyzed by FACS. (B) Summary of FACS data from Propidium Iodide staining of co-cultures from GSI experiment showing little or no cell necrosis in all co-cultures. (C) Phenotypic characterization of CD11c⁺ SpDCs and GM-BMDCs comparing the levels of expression of different Notch ligands. Cells were gated on the CD11c⁺ populations. (D) Co-cultures of GM-BMDCs with CFSE labelled CD4⁺ T-cells were supplemented with two concentrations of a Jagged-1 neutralizing antibody and analyzed by FACS. Experiments shown in Figures A through D were repeated three times with similar results.
Figure 3:
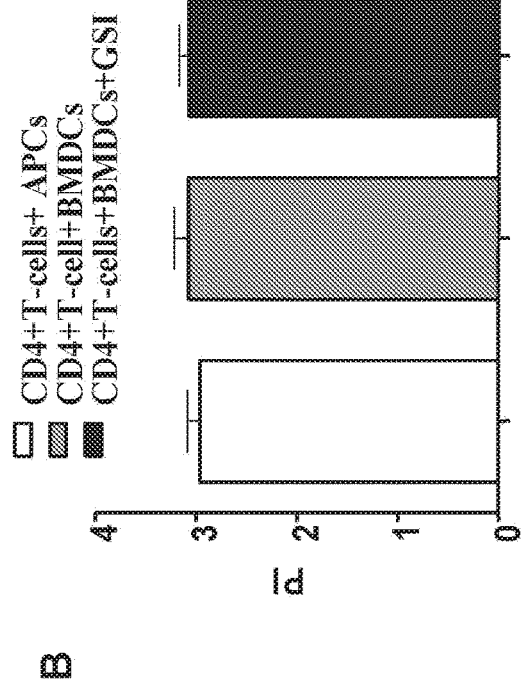
Figure 3:
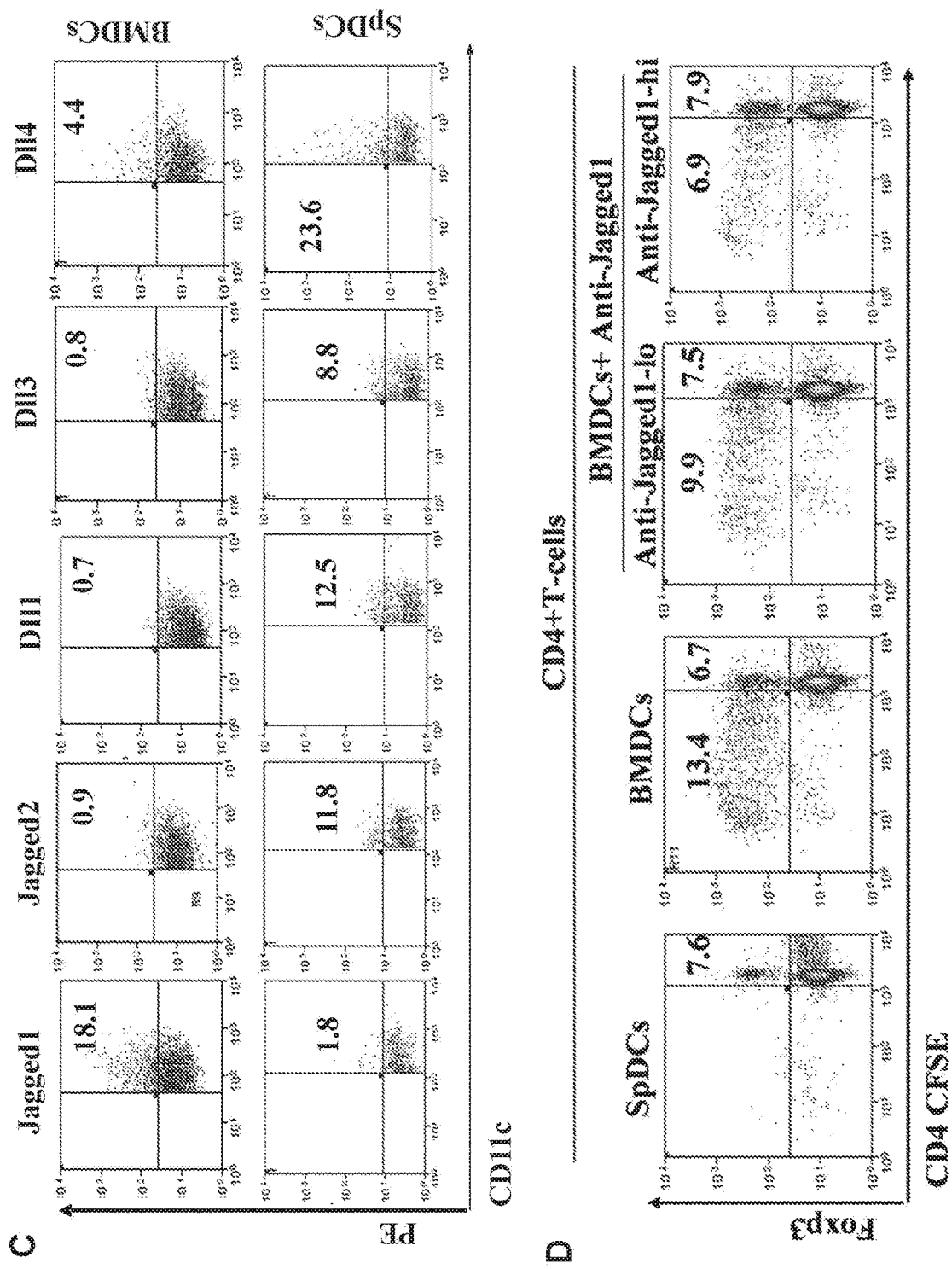
Figure 8:
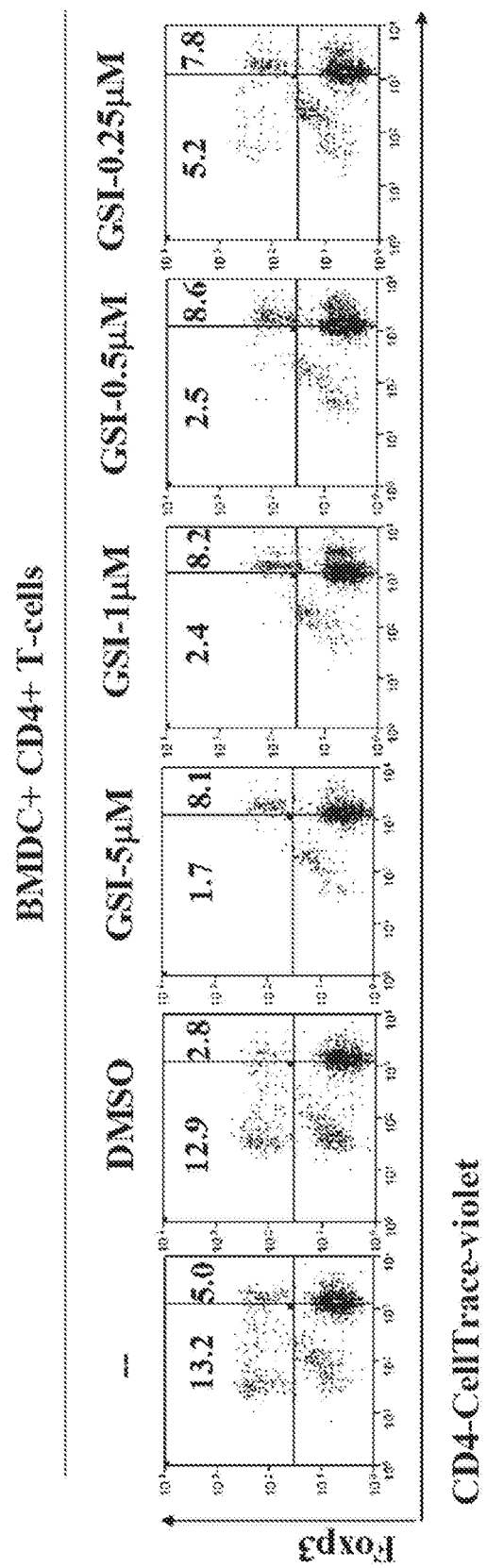
FIG. 8. Inhibition of Notch signaling abrogates GM-BMDC mediated Treg proliferation. Co-cultures of BMDCs with Cell Trace-violet labelled CD4⁺ T-cells were supplemented with R04929097, a Gamma-secretase-inhibitor (GSI), in different concentrations and analyzed by FACS. The inhibition of the Notch signaling by the GSI resulted in abrogated GM-BMDC mediated Treg proliferation.

Example 3: Jagged-1 Mediated Notch Signaling is Involved in GM-BMDC Induced Proliferation of Foxp3$^+$ Tregs To test whether Notch signaling was involved in ex vivo Treg proliferation, S-2188, a γ-secretase inhibitor (GSI) that blocks Notch signaling was added to the GM-BMDC/T-cell co-cultures. Blocking Notch signaling with S-2188 completely abrogated Treg proliferation (1.5±0.3%-0.3±0.1%) in a dose dependent manner (5-10 µM) compared to proliferation of Tregs in untreated cultures (11.1±1.0%, p<0.001) (FIG. 3A). To assess whether this difference in cell viability, co-cultures were stained with propidium iodide (PI) and analyzed by FACS for cell death; S-2188 treatment did not affect cell survival (FIG. 3B). The effect of treating the cells with R04929097, another GSI known to be effective at lower doses, at different concentrations (250 nM-5 µM) (FIG. 8) was also tested. While co-cultures of CD4+ T-cells with GM-BMDCs alone resulted in robust proliferation (~13.2±0.4%), treatment with GSI severely restricted proliferation in a dose dependent manner (e.g., 1.7±0.3% at 5 µM; and 5.2±0.4% at 250 nM GS1). These results suggested that Notch signaling was important for GM-BMDC mediated Treg proliferation. Subsequently, GM-BMDC and SpDCs were stained to analyze for the expression of different Notch ligands. A much higher proportion of GM-BMDC expressed Jagged-1 (18.1±2.8%, p<0.01) relative to SpDCs (1.8±0.5%) (FIG. 3C). In contrast, all other Notch ligands (Jagged-2, DLL1, DLL3 and DLL4) were expressed on a higher percentage of SpDCs than on GM-BMDC. Addition of a blocking antibody against Jagged-1 (lo=10 µg/ml; hi=20 µg/ml) suppressed Treg expansion in a dose dependent manner (reduced from 13.4%±1% to 9.9%±0.5% with low dose and to 6.9±0.2% with high dose (p<0.01 in all instances) (FIG. 3D). Jagged-1 blocking antibody had little or no effect on the percentages of non-dividing Tregs (~7-8%) and indicated that the effect of Jagged-1 blockage primarily affected Treg proliferation without affecting their survival.

Example 4: Jagged-1 and OX40L are Critical for GM-BMDC Mediated Treg-Expansion

Figure 4:
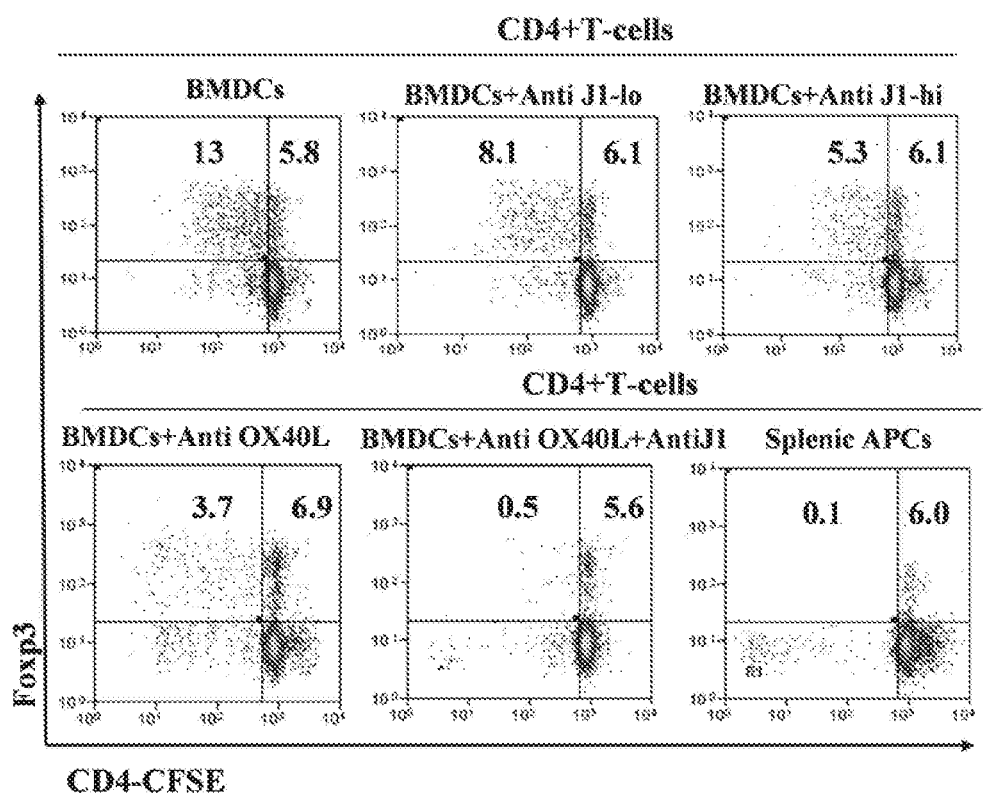
FIG. 4. OX40L and Jagged-1 function are critical for GM-BMDC mediated expansion of Tregs (A) Co-cultures of GM-BMDCs with CFSE labelled CD4⁺ T-cells were supplemented with neutralizing antibodies to Jagged-1 and OX40L, either alone or in combination and analyzed by FACS. (B) FACS analysis of CD25⁺ Foxp3⁺ T-cells from the co-cultures of APCs and MHCII⁻/⁻ GM-BMDCs with CD25⁺ T-cells in the presence and absence of IL-2 and neutralizing antibodies to OX40L and Jagged-1. (C) GM-BMDCs were treated with control or Jagged-1 specific siRNAs. FACS analyses of cell surface expression of Jagged-1 and OX40L showed specific inhibition of Jagged-1, but not OX40L, after Jagged-1 specific siRNA treatment. (D) CFSE labelled CD4⁺ T-cells were cultured with control or Jagged-1 specific siRNA treated GM-BMDC in the presence or absence of anti-OX40L antibodies. Results shown in Figures A through D are representative of 3 independent experiments.
Figure 4:
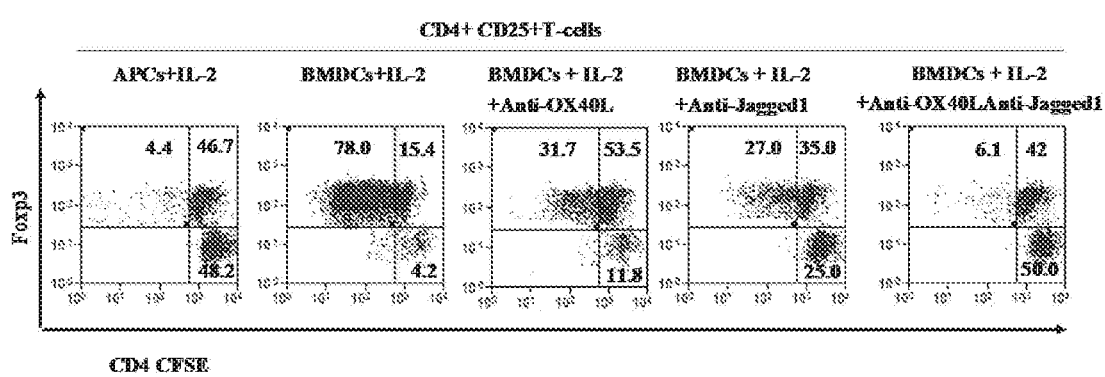
Figure 4:
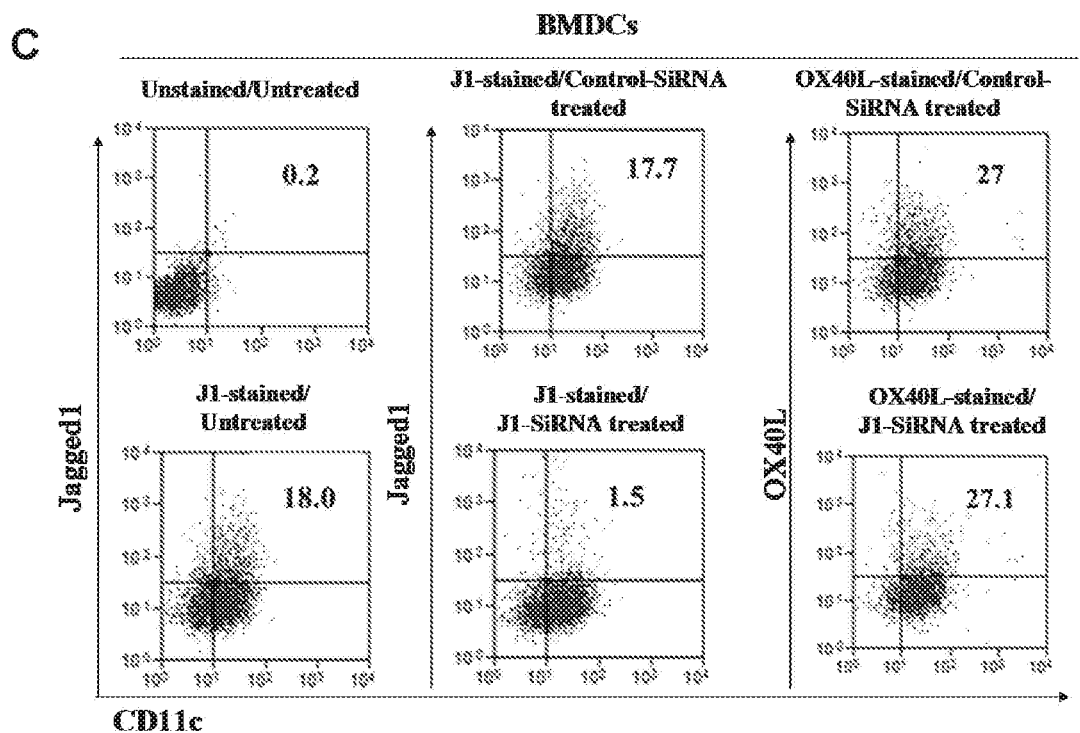
Figure 4:
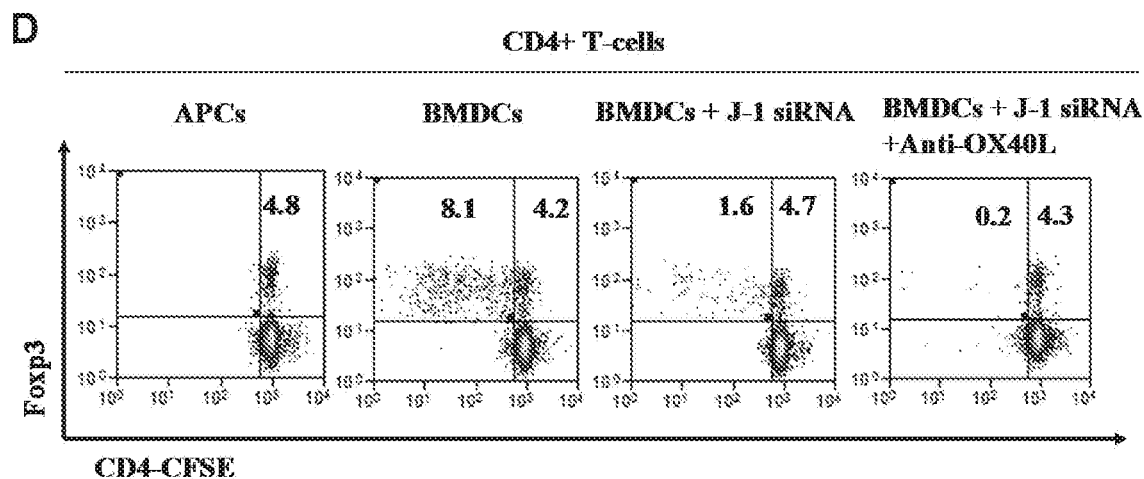

Specific antibodies to block OX40L and Jagged-1 were used to determine whether concurrent signaling by both ligands was essential for Treg expansion. Blocking either OX40L or Jagged-, using specific antibodies, reduced Treg proliferation from 13.0% in the absence of antibody to 5.3±0.3% and 3.7±0.2% in the presence of anti-Jagged-1-Hi and anti-OX40L-Hi respectively. However, simultaneous blockade of both molecules completely prevented the GM-BMDC mediated Treg proliferation (13.0% v/s 0.5%±0.1%, p<0.01) (FIG. 4A). These data suggested that Notch signaling, likely induced by Jagged-1, along with OX40 signaling induced by OX40L were essential for GM-BMDC mediated Treg proliferation.

OX40L-mediated Treg expansion by GM-BMDC did not require TCR stimulation (8). To determine if the Jagged-1 mediated signaling was also independent of TCR signaling, CD25+ T cells were co-cultured with GM-BMDCs derived from MHC class-II$^{-/-}$ mice in the presence of IL-2. MHC GM-BMDCs were able to expand Tregs (78.0±1.4%). However, blocking either OX40L or Jagged-1 significantly reduced Treg proliferation from 78.0±1.4% to 31.7±0.5% in the presence of anti-OX40L and to 27.0±1.1% in the presence of anti-Jagged-1. Blocking both ligands almost completely prevented Treg proliferation (p<0.01 in all instances) (FIG. 4B).

To further substantiate the relative importance of these two ligands, specific siRNA was used to knock down Jagged-1 (FIG. 4C) on GM-BMDC co-cultured with CD4+T cells. siRNA treatment (120 nM) significantly reduced expression of Jagged-1 in GM-BMDC (1.5±0.4%; p<0.01) relative to its expression on either untreated (18.0±2.1%) or control si RNA treated (17.7±2.4%) GM-BMDC, without altering expression of OX40L (approximately 27% in both Jagged-1 siRNA treated and control siRNA treated cells) (FIG. 4C, right panels). These GM-BMDCs were used in co-culture with CFSE-labelled naive CD4+T-cells. Treg proliferation was significantly reduced from 8.1±1.0% in the presence of control GM-BMDC to 1.6±0.5% in the presence of Jagged-1 knocked down GM-BMDC (FIG. 4D). Combined treatment of GM-BMDC with an OX40L blocking antibody (hi=10 µg/ml) along with Jagged-1 inhibition almost completely abrogated their ability to expand Tregs (0.2±0.1%). These results clearly showed that both OX40L and Jagged-1 expressed on GM-BMDC were required for efficient Treg expansion.

Figure 5:
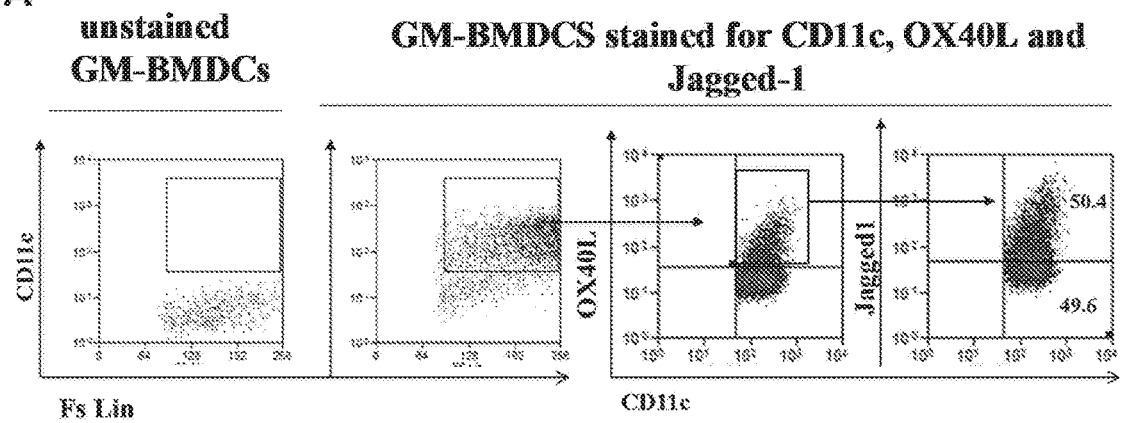
FIG. 5. OX40L/Jagged-1 co-signaling is required for GM-BMDC mediated Treg expansion. (A) GM-BMDCs were analyzed for surface expression of OX40L and Jagged-1. Cells were successively gated over the CD11c⁺ and OX40L⁺ populations and analyzed for Jagged-1 expression. (B) CFSE labelled CD4' T-cells were co-cultured with either total or OX40L⁺ Jagged-1⁺ or OX40L⁺ Jagged-1⁻ GM-BMDCs. Some cultures were supplemented with anti-OX40L and/or anti-Jagged-1 antibodies. The Figure shows summary of cell proliferation data analyzed by FACS. The experiment was repeated three times with similar results.
Figure 5:
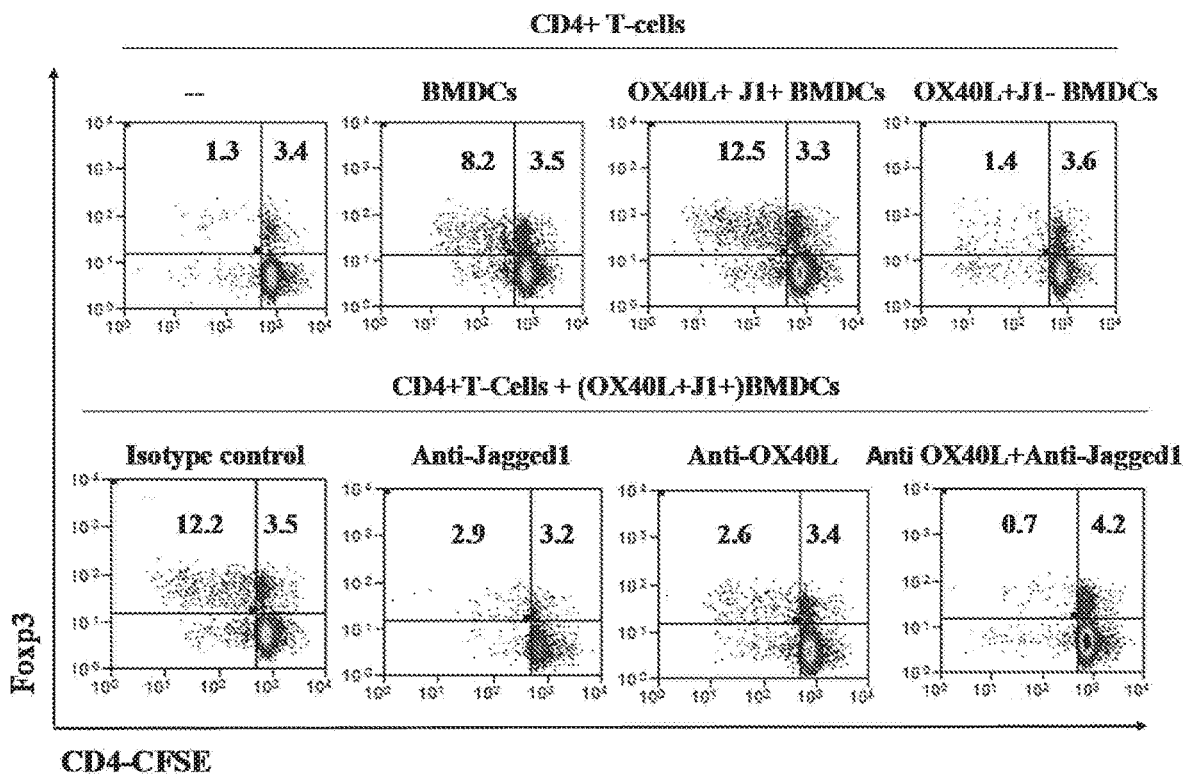

Example 5: OX40L and Jagged-1 Mediated Co-Signaling is Required for GM-BMDC Mediated Tree Expansion GM-BMDCs that were OX40L$^-$ were also Jagged-1$^-$ (FIG. 5A). On the other hand, about half of OX40L$^+$ GM-BMDCs were Jagged-1$^+$ (50.3±0.5%, p<0.02) (FIG. 5A).

To determine if OX40L and Jagged-1 co-expression was required for OX40L$^+$ GM-BMDC-induced expansion of Tregs, the GM-BMDC were sorted into OX40L$^+$ Jagged-1$^+$ and OX40L$^+$ Jagged-1$^-$DCs and used them in co-culture with naive CD4$^+$ cells. While total GM-BMDC could induce Treg proliferation (e.g., 8.2%), the OX40L$^+$ Jagged-1$^+$ GM-BMDCs were able to more efficiently expand Tregs (12.5±0.2%). In contrast, OX40L$^+$ Jagged-1 failed to mediate significant expansion of Tregs (1.40.1%, p<0.001) (FIG. 5B). Blocking either ligand with the corresponding blocking antibody caused significant reduction in Treg expansion. However, blocking both ligands (anti-OX40L=10 g/ml, anti-Jagged-1=20 µg/ml) on OX40L$^+$ Jagged-1$^+$ GM-BMDCs abrogated Treg expansion (reduced from 12.5±0.2% to 0.7±0.1%; p<0.01). These results clearly demonstrated that GM-BMDC mediated ex vivo Treg expansion required cell surface expression of both OX40L and Jagged-1.

Example 6: GM-BMDC Associated Jagged-1 can Induce Treg Proliferation by Activating Tree Associated Notch3

Figure 6:
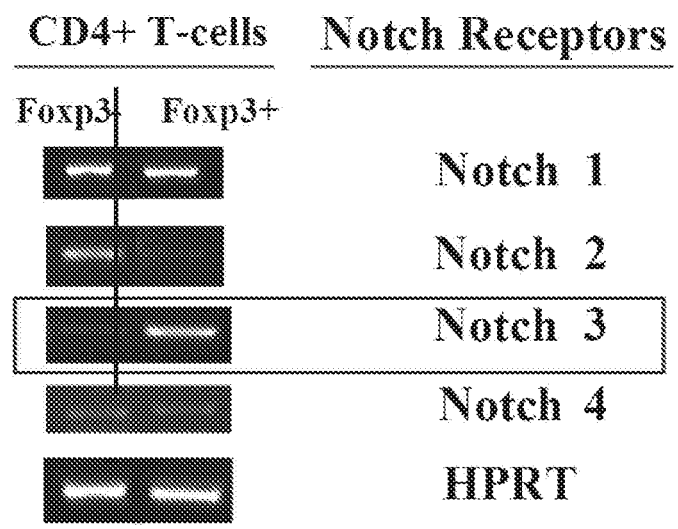
FIG. 6. GM-BMDCs expressing Jagged-1 transduce proliferation signals to Tregs through Notch 3. (A) GFP⁺ and GFP⁻ cells isolated from Foxp3-GFP mice were analyzed for the expression of Notch receptor transcripts by RT-PCR. A Notch 3 transcript was detected specifically in Tregs. cDNAs from different T-cell populations were subjected to PCR using different Notch specific primers and analyzed on 2% agarose gel. Parts of the gel relevant to the specific subpopulation were assembled together. (B) Co-culture of GM-BMDCs and CD4⁺ T-cells in the presence of neutralizing antibody to Notch 3 or Notch 1. Each scatter plot in Figure B and Figure C represents five separate experiments. (C) Shows Notch 3 specific Notch Intracellular Domain (NICD) only in proliferating Foxp3⁺ T-cells in GM-BMDC/T-cell co-cultures analyzed by FACS. CFSE dilution was used to measure cell-proliferation and cells were gated on CFSE diluted or undiluted populations and analyzed for NICD.
Figure 6:
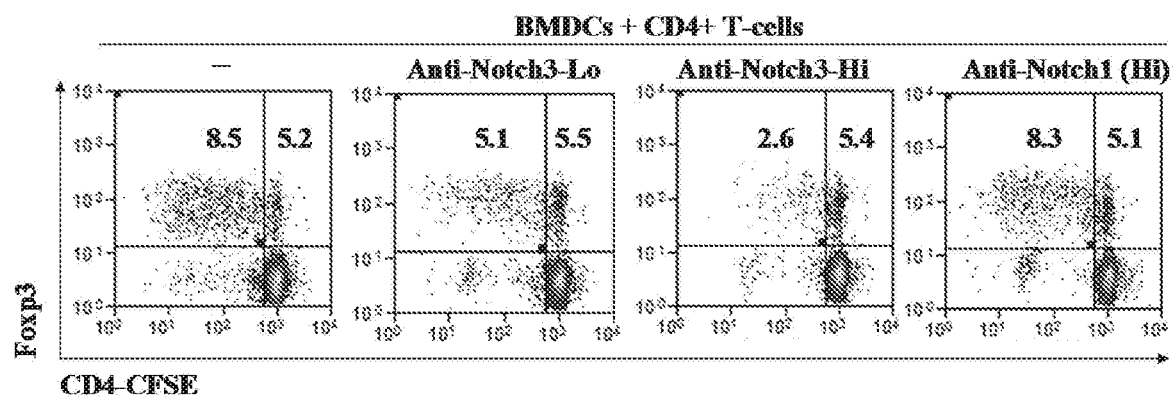
Figure 6:
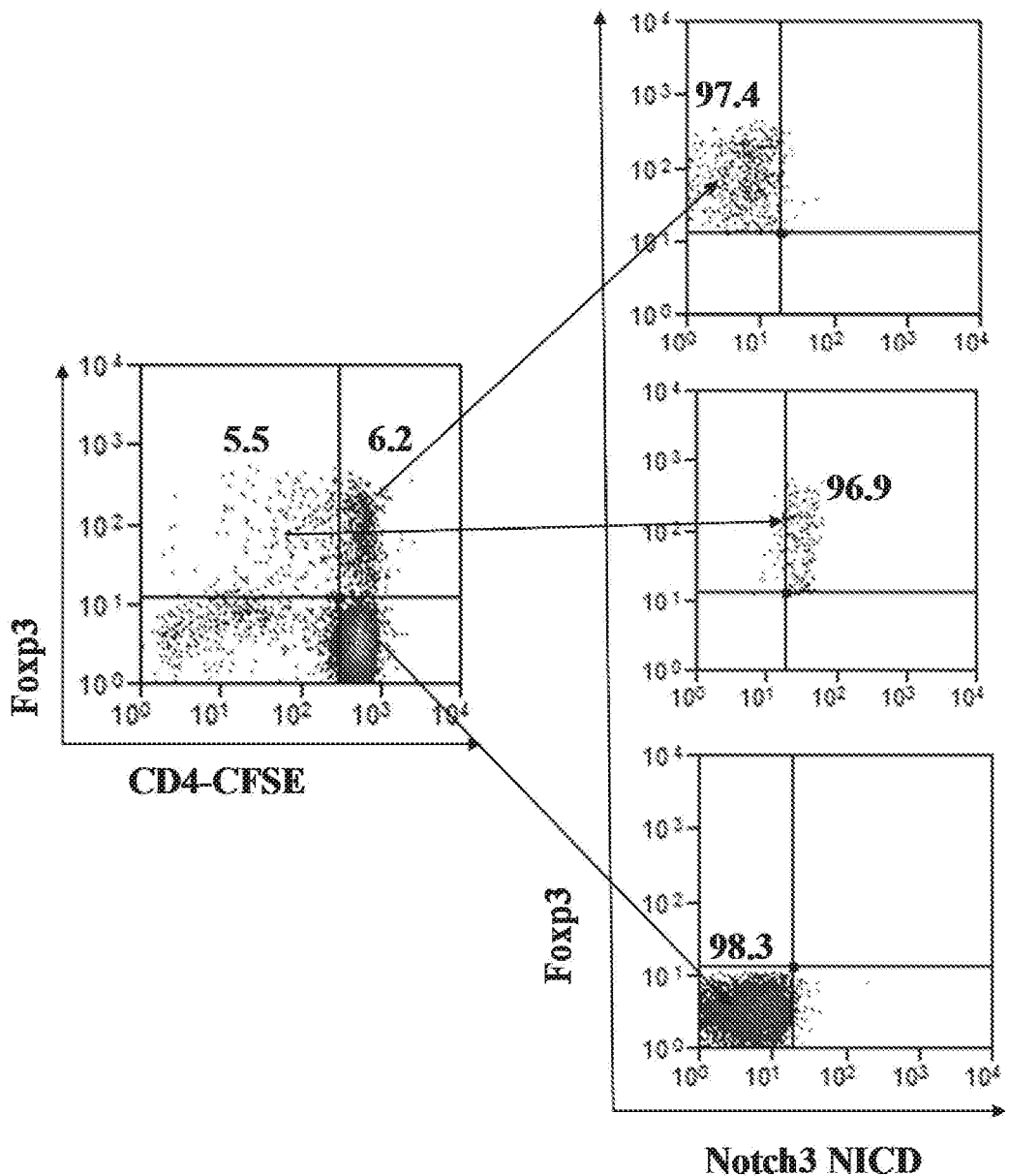

To determine the specific Notch receptor that was activated by Jagged-1 to cause Treg proliferation, mRNA expression patterns of all four Notch receptors in Foxp3$^+$ (i.e. GFP$^+$) and Foxp3$^-$ (GFP$^-$) cells from Foxp3-GFP mice were analyzed. Semi-quantitative PCR indicated that transcripts for Notch 1 and Notch 4 were similarly expressed in Teffs and Tregs. However, expression of Notch 3 transcript was significantly higher in Foxp3$^+$ Tregs relative to Foxp3$^-$ effector T cells, while the transcripts for Notch 2 was predominantly expressed in Teff cells (FIG. 6A). These findings suggested that Jagged-1 expressed on GM-BMDC may be binding specifically to Notch 3 expressed on Tregs to cause their expansion.

The importance of Notch 3 signaling was substantiated by a reduction in GM-BMDC induced Treg proliferation upon addition of a Notch 3 blocking antibody to the GM-BMDC-T cell co-culture in a dose dependent manner. The proliferation was reduced from 8.5±0.3% in untreated culture to 5.1±0.4% and 2.6±0.2% in the presence of low (10 µg) and high dose (20 µg) of anti-Notch3 antibody respectively: p<0.02 (FIG. 6B). In contrast, a blocking antibody to Notch 1 did not have any apparent effect on Treg proliferation.

Detection of cytoplasmic Notch Intra-Cellular Domain (NICD) has been used as a marker for activated Notch 3 (24). To confirm the role of Notch 3 in mediating Jagged-1 induced signaling, a Notch 3 specific polyclonal antibody (12, 21) was used to detect the intracellular portion of Notch 3 in the GM-BMDC/T-cell co-cultures. Analyses of proliferating and non-proliferating Foxp3$^+$ and Foxp3$^-$ cells showed that nearly 97% of the proliferating Foxp3$^+$ T cells were positive for Notch 3 NICD, while approximately 98% of non-proliferating Foxp3$^+$ or Foxp3$^-$ T cells were negative for Notch 3 NICD (FIG. 6C). Collectively, the data suggested that Notch 3, expressed selectively on Tregs, is activated by Jagged-1 expressed on GM-BMDCs and this interaction is essential for Treg proliferation.

Figure 13:
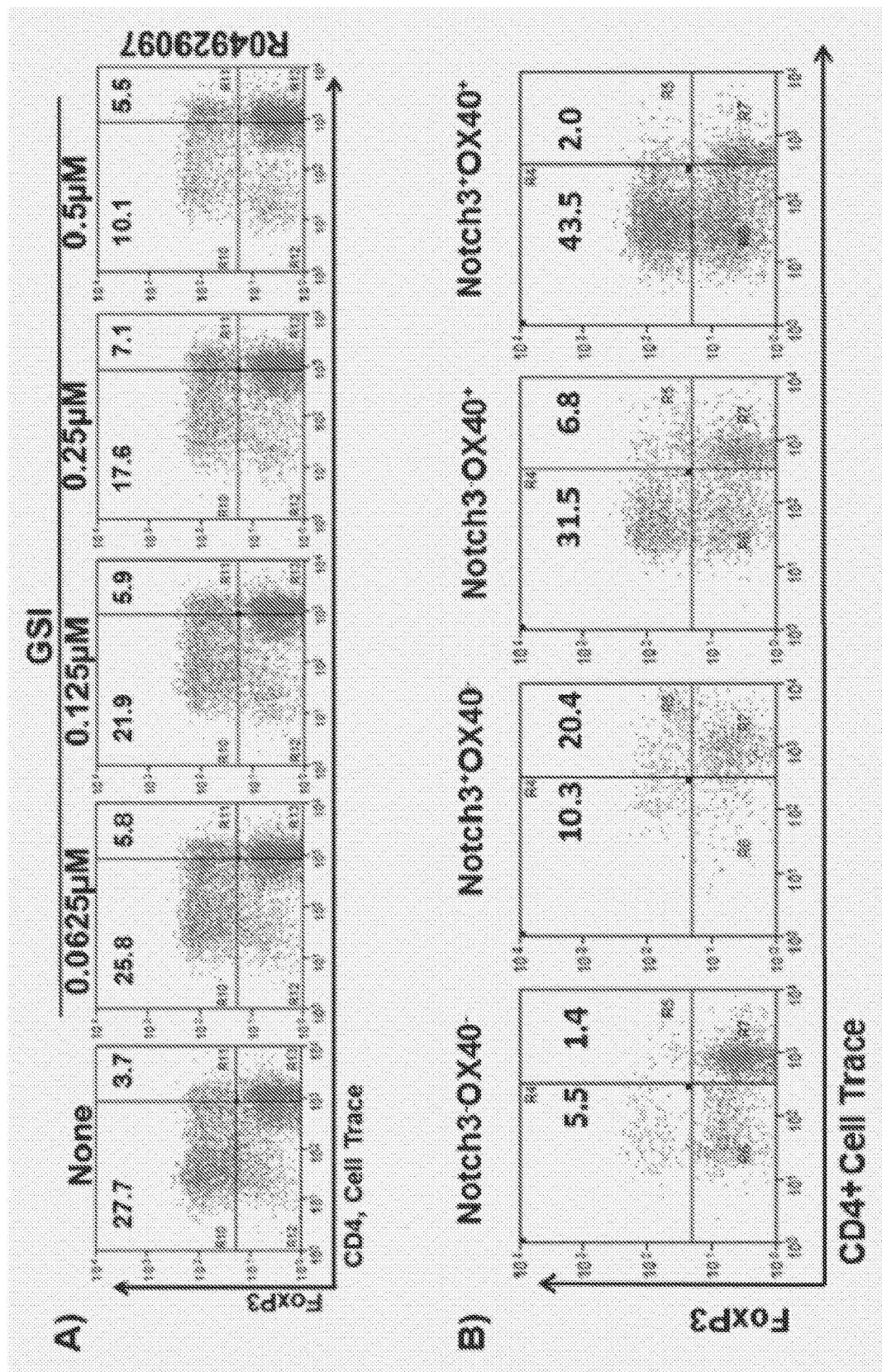
FIG. 13. CD4+ T-cells with treated with γ-secretase inhibited Notch signaling in a dose-dependent manner. (A) CD4+ T-cells from NOD mice were treated with γ-secretase inhibitor (GSI)-R042929097 at indicated concentrations and then co-cultured with G-BMDCs for 5 days. Extent of proliferation was measured by flow cytometry (n=3). (B) Notch3-OX40-, Notch3+OX40L-, Notch3-OX40+, Notch3+OX40+ subsets of $CD4^+CD25^+$ Treg cells sorted out and co-cultured with G-BMDCs for 5 days and extent of proliferation was analyzed (n=2).
Figure 14:
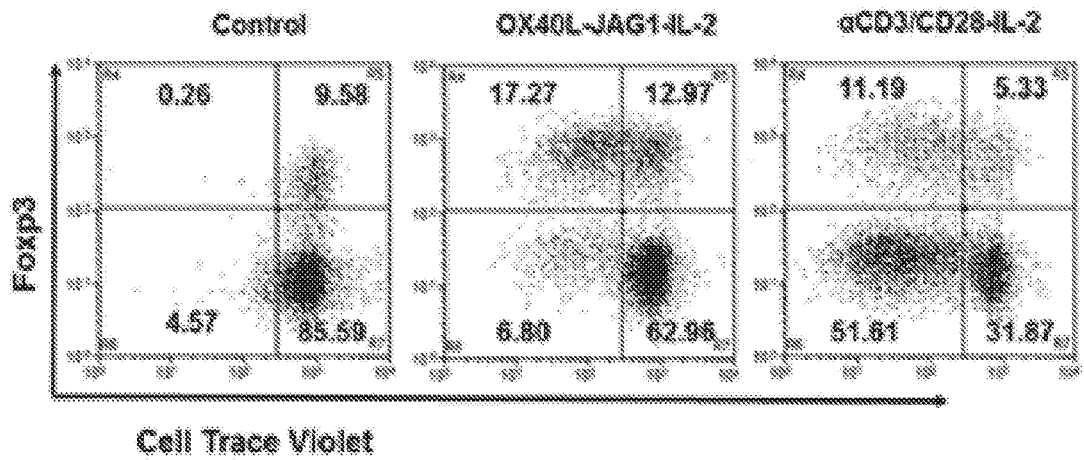
FIG. 14. Soluble OX40L-JAG1 can cause selective Treg proliferation independent of TCR stimulation. (A) $CD4^+$ T-cells were treated with IL-2 (Control), OX40L-JAG1-IL-2 and anti-CD3/CD28-IL-2 for 3 days. Extent of CD4+ Foxp3- (Teff) and CD4+ Foxp3+ (Treg) cell proliferation was analyzed by flow cytometry. (B) From the above experiments, percentages of CD25, CD44 and CD69 expressing Teff (Grey) and Treg (Black) cells were gated and indicated as numerical. (CD) Bar graph showing percentages of Teff cells and Treg cells expressing CD25, CD44 and CD69. Values are expressed as Mean±SEM (n=3; *p<0.05, p<0.01, *p<0.001 Vs control).
Figure 14:
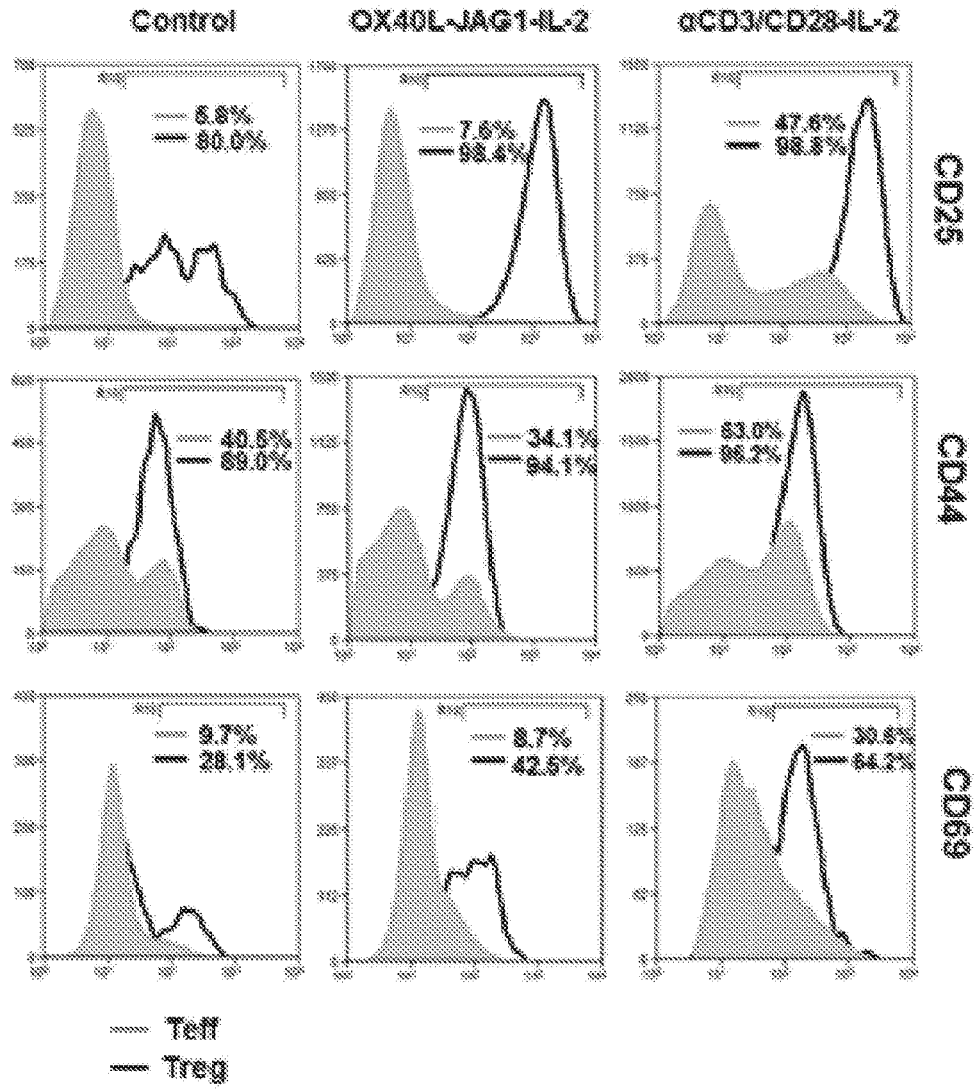
Figure 14:
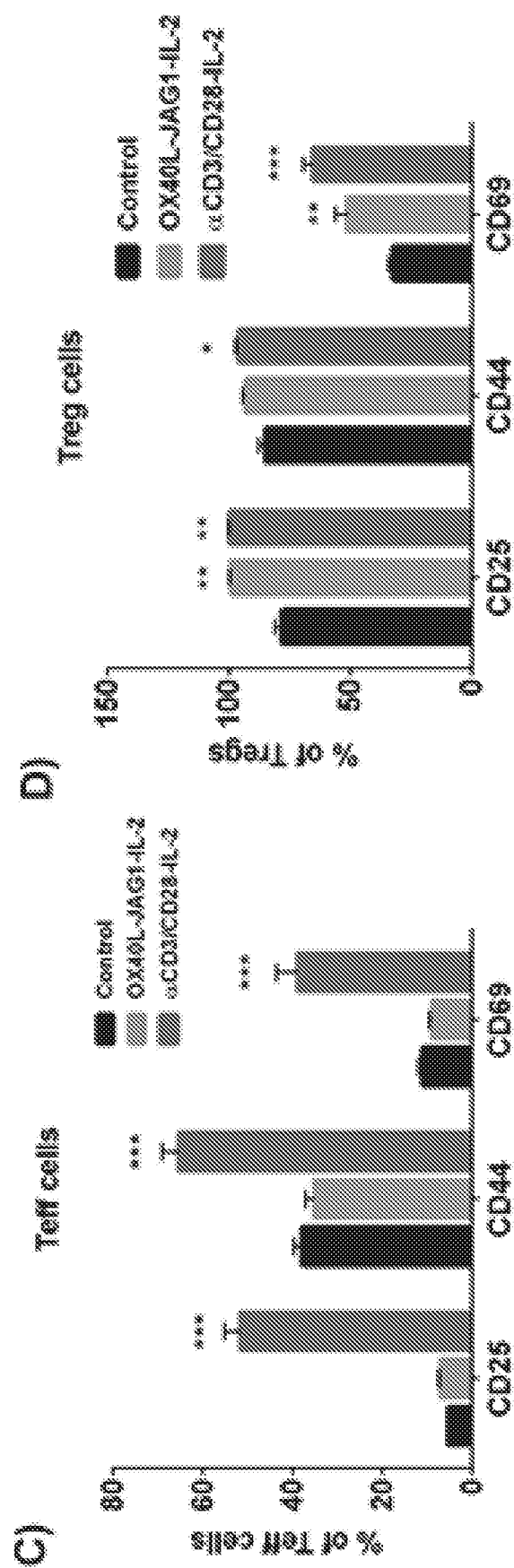
Figure 15:
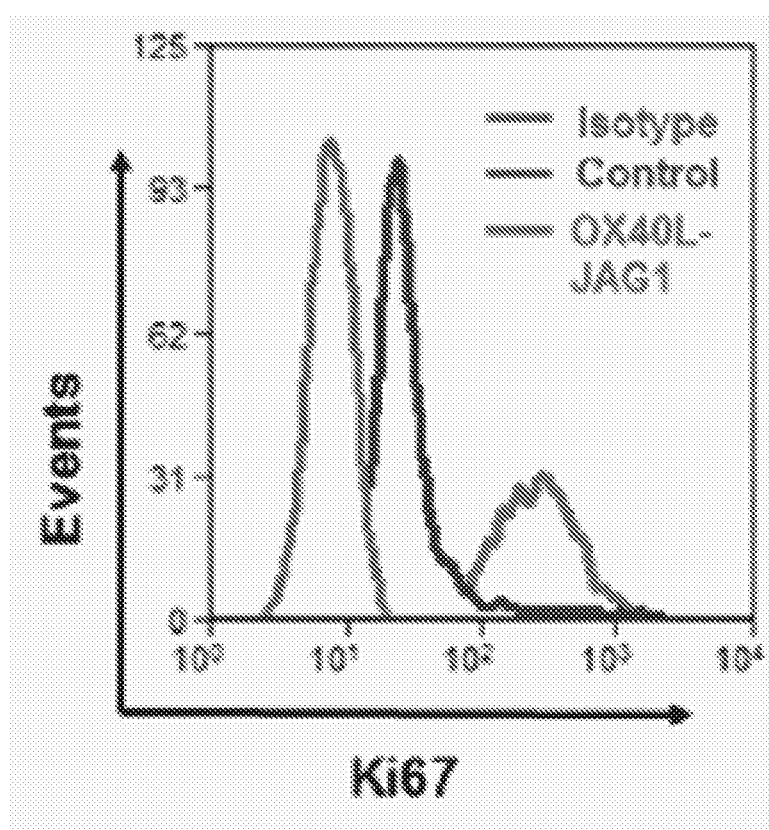
FIG. 15. Soluble OX40L-JAG1 is sufficient to cause Treg proliferation independent of TCR stimulation in an IL-2 dependent manner. Histograms showing percentage of Ki67+ Foxp3+ Tregs in cells treated with IL-2 alone (control—dashed line) or OX40L-Jag1-IL-2 (black). Grey shaded curves indicate staining with isotype-matched control antibody.

As shown in FIG. 13A, dose-dependent inhibition of Treg proliferation was identified, indicating the critical role of Notch signaling. Among the various Notch receptors, Notch3 is preferentially over-expressed on Tregs when compared to Teff cells (68). Therefore, CD4$^+$CD25$^+$ Tregs from NOD mice were sorted for Notch3$^-$OX40$^-$, Notch3$^+$OX40 L$^-$, Notch3$^-$OX40$^+$, Notch3$^+$OX40$^+$ subsets and co-cultured with G-BMDCs. The G-BMDC-induced proliferation was maximal in Notch3$^+$OX40$^+$ Tregs compared to Notch3$^+$OX40$^-$ and Notch3$^-$OX40$^+$ Treg subsets (FIG. 13B). To determine whether soluble OX40L and JAG1 were sufficient to cause proliferation of Tregs, CD4$^+$ T-cells were treated with soluble OX40L and JAG1 in the presence of IL-2 without any exogenous antigenic stimulation for 3 days. Exogenous IL-2 was added to maintain Treg survival in ex vivo cultures in anticipation that OX40L-JAG1 treatment would not cause Teff cell activation. As shown in FIG. 14C,D, among the different combinations tested OX40L-JAG1-IL-2 treatment caused maximum increase in the percentage of proliferating Tregs (**p<0.01) followed by OX40L-IL-2 and JAG1-IL-2. Further, CD4$^+$ T-cells treated with IL-2 alone or OX40LJAG1-IL-2 were stained for proliferation marker Ki67 and percentage of Ki67$^+$ Tregs were found to be more in OX40L-JAG1-IL-2 treated cells compared to IL-2-treated controls (FIG. 15). Taken together, these results showed that soluble OX40L and JAG1 were sufficient to cause Treg proliferation independent of TCR stimulation in an IL-2 dependent manner.

Example 7: Soluble OX40L-JAG1-IL-2 can Cause Selective Proliferation of Tregs Independent of TCR Stimulation To validate whether OX40L-JAG1-induced Treg proliferation differs from TCR-stimulation approach, T-cell proliferation induced by TCR-dependent anti-CD3/CD28 was compared with TCR-independent OX40L-JAG1 stimulation. As shown in FIG. 14A, robust proliferation of Tregs was observed upon both OX40L-JAG1 and anti-CD3/CD28 treatment. However, unlike anti-CD3/CD28 treatment which also induced very strong Teff cell proliferation, OX40L-JAG1 treatment induced selective proliferation of Tregs without significant Teff proliferation. Analyses of activation markers expression showed a significant (***p<0.001) increase in the percentage of Teff cells expressing CD25, CD44 and CD69 upon treatment with anti-CD3/CD28 compared to control cells (FIG. 14B-D). However, no significant difference was observed between the control and OX40L-JAG1 treated Teff cells. Moreover, Tregs from both OX40L-JAG and anti-CD3/CD28 treated cells had increased CD25, CD44 and CD69 expressing cells compared to control cells. These results suggested that soluble OX40L-JAG1 can cause selective proliferation of Tregs, without significantly affecting Teff cell activation and proliferation.

Example 8: OX40L$^+$ Jagged-1 GM-BMDCs can Suppress Ongoing EAT

Figure 7:
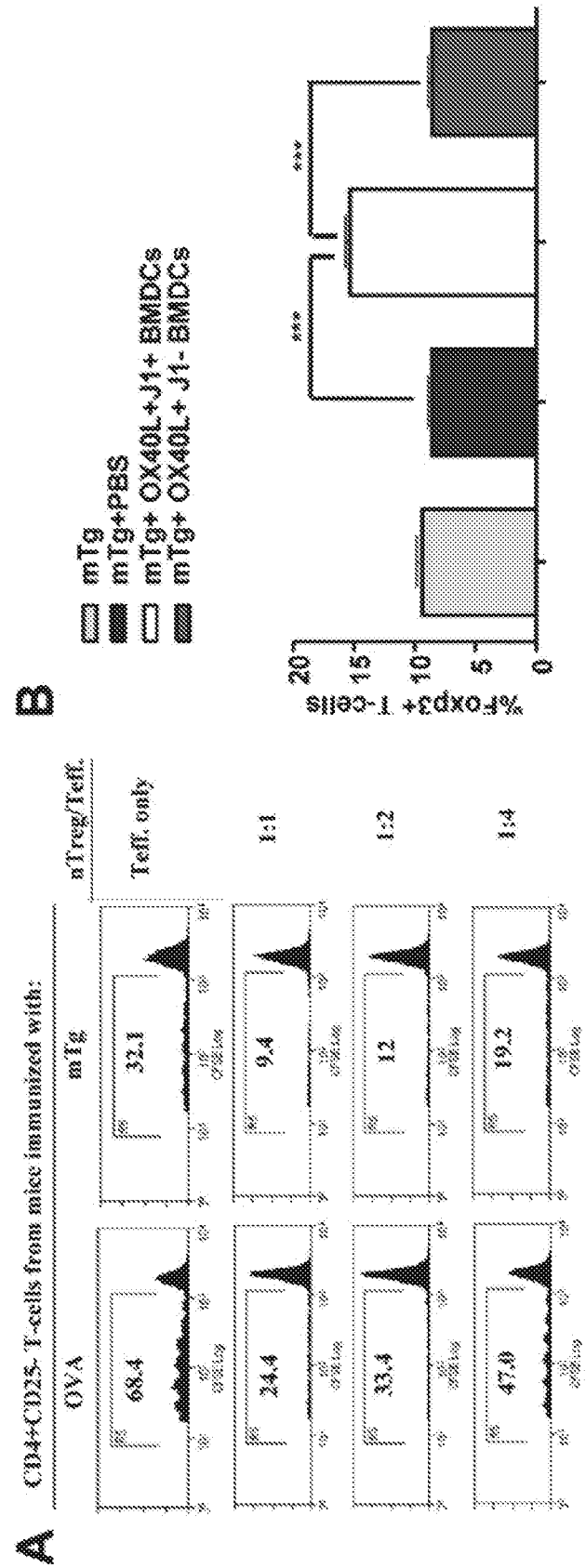
FIG. 7. OX40L⁺Jagged-1⁺ GM-BMDCs can induce Tregs in vivo and suppress EAT. (A) Ex vivo expanded Tregs can suppress effector T-cell proliferation. CD4⁺ CD25⁺ T-cells were sorted from the co-culture of OX40L⁺ Jagged-1⁺ GM-BMDCs and T-cells from naive mice. The sorted Tregs were co-cultured with CFSE labelled effector T-cells isolated from ovalbumin (OVA) and mouse thyroglobulin (mTg) immunized mice at different ratios. After 5 days in culture, CD4⁺T-cells were analyzed for CFSE dilution by FACS. (B) Experimental Autoimmune Thyroiditis (EAT) was induced in mice as described before (1). Briefly, mice were immunized with mTg+CFA on days 1 and 10 to induce EAT. On days 17 and 22, mice were treated with mTg pulsed OX40L⁺ Jagged-1⁺ or OX40L⁺ Jagged-1⁻ GM-BMDCs. Mice were sacrificed on day 35 and analyzed for Foxp3⁺ Tregs in the spleen by FACS. (C) Bar graphs showing percentage of IFN-γ, IL-4 and IL-10 producing CD4⁺ cells in the spleen of treated mice analyzed by FACS. (D) Bar graphs showing percentage of IFN-γ, IL-4 and IL-10 producing CD4⁺ cells in thyroid draining lymph nodes of differently treated mice analyzed by FACS. (E) Hematoxylin and eosin stain (H & E) stained sections of thyroid tissue showing extent of tissue infiltration by lymphocytes. Note no infiltration was detected in unimmunized mice. While significant infiltration is seen in thyroids from mice that were either treated with PBS or with OX40L⁺Jagged-1⁻ GM-BMDCs, there was minimal inflammation in mice treated with OX40L⁺Jagged-1⁺ GM-BMDCs. Results shown are representative of three independent experiments.
Figure 7:
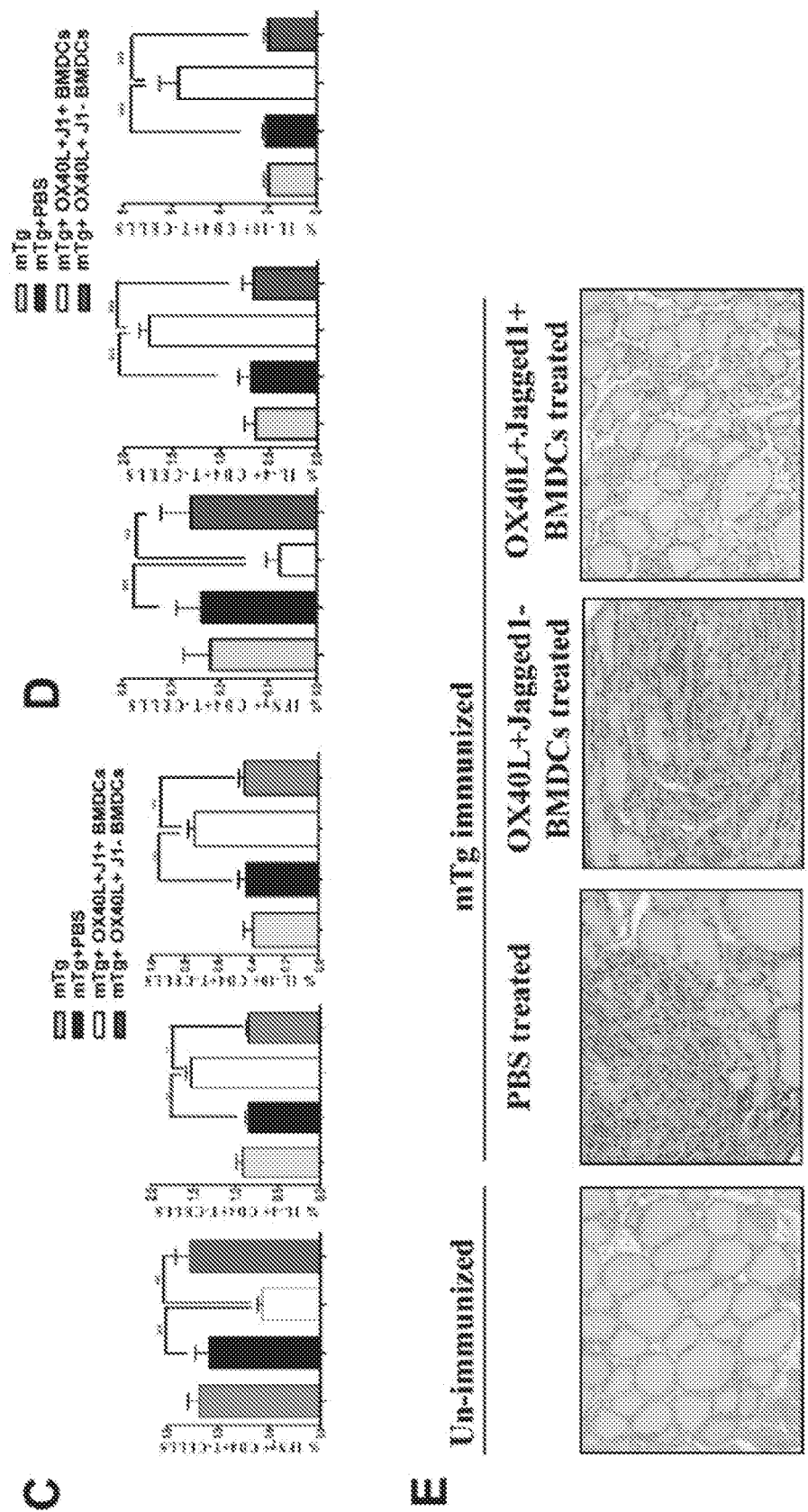

The suppressive effect of ex vivo generated Tregs on antigen-induced T cell proliferation was tested. Mice were immunized with 100 µg mTg or OVA to induce an antigen specific effector T cell response, which was monitored through the emergence of serum antibodies to mTg and OVA respectively. T cells from naïve mice were used to set up GM-BMDC/T-cell co-cultures to generate Tregs. In the absence of TCR stimulation, the expanded Tregs were a major fraction of the CD25$^+$ T-cells and were therefore isolated on the basis of CD25 expression. CD4$^+$CD25$^-$ T cells were then isolated from the above-mentioned immunized animals, stained them with CFSE and co-cultured with splenic APCs in the presence of mTg or OVA with or without sorted Tregs (CD4$^+$CD25$^+$). CD25$^-$ cells from OVA-immunized mice and mTg-immunized mice proliferated in the presence of OVA and mTg respectively. Exogenous OVA-induced proliferation was much more robust as compared to the autoantigen mTg-induced proliferation. Both mTg- and OVA-induced proliferations were significantly suppressed when CD25$^+$ Tregs were added at either 1:1, 1:2, 1:4 Tregs:Teffs ratios (FIG. 7A). These results showed that ex vivo generated Tregs were functionally competent.

Since only a small fraction of GM-BMDC, viz. the OX40L$^+$ Jagged-1$^+$ fraction, could expand Tregs ex vivo, subpopulation of DCs were also tested to determine if they could also expand Tregs in vivo and confer protection against EAT. Mice were immunized with mTg+CFA on days 1 and 10 to induce EAT. On days 17 and 22, these mice were adoptively transferred with different subsets of GM-BMDC. Mice were sacrificed on day 35 and analyzed for Foxp3$^+$ Tregs. The OX40L$^+$ Jagged-1$^+$ GM-BMDC recipient mice showed a significant increase in the percentage of Foxp3$^+$ Tregs in the spleen (15.0±0.5%) compared to control mice that were treated with PBS (9.2±1.0%) or mice that received OX40L$^+$ Jagged-1$^-$ GM-BMDC (9.0±0.5%) (p<0.01 v/s OX40L$^+$ Jagged-1$^+$ GM-BMDC in both cases) (FIG. 7B). CD4$^+$ T-cells from these recipient mice were re-stimulated with mTg in the presence of APCs for 3 days and analyzed for cytokine production. Mice that received OX40L$^+$ Jagged-1$^+$ GM-BMDC showed a significant decrease in IFNγ producing CD4T cells (p<0.01), while showing a significant increase (p<0.01) in IL-4$^+$ and IL-10$^+$ CD4$^+$ T cells compared to controls (FIG. 7C). Similarly, the cytokine profile of T-cells from thyroid draining lymph nodes of OX40L$^+$ Jagged-1$^+$ GM-BMDC recipient mice showed significantly lower percentages of IFN-γ$^+$ cells, while the percentages of IL-4$^+$ and IL-10$^+$ CD4$^+$T cells were significantly (p=0.001) higher (FIG. 7D) relative to the controls.

Thyroid histopathology revealed reduced infiltration of lymphocytes into the thyroid of OX40L$^+$ Jagged-1$^+$ GM-BMDC-recipient mice compared to the control groups either treated with OX40L$^+$ Jagged-1$^-$ GM-BMDCs or left untreated (p=0.02 in both cases; FIG. 7E). These results showed that OX40L$^+$ Jagged-1$^+$ GM-BMDC can increase the number of Tregs in vivo, with a concomitant decrease in Th1 cytokines and increase in suppressor cytokines, and suppress ongoing EAT. This observation is consistent with the earlier findings which showed that protection conferred by the treatment with low dose GM-CSF was primarily mediated through increased production of IL-10 as a result of expansion of IL10$^+$CD4$^+$Foxp3$^+$T-regs in these mice (6).

Figure 9:
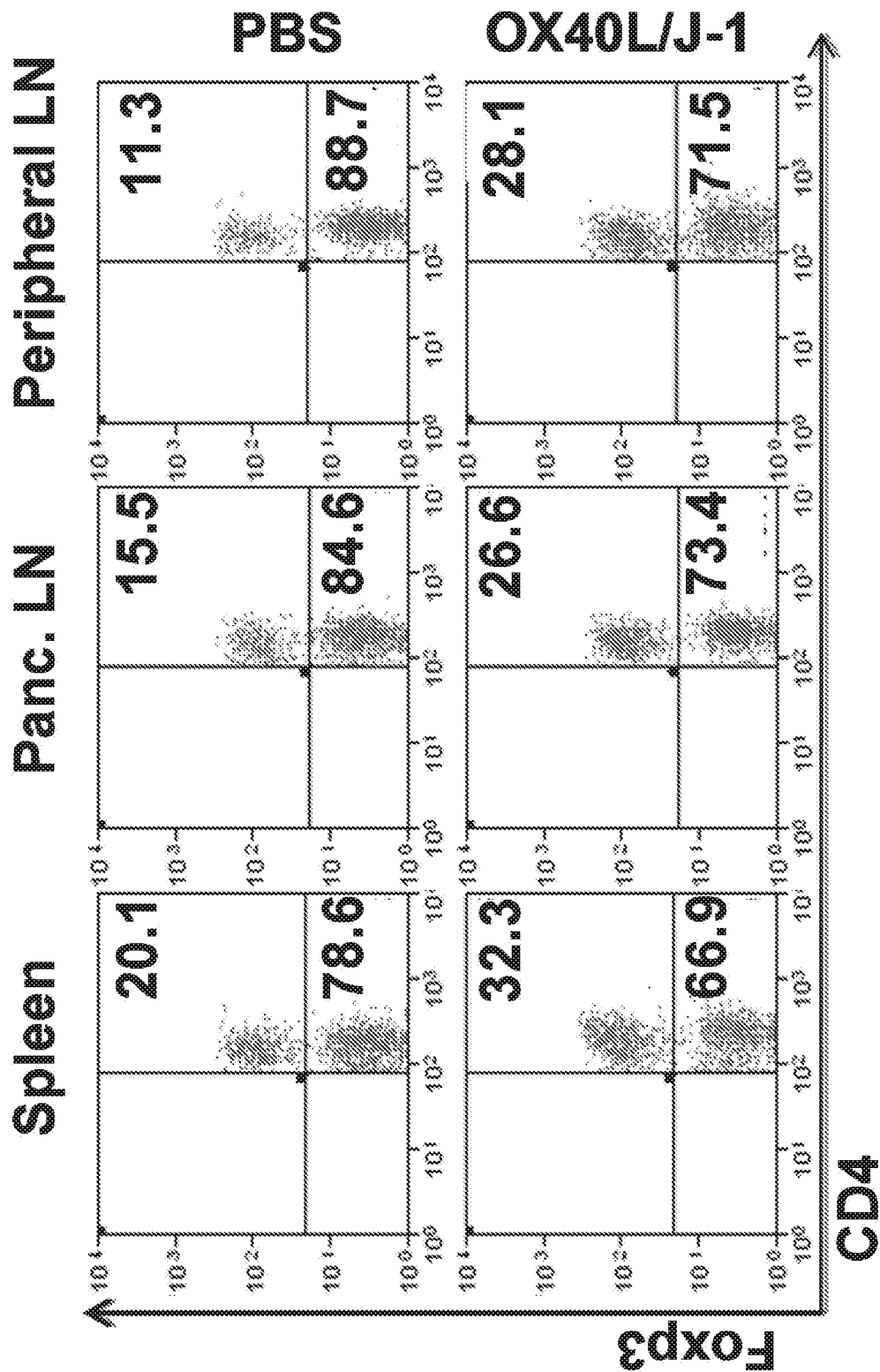
FIG. 9. Treatment of NOD mice with soluble OX40L/Jagged-1 leads to increased percentage of Foxp3 Tregs in the spleen and lymph nodes. 10-week old NOD mice were treated 3-times with PBS or soluble recombinant OX40L (200 μg/dose) and soluble recombinant Jagged-1 (100 μg/dose). Spleen and lymph node tissues were analyzed. Mice receiving OX40L & Jagged-1 showed a significant increase in the percentage of Foxp3⁺ Tregs in the spleen (i.e, 20.1% in PBS treated vs 32.3% in ligand treated), pancreatic (15.5 vs 26.6%) and peripheral lymph nodes (11.3% vs 28.1%), indicating that soluble OX40L & Jagged-1 treatment can cause Treg expansion in-vivo.
Figure 10:
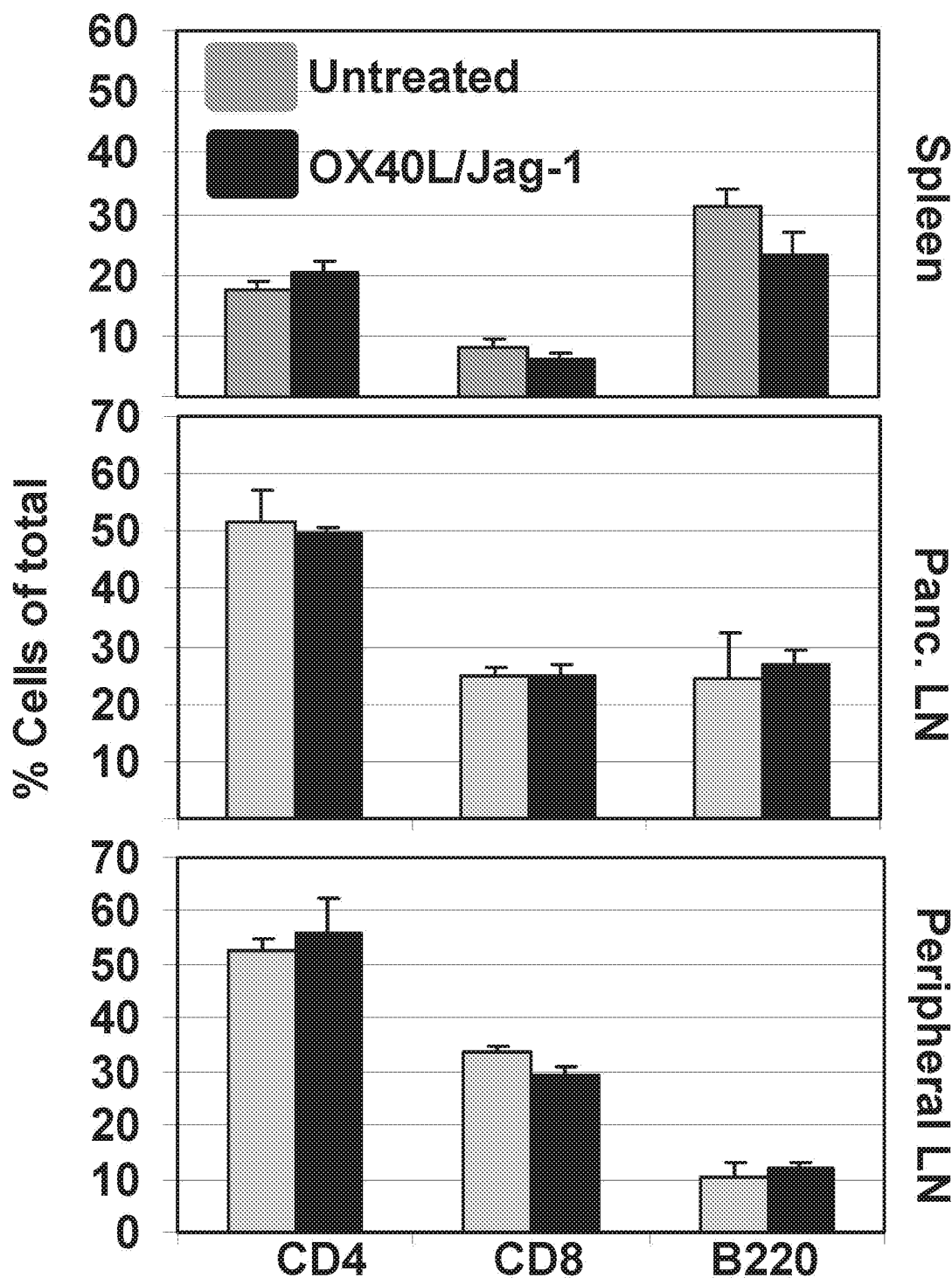
FIG. 10. Treatment of NOD mice with soluble OX40L/Jagged-1 did not affect percentages of T-cells or B-cells in lymphoid organs. 10-week old NOD mice were treated 3-times with PBS or soluble recombinant OX40L (200 µg/dose) and soluble recombinant Jagged-1 (100 µg/dose). Spleen and lymph node tissues were analyzed. Treatment did not affect the percentages of $CD4^+$, $CD8^+$ and $B220^+$ cells in the lymphoid organs.
Figure 11:
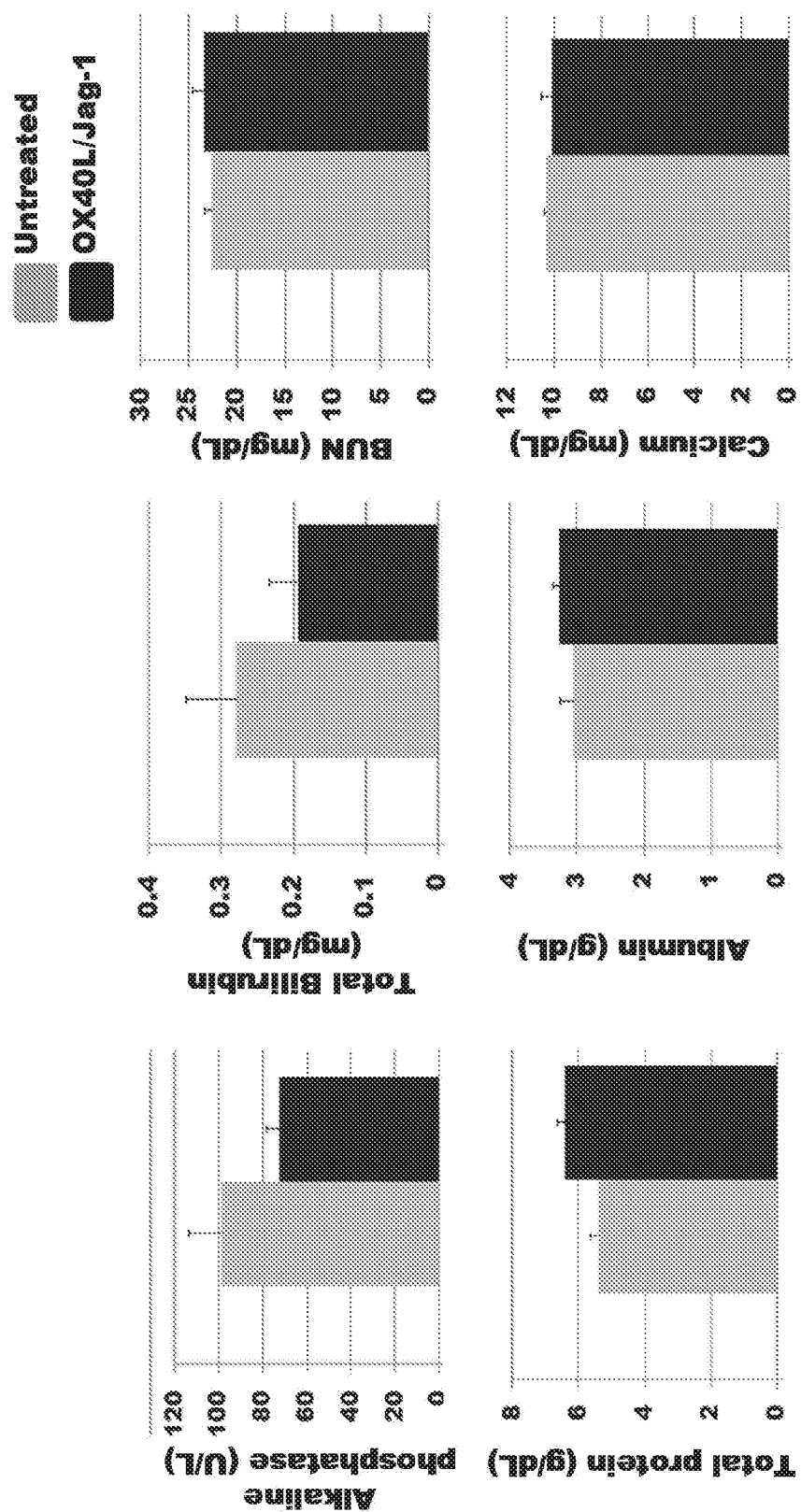
FIG. 11. OX40L/Jagged-1 treatment does not impair normal physiological functions of liver and kidney. 10-week old NOD mice were treated 3-times with PBS or soluble recombinant OX40L (200 µg/dose) and soluble recombinant Jagged-1 (100 µg/dose). Serum calcium and BUN tests were used as indicators or normal renal function. Serum alkaline phosphatase, total bilirubin total protein and albumin were used as indicators of normal liver function.
Figure 12:
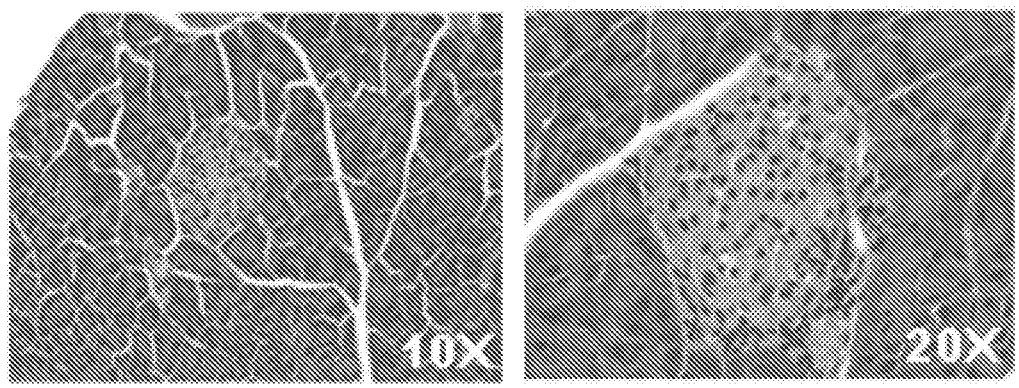
FIG. 12. H&E stained pancreatic tissue sections showed no B-cell damage upon OX40/Jagged-1 treatment. 10-week old NOD mice were treated 3-times with PBS or soluble recombinant OX40L (200 µg/dose) and soluble recombinant Jagged-1 (100 µg/dose). Pancreatic tissue sections were stained with H&E. The stained pancreatic tissue did not show any cell damage following OX40L and Jagged-1 treatment (OX40L/J-1).
Figure 12:
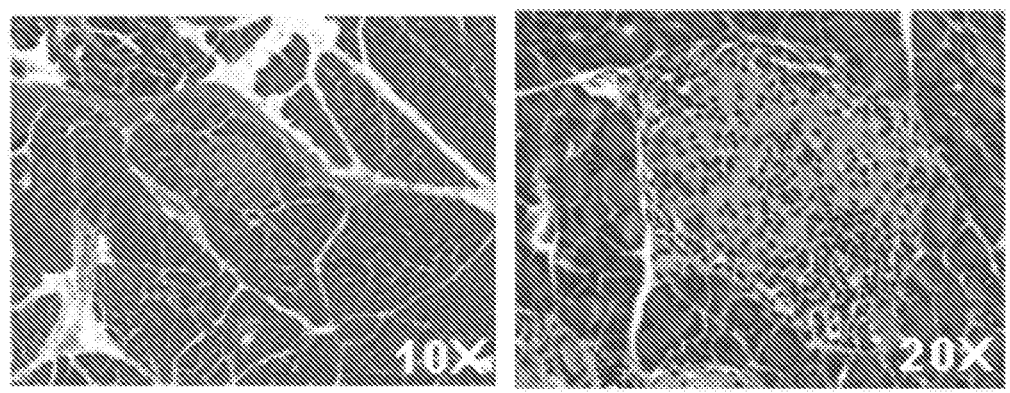

Example 9: Soluble OX40L-JAG1 Treatment Selectively Induces Treg Proliferation In Vivo and Prevents Diabetes Onset in NOD Mice To examine whether soluble OX40L-JAG1 induced co-signaling can cause Treg proliferation in vivo in non-obese diabetic (NOD) mice, a model of type 1 diabetes (T1D) was used. Ten-week-old NOD mice were treated 3-times with PBS or soluble recombinant OX40L (200 µg/dose) and soluble recombinant Jagged-1 (100 µg/dose). The mice were not treated with exogenous IL-2, as it was expected that IL-2, which is required for Treg survival, would be available in vivo. Following treatment, mice were sacrificed and different tissues were analyzed for changes in the percentage of Tregs, CD4+ and CD8+ T lymphocytes and B cells. Mice receiving OX40L & Jagged-1 showed a significant increase in the percentage of Foxp3$^+$ Tregs in the spleen (e.g., 20.1% in PBS treated vs 32.3% in ligand treated), pancreatic (15.5 vs 26.6%) and peripheral lymph nodes (11.3% vs 28.1%) (FIG. 9). Additionally, this treatment did not affect CD4$^+$, CD8$^+$ and B220$^+$ cell numbers (FIG. 10) and did not alter the normal physiological function of the kidney and liver (FIG. 1). H&E staining of pancreatic tissues from treatment and control mice showed no β-cell damage upon OX40L/Jagged-1 treatment (FIG. 12). Mice receiving soluble OX40L and Jagged-1 remained diabetes-free for up to 15 weeks of age compared to control (100% in treatment group vs. 66.7%). This data suggested that treatment with OX40L and Jagged-1 caused a dramatic increase in Tregs and protected against onset of diabetes, without causing any adverse side effects.

Figure 16:
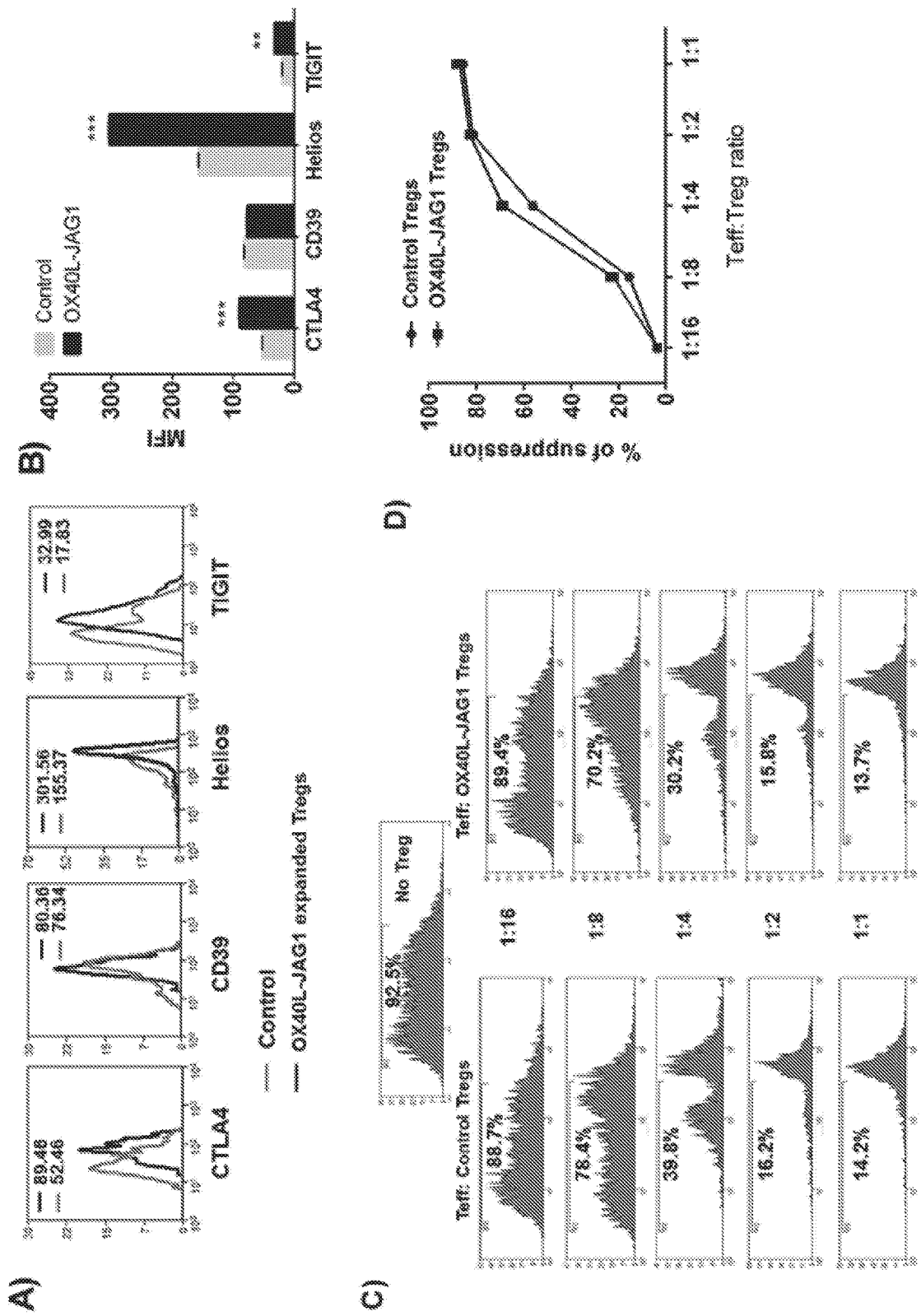
FIG. 16. Phenotypic characterization of OX40L-JAG1-IL-2 expanded Treg cells and in vitro suppression assay. (A) Control (grey) and OX40L-JAG1 (black) expanded Treg cells were analyzed for the expression of Treg suppressive markers such as CTLA4, CD39, Helios and TIGIT and CD25 by FACS analysis. Numerical indicate respective MFI values of CTLA4, CD39, Helios and TIGIT expression in control Vs OX40L-JAG1 expanded Treg cells (n=3). (B) Bar graph summarizing results shown in FIG. 17A (Values represent Mean±SEM, n=3, p<0.01, *p<0.001 Vs Control) (C) Control and OX40L-JAG expanded CD4+CD25+ Treg cells from NOD mice were co-cultured with cell trace violet labeled fresh CD4+CD25− Teff cells at indicated ratios and stimulated with anti-CD3/CD28 for 3 days. Extent of Teff proliferation was measured by flow cytometry. (D) Percentage of suppression was calculated as ratio between proliferating Teff cells from Treg:Teff co-cultures to no Treg control. Graph summarizing % of suppression calculated from 4 C (Values represent Mean±SEM, n=4).

Example 10: OX40L-JAG1-IL-2 Expanded Tregs Retain Stable-Suppressive Phenotype and Delay the Onset of Diabetes in NOD Mice To determine whether these OX40L-JAG1 expanded Tregs retained their suppressive phenotype and functions, expression of suppressive markers such as CTLA4, CD39, Helios and TIGIT was analyzed in Tregs from control and OX40L-JAG1 treated mice. As shown in FIG. 16A,B, OX40L-JAG1 expanded Tregs had significantly increased expression of suppressive markers such as CTLA4 (*$p<0.001$), Helios (*$p<0.001$) and TIGIT (**$p<0.01$) when compared to control Tregs. CD39 expression was not significantly different between control and OX40L-JAG1 expanded Tregs. Furthermore, to confirm the functional competency of OX40L-JAG1-IL-2 expanded Tregs, an ex vivo suppression assay was performed using control Tregs and OX40L-JAG1 expanded Tregs. In line with the phenotypic results, OX40L-JAG1 was found to expand Tregs to efficiently suppress Teff proliferation similar to control Tregs (FIG. 16C,D). Taken together, these results suggested that OX40L-JAG1 could expand functional Tregs without loss of their suppressive phenotype and function.

Figure 17:
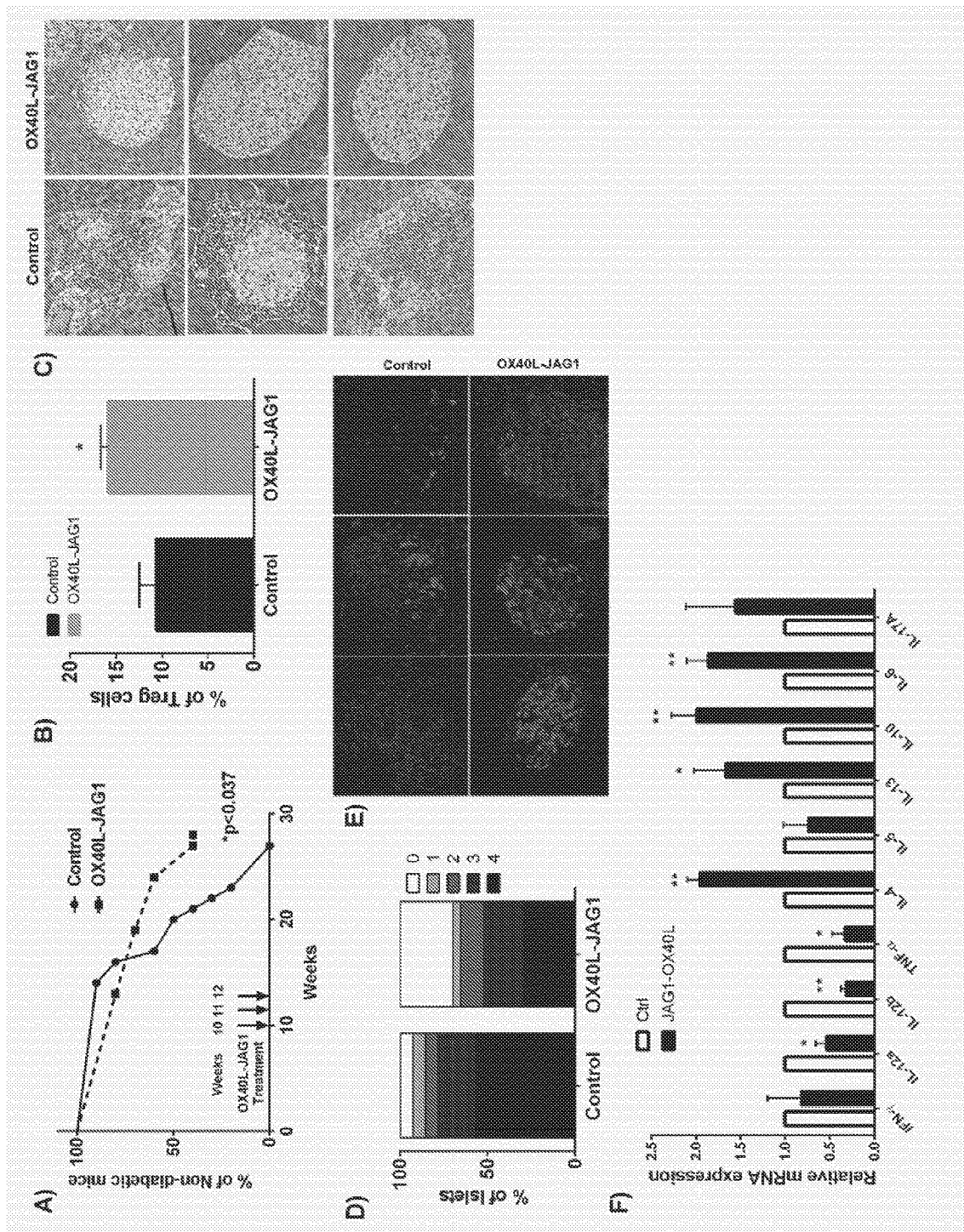
FIG. 17. Treatment of NOD mice with OX40L-JAG1 delays onset of diabetes. (A) NOD mice were administered with OX40 L and JAG1 once a week for 10-12 weeks. After OX40L-JAG1 treatment blood glucose level was monitored weekly. Kaplan-Meier survival graph shows significantly delayed onset of diabetes in NOD mice upon OX40L-JAG1 treatment (*p<0.05 Vs PBS-treated). (B) Spleens of 28 week old PBS and OX40-JAG1 treated NOD were analyzed for the percentage of CD4+ Foxp3+ Treg cells by flow cytometry. (B) Bar graph summarizing % of Tregs in spleens of PBS and OX40L-Jag1 treated mice after 28 weeks. Values are expressed as Mean±SEM (n=10, *p<0.05). (C) H & E staining analysis of pancreatic sections from PBS and OX40LJAG1 treated NOD mice (n=10). (D) Insulitis scoring was done as described in materials & methods with the following scoring scheme: 0-no insulitis, 1-peri-islet insulitis, 2-intermediate insulitis, 3-intraislet insulitis, 4-complete islet insulitis. (E) Pancreatic sections were stained for insulin by immunohistochemistry (n=10). (F) Splenocytes from PBS and OX40L-JAG1 treated mice were stimulated with PMA/Ionomycin and mRNA expression of indicated cytokines was analyzed by RT-qPCR. Expression values are expressed as fold induction over stimulated control cells after normalization with GAPDH. (Values represent Mean±SEM, n=7, *p<0.05, **p<0.01).

Next, NOD mice were treated with soluble OX40L and JAG1 once a week at 10-12 weeks of age and their blood glucose levels were monitored. As shown in FIG. 17A, by week 27, 100% of control mice became hyperglycemic, while 40% of OX40L and JAG1 treated mice were still normoglycemic (*$p<0.05$). Additionally, significantly higher percentages of Tregs were found in the spleen of OX40L and JAG1 treated mice (15.87±0.80) relative to controls (10.67±1.83; *$p<0.05$, n=10) (FIG. 17B). Examination of the pancreatic sections showed that OX40L and JAG1 treated mice had a greater number of intact islets and reduced incidence of peri-insulitis (FIG. 17C). Nearly 70% of the islets from control mice showed severe insulitis with only 7.14% exhibiting normal architecture. In contrast, only 30% of the islets from OX40L and JAG1 treated mice showed heavy infiltration and over 30% of the islets exhibited normal architecture (FIG. 17D). OX40L and JAG1 treated mice also had higher proportion of insulin secreting islets relative to control mice (FIG. 17E). Further, splenocytes from control and OX40L-JAG1 treated mice were stimulated with PMA-Ionomycin and their cytokine expression profile analyzed by RT-qPCR. Reduced expression of Th1 cytokines such as IFN-γ, IL-12α (*$p<0.05$), IL-12β (**$p<0.01$) and TNF-α (*$p<0.05$) was identified, and increased expression of Th2 cytokines such as IL-4 (**$p<0.01$) and IL-13 (*$p<0.05$) in the splenocytes from OX40L-JAG1 treated mice relative to controls was found (FIG. 17F) upon stimulation. Increased expression of anti-inflammatory cytokine IL-10 ($p<0.01$) and pro-inflammatory cytokine IL-6 ($p<0.01$) was also found in splenocytes from OX40L and JAG1 treated mice.

Figure 18:
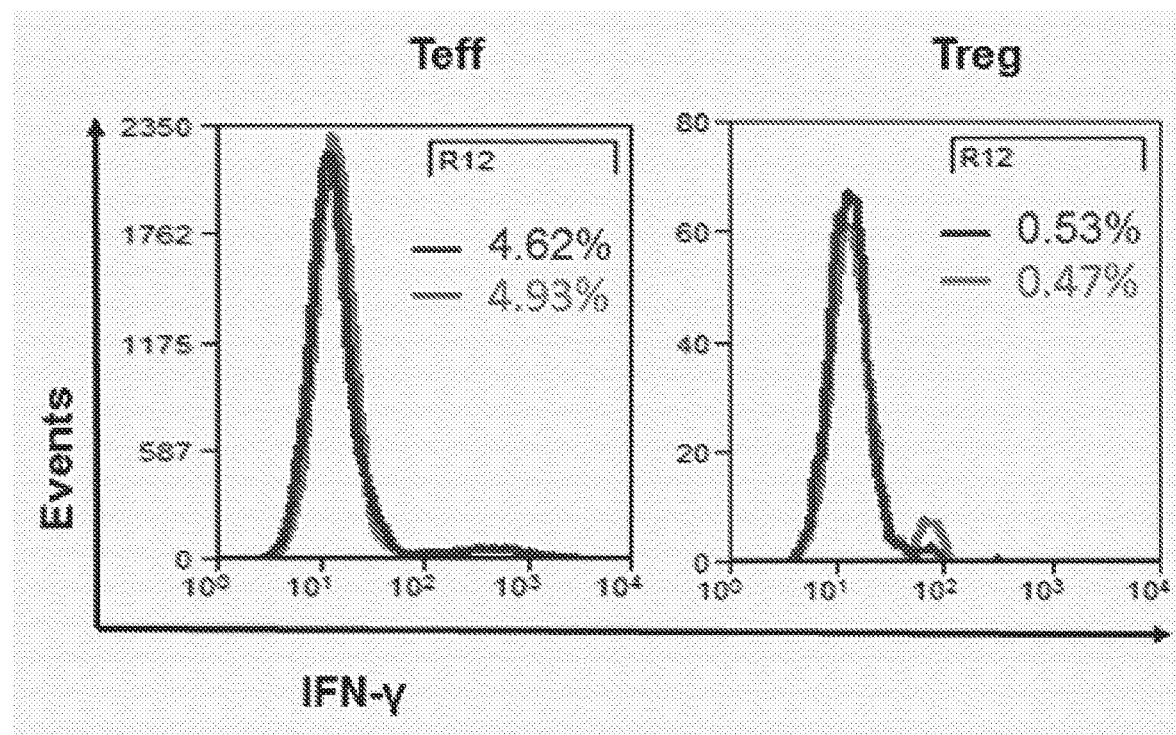
FIG. 18. Splenocytes from control and OX40L-JAG1 treated mice stimulated with PMA-Ionomycin showed no increased expression of IFN-γ in Treg or Teff cells. Histograms showing percentage of IFN-γ+ Foxp3-Teff cells and IFN-γ+Foxp3+ Treg cells in splenocytes from control (Blue) and OX40L-JAG1 (Red) stimulated with PMA-Ionomycin.

A recent study showed that transgenic expression of Notch1 intracellular domain in Treg cells can cause lymphoproliferation, exacerbated Th1 responses and autoimmunity (69). To see if a similar phenomenon was occurring, splenocytes from control and OX40L-JAG1 treated mice were stimulated with PMA-Ionomycin and both Treg and Teff cells were stained for IFN-γ expression. The results clearly show that there was no change in the percentage of IFN-γ expressing Teff cells between control and OX40L-JAG1 treated mice, and there were barely any IFN-γ expressing Tregs in both control and OX40L-JAG1 treated mice (FIG. 18).

Figure 19:
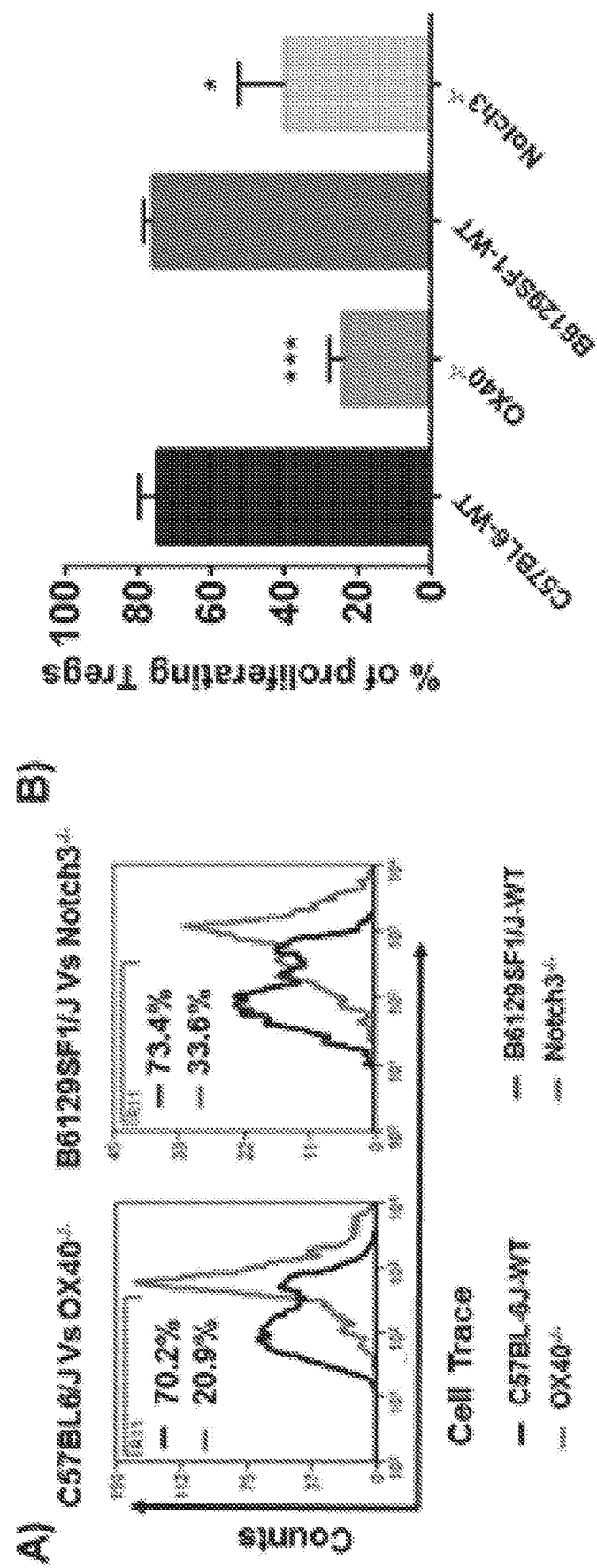
FIG. 19. Characterization of OX40L-JAG1 induced Treg proliferation in $OX40^{-/-}$ and $Notch3^{-/-}$ mice. (A) Extent of Treg proliferating induced by OX40L-JAG1-IL-2 was compared between C57BL6 wild type (black) Vs $OX40^{-/-}$ mice (grey), and B6129SF1 wild type (black) Vs $Notch3^{-/-}$ (grey) mice. Numerical represent percentages of proliferating Treg cells. (B) Bar graph summarizing results shown in (A). Values are expressed as Mean±SEM (n=3; *p<0.05, ***p<0.001 Vs respective wild type controls). (C) C57BL6 wild type, $OX40^{-/-}$, B6129SF1 wild type and $Notch3^{-/-}$ mice were treated with soluble OX40 L and JAG1 as mentioned in FIG. 3A. Spleens were analyzed for Treg cell numbers. Upper and lower panels show percentages of Tregs in PBS and OX40L-JAG1 treated mice. Numbers in upper right quadrant indicate percentages of Foxp3 Tregs (n=3). (D,E) Bar graphs (D,E) show percentages of Tregs in C57BL6-WT Vs $OX40^{-/-}$ and B6129SF1-WT Vs $Notch3^{-/-}$ mice treated with either PBS control or OX40L-JAG1 (*p<0.05, ***p<0.001 Vs WT-control; #p<0.05, ####p<0.001 Vs $OX40^{-/-}$ or $Notch3^{-/-}$ OX40L-JAG1).
Figure 19:
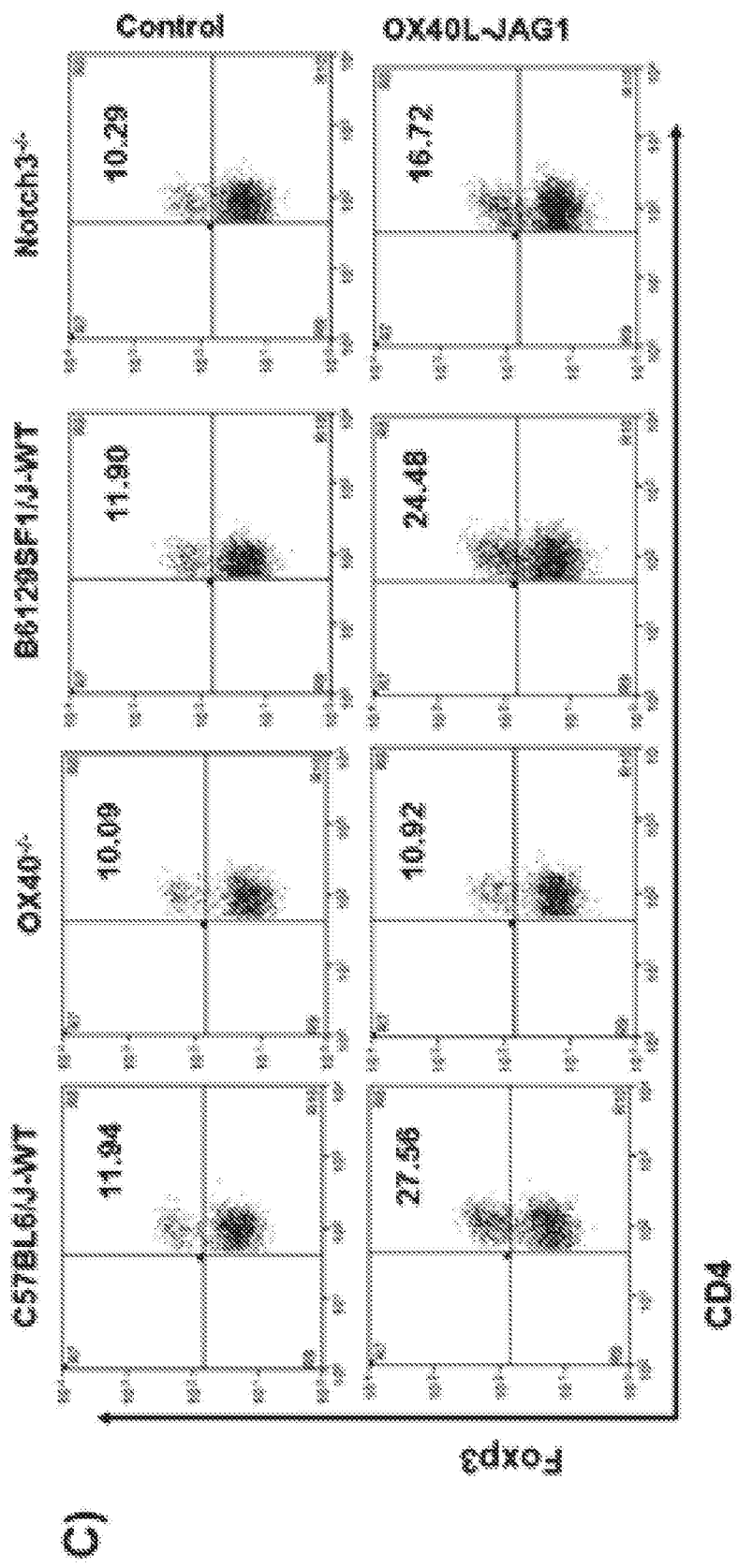
Figure 19:
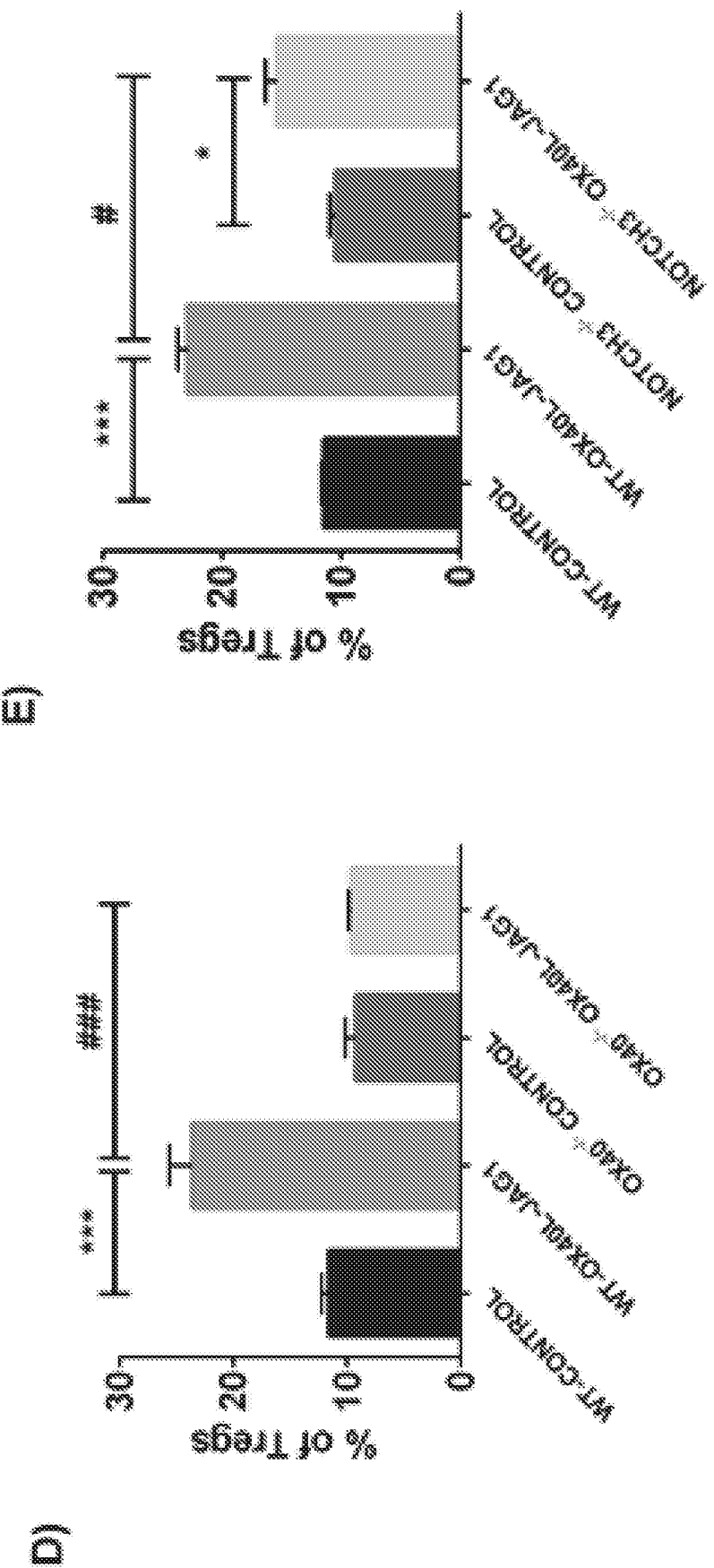
Figure 20:
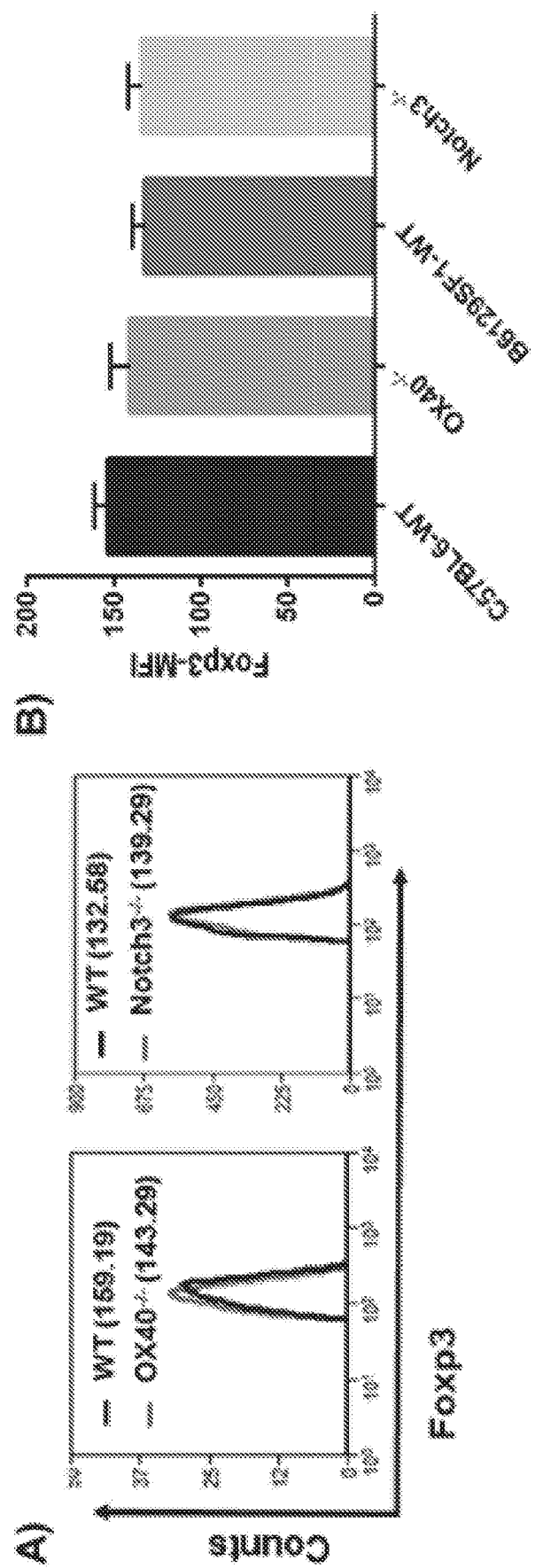
FIG. 20. Basal Foxp3 expression not significantly different among $OX40^{-/-}$, $Notch3^{-/-}$ and corresponding wild type control mice. (A) Histograms showing Foxp3 MFI values between C57BL6 wild type (black) Vs OX40−/− mice (grey), and B6129SF1 wild type (black) Vs Notch3−/− (grey) mice. (B) Bar graph summarizing results shown in (A).

Example 11: Soluble OX40L-JAG1-IL-2 Induced Treg Proliferation is Mediated Through Activation of OX40. Notch and IL-2R Mediated NF-KB and STAT5 Signaling Pathways OX40L has been shown to bind to its only known cognate receptor OX40, constitutively expressed on Tregs (10). However, JAG1 can bind to multiple receptors such as Notch, Notch2 (70) and Notch3 (71) of which Notch3 is preferentially up-regulated in Tregs (26,68). Additionally, JAG1 has been characterized as the most abundant and specific ligand for Notch3 (71). Therefore, it is hypothesized that loss of either OX40 or Notch3 might negatively affect Treg proliferation induced by OX40L, JAG1 and IL-2. We treated CD4$^+$ T-cells isolated from OX40$^{-/-}$, Notch3$^{-/-}$ and respective wild type C57BL6 and B6129SF1 control mice with soluble OX40L, JAG1 and IL-2 for 3 days. As shown in FIG. 19A,B, a significantly lower percentage of proliferating Tregs was noted from OX40$^{-/-}$ (***$p<0.001$) and Notch3$^{-/-}$ (*$p<0.05$) mice compared to their corresponding wild type controls. Further, wild type, OX40$^{-/-}$ and Notch3$^{-/-}$ mice were treated with soluble OX40L and JAG1 for 3 weeks and Treg numbers in the spleen were analyzed. As shown in FIG. 19C-E, no significant difference in the total number of splenic Tregs was observed among untreated OX40$^{-/-}$, Notch3$^{-/-}$ and the corresponding wild type control mice. Similarly, basal Foxp3 expression was also not significantly different among OX40$^{-/-}$, Notch3$^{-/-}$ and corresponding wild type control mice (FIG. 20). However, treatment with soluble OX40L-JAG1 caused a significant (\*\*\*p<0.001) increase in Treg numbers in both C57BL6/J and B6129SF1/J wild type mice, but not in OX40$^{-/-}$ mice. In OX40L-JAG1 treated Notch3$^{-/-}$ mice there was a significant increase of Tregs compared to PBS-treated Notch3$^{-/-}$ mice (\*p<0.05), but the level of increase was still significantly less than wild type mice treated with OX40L-JAG1 (\*p<0.05 Vs OX40L-JAG1). These results suggested that although expression of OX40 or Notch3 is not required for the development of Tregs or Foxp3 expression in steady state, they are indispensable for optimal Treg proliferation induced by OX40L and JAG1.

Figure 21:
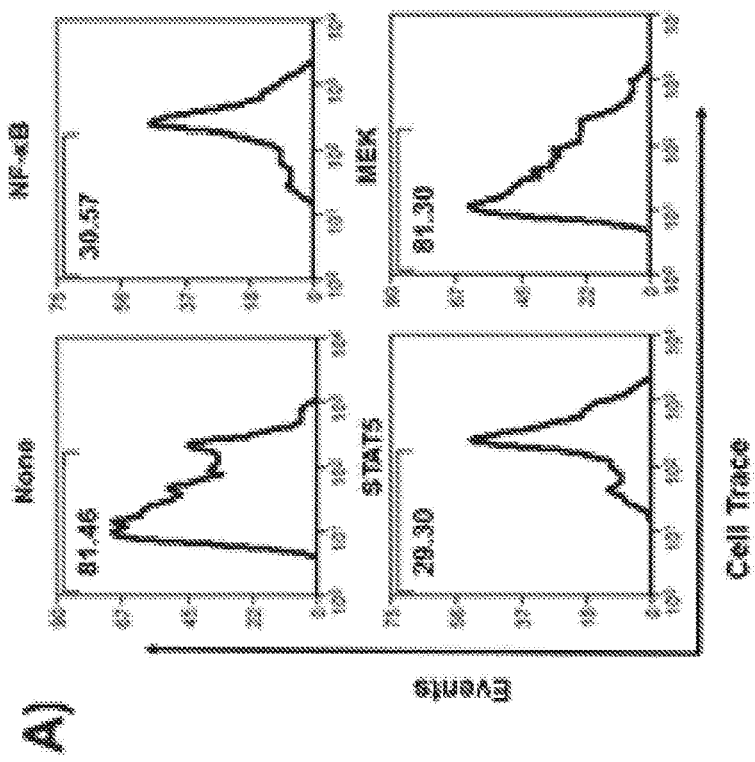
FIG. 21. Role of NF-κB and STAT5 signaling pathways in OX40L-JAG1-IL-2 induced Treg proliferation and Foxp3 expression. (A) CD4+ T-cells from NOD mice were pretreated with pharmacological inhibitors of indicated cell signaling pathways and treated with soluble OX40L-JAG1-IL-2. Effect of these pathway inhibitors on Treg cell proliferation was measured by flow cytometry analysis. (B) RT-qPCR analysis showing effect of inhibitors of NF-κB and STAT5 signaling pathways on Foxp3 mRNA expression (Values represent Mean±SEM, n=3, *p<0.05, p<0.01, *p<0.001 Vs control, #p<0.05, ##p<0.01 Vs None-OX40L-JAG1-IL-2). (C) Western blot analysis showing effect of inhibitors of NF-κB and STAT5 signaling pathways on Foxp3 protein expression. Western blot analysis of the time dependent effect of soluble OX40L-JAG1-IL-2 on (D) Foxp3 expression, (E) NF-κB p65 phosphorylation and (F) STAT5 phosphorylation in CD4+ T-cells. Western blot analysis of the effects of permutation combinations of soluble OX40L, JAG1 and IL-2 on (G) Foxp3 expression, (H) NF-κB p65 phosphorylation, and (I) STAT5 phosphorylation in CD4+ T-cells (Values represent Mean±SEM, n=3, *p<0.05, p<0.01, *p<0.001 Vs Control).
Figure 21:
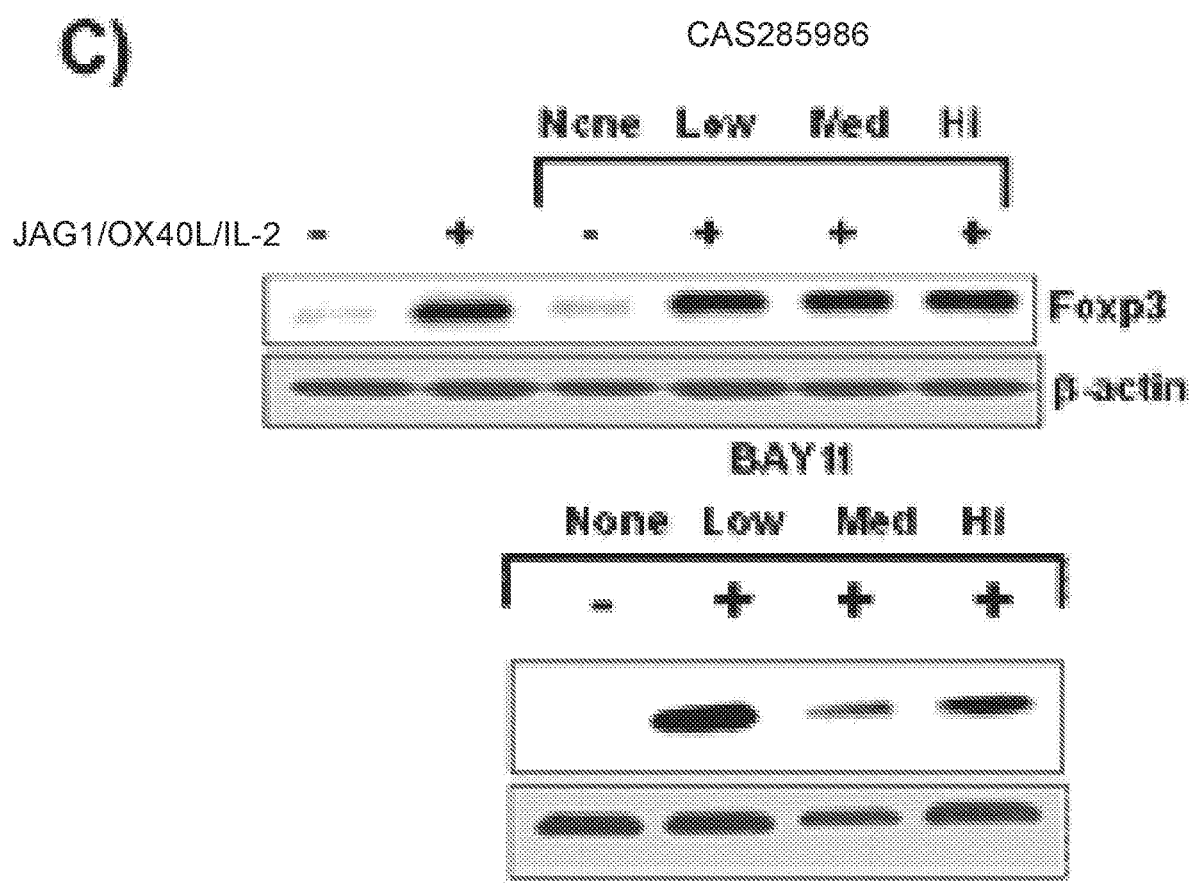
Figure 21:
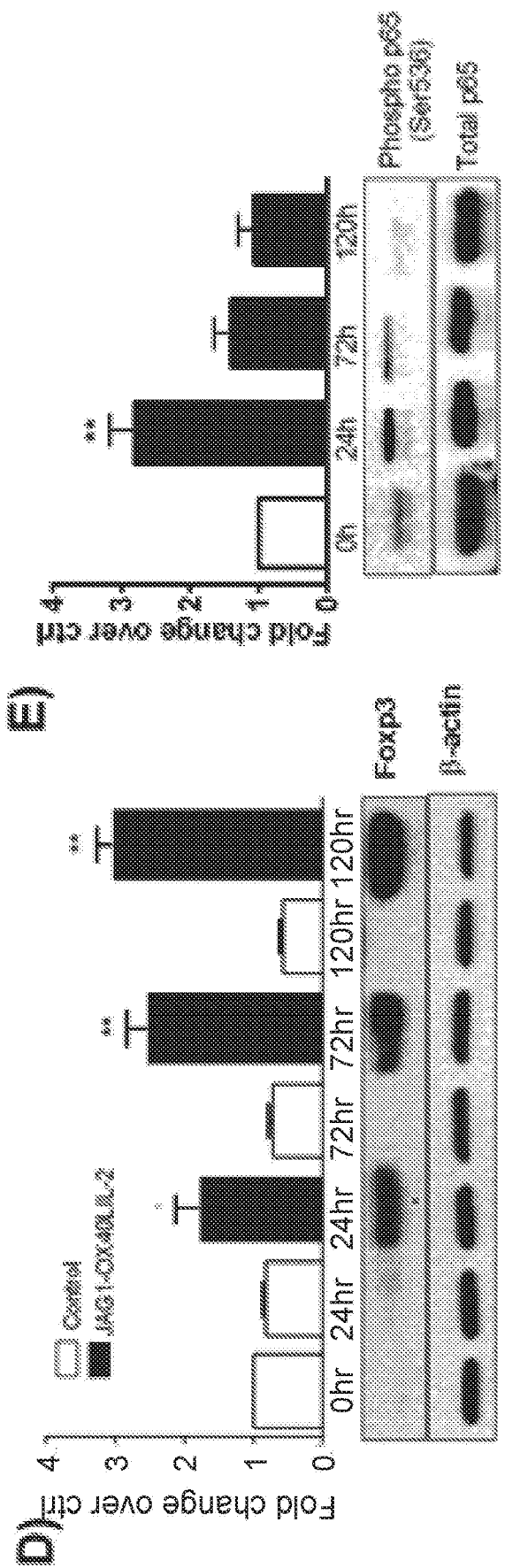
Figure 21:
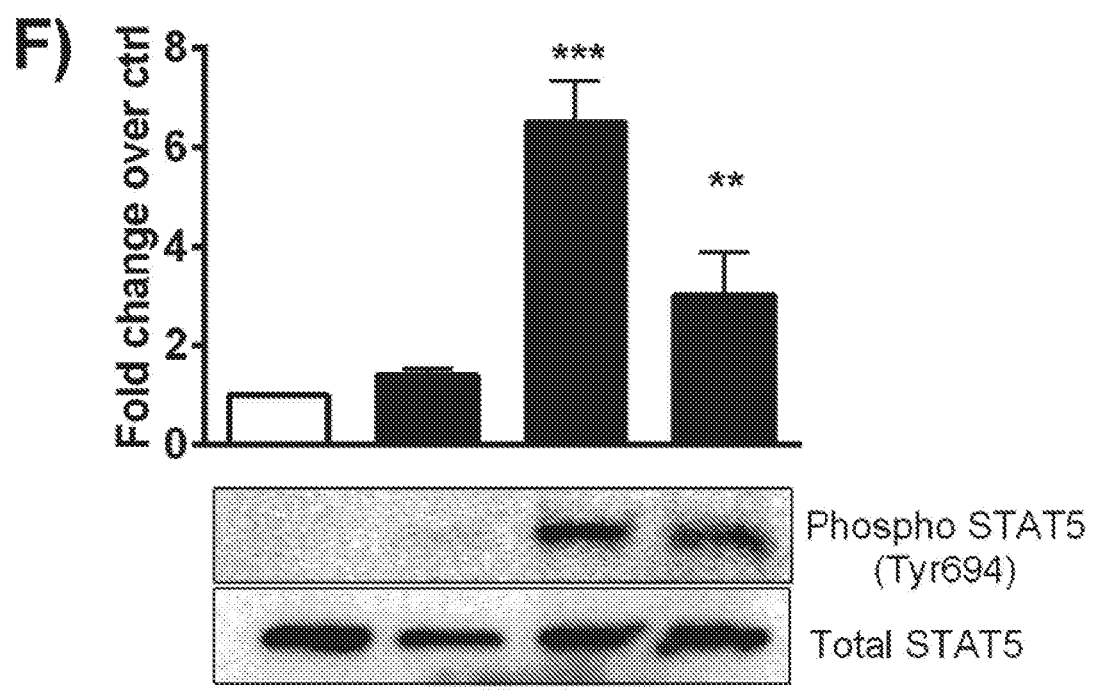
Figure 21:
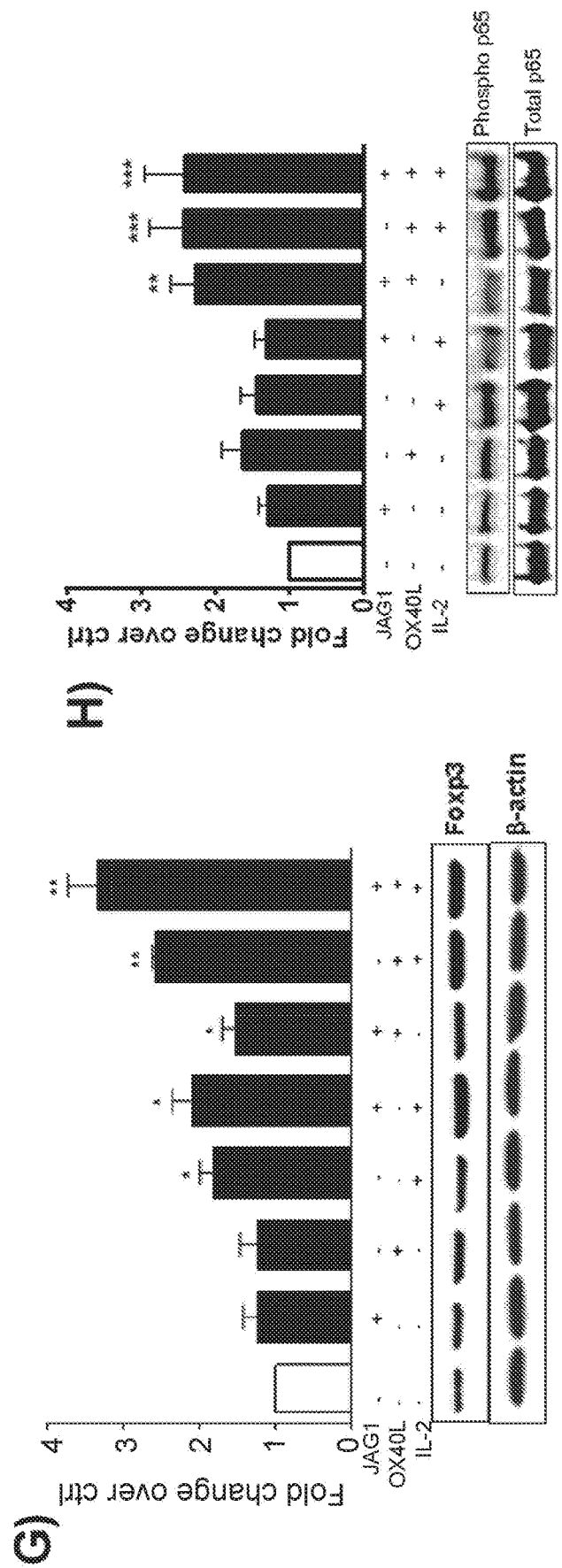
Figure 21:
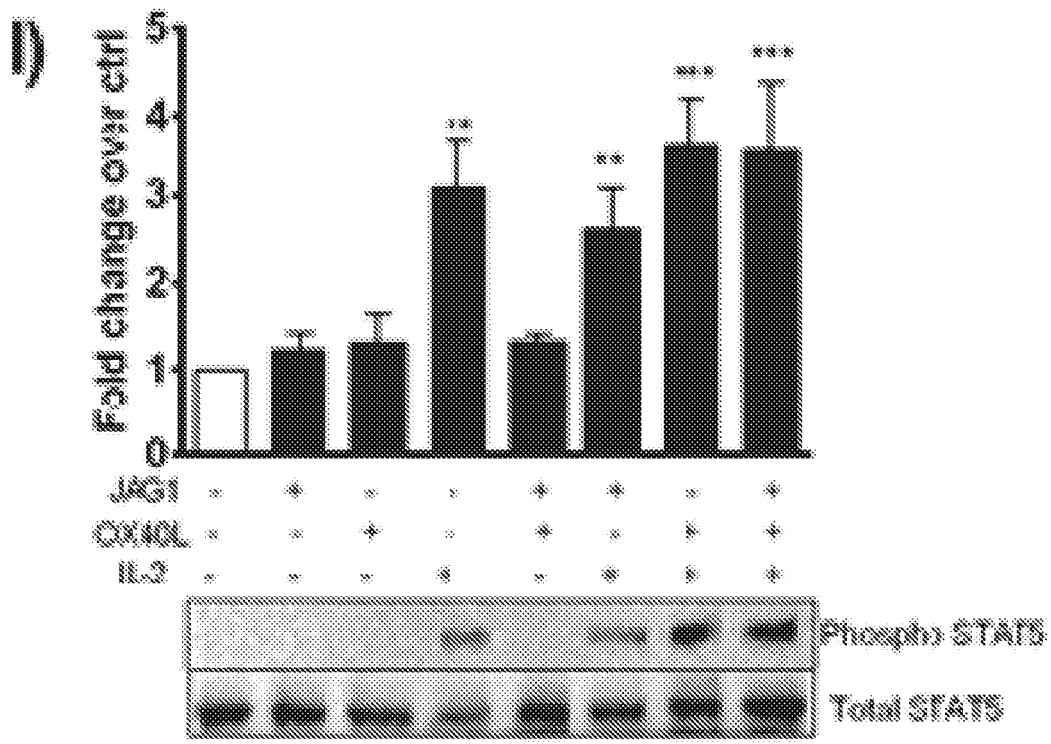

Since the micro array results suggested upregulation of genes associated with NF-κB and STAT5 signaling in proliferating Tregs compared to resting Tregs, the role of these genes in TCR independent Treg proliferation was examined. As shown in FIG. 21A, OX40L, JAG1 and IL-2-induced Treg proliferation was significantly blocked by NF-κB and STAT5 inhibitors, but not by MEK inhibitor. Next, whether NF-κB and STAT5 signaling pathways were involved in the regulation of Foxp3 expression was investigated using RT-qPCR (FIG. 21B) and Western blot (FIG. 21C). While OX40L, JAG1 and IL-2-induced Foxp3 expression was significantly down regulated in the presence of NF-κB inhibitor, it was only moderately inhibited in the presence of a STAT5 inhibitor at 24 h.

Figure 22:
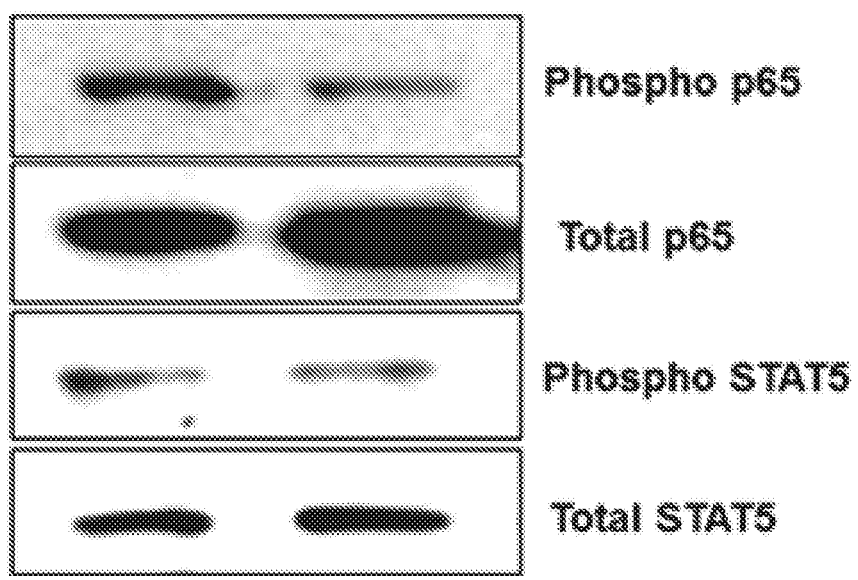
FIG. 22. OX40L-JAG-IL-2 treatment in OX40$^{-/-}$ CD4+ T-cells resulted in impaired activation of NF-κBp65; STAT5 activation remained unaffected. CD4+ T-cells from C57BL6 and OX40$^{-/-}$ mice were treated with OX40L, JAG1 and IL-2. Extent of NF-κB p65 and STAT5 phosphorylation was analyzed by Western blot.

Next, a time course analysis was carried out to determine the effect of OX40L, JAG1 and IL-2 on Foxp3 expression, and NF-κBp65 and STAT5 activation. A significant increase in Foxp3 expression was observed at 24 h (\*p<0.05) which was sustained up to 120 h (FIG. 21D). While phospo-NF-uBp65 levels were maximal at 24 h (\*\*p<0.01) (FIG. 21E), STAT5 phosphorylation was maximum at 72 h (\*\*\*p<0.001, \*\*p<0.01) (FIG. 21F). Thus, it appears that Foxp3 expression was initially induced by NF-κBp65 phosphorylation and later sustained by STAT5 activation. Next, CD4$^+$ T-cells were treated with different combinations of OX40L, JAG1 and IL-2 and analyzed for Foxp3 expression, and NF-κBp65 and/or STAT5 activation. A combination of OX40L, JAG1 and IL-2 caused maximum Foxp3 expression (\*\*p<0.01), followed by the combinations of OX40L-IL-2, JAG1-IL-2 and OX40L-JAG1 (FIG. 21G). Interestingly, a significant increase in NF-κBp65 activation was observed only upon OX40L co-treatment with JAG1 (\*\*p<0.01) or IL-2 or both (\*\*\*p<0.001) (FIG. 21H). Similarly, impaired activation of NF-κBp65 was observed in OX40$^{-/-}$ CD4$^+$T-cells upon OX40L-JAG1-IL-2 treatment while STAT5 activation remained unaffected (FIG. 22). Altogether, these results suggested that Treg proliferation might involve upstream signaling through OX40, Notch3 and IL-2R receptors followed by the activation of downstream NF-κB and STAT5 signaling pathways.

```
ADDITIONAL SEQUENCES

SEQ ID NO 51-Protein sequence of Human OX40L trimer
MEFGLSWVFLVALFRGVQCHHHHHHHHHTTAPSAQLEKELQALEKENAQLEWELQALEKELAQ
AASGGGGGSDKTHTCPPCPLIALAEEVRKLKARVDELERIRRSIGGGGGSQVSHRYPRQVSHRY
PRIQSIKVQFTEYKKEKGFILTSQKEDEIMKVQNNSVIINCDGFYLISLKGYFSQEVNISLHYQ
KDEEPLFQLKKVRSVNSLMVASLTYKDKVYLNVTTDNTSLDDFHVNGGELILIHQNPGEFCVLG
SGATNFSLLKQAGDVEENPGPMEFGLSWVFLVALFRGVQCLIALAEEVRKLKARVDELERIRRS
IGGGGGSQVSHRYPRQVSHRYPRIQSIKVQFTEYKKEKGFILTSQKEDEIMKVQNNSVIINCDG
FYLISLKGYFSQEVNISLHYQKDEEPLFQLKKVRSVNSLMVASLTYKDKVYLNVTTDNTSLDDF
HVNGGELILIHQNPGEFCVLGSGATNFSLLKQAGDVEENPGPMEFGLSWVFLVALFRGVQCLIA
LAEEVRKLKARVDELERIRRSIGGGGGSQVSHRYPRQVSHRYPRIQSIKVQFTEYKKEKGFILT
SQKEDEIMKVQNNSVIINCDGFYLISLKGYFSQEVNISLHYQKDEEPLFQLKKVRSVNSLMVAS
LTYKDKVYLNVTTDNTSLDDFHVNGGELILIHQNPGEFCVLGSGEGRGSLLTCGDVEENPGPMV
SKGEELFTGVVPILVELDGDVNGHKFSVSGEGEGDATYGKLTLKFICTTGKLPVPWPTLVTTLT
YGVQCFSRYPDHMKQHDFFKSAMPEGYVQERTIFFKDDGNYKTRAEVKFEGDTLVNRIELKGID
PKEDGNILGHKLEYNYNSHNVYIMADKQKNGIKVNFKIRHNIEDGSVQLADHYQQNTPIGDGPV
LLPDNHYLSTQSALSKDPNEKRDHMVLLEFVTAAGITLGMDELYK*

SEQ ID NO 52-Protein sequence of Mouse OX40L trimer
MEFGLSWVFLVALFRGVQCHHHHHHHHHTTAPSAQLEKELQALEKENAQLEWELQALEKELAQ
AASGGGGGSDKTHTCPPCPLIALAEEVRKLKARVDELERIRRSIGGGGGSQVSHRYPRQLSSSP
AKDPPIQRLRGAVTRCEDGQLFISSYKNEYQTMEVQNNSVVIKCDGLYIIYLKGSFFQEVKIDL
HFREDHNPISIPMLNDGRRIVFTVVASLAFKDKVYLTVNAPDTLCEHLQINDGELIVVQLTPGY
CAPEGSYHSTVNQVPLGSGATNFSLLKQAGDVEENPGPMEFGLSWVFLVALFRGVQCLIALAEE
VRKLKARVDELERIRRSIGGGGGSQVSHRYPRQLSSSPAKDPPIQRLRGAVTRCEDGQLFISSY
KNEYQTMEVQNNSVVIKCDGLYIIYLKGSFFQEVKIDLHFREDHNPISIPMLNDGRRIVFTVVA
SLAFKDKVYLTVNAPDTLCEHLQINDGELIVVQLTPGYCAPEGSYHSTVNQVPLGSGATNFSLL
KQAGDVEENPGPMEFGLSWVFLVALFRGVQCLIALAEEVRKLKARVDELERIRRSIGGGGGSQV
SHRYPRQLSSSPAKDPPIQRLRGAVTRCEDGQLFISSYKNEYQTMEVQNNSVVIKCDGLYIIYL
KGSFFQEVKIDLHFREDHNPISIPMLNDGRRIVFTVVASLAFKDKVYLTVNAPDTLCEHLQIND
GELIVVQLTPGYCAPEGSYHSTVNQVPLGSGEGRGSLLTCGDVEENPGPMVSKGEELFTGVVPI
LVELDGDVNGHKFSVSGEGEGDATYGKLTLKFICTTGKLPVPWPTLVTTLTYGVQCFSRYPDHM
KQHDFFKSAMPEGYVQERTIFFKDDGNYKTRAEVKFEGDTLVNRIELKGIDPKEDGNILGHKLE
YNYNSHNVYIMADKQKNGIKVNFKIRHNIEDGSVQLADHYQQNTPIGDGPVLLPDNHYLSTQSA
LSKDPNEKRDHMVLLEFVTAAGITLGMDELYK*

SEQ ID NO: 53-Protein sequence of Mouse OX40L trimer without trimerization motif
MEFGLSWVFLVALFRGVQCHHHHHHHHHTTAPSAQLEKELQALEKENAQLEWELQALEKELAQ
AASGGGGGSQVSHRYPRQLSSSPAKDPPIQRLRGAVTRCEDGQLFISSYKNEYQTMEVQNNSVV
IKCDGLYIIYLKGSFFQEVKIDLHFREDHNPISIPMLNDGRRIVFTVVASLAFKDKVYLTVNAP
DTLCEHLQINDGELIVVQLTPGYCAPEGSYHSTVNQVPLGSGATNFSLLKQAGDVEENPGPMEF
GLSWVFLVALFRGVQCGGGGGSQVSHRYPRQLSSSPAKDPPIQRLRGAVTRCEDGQLFISSYKN
EYQTMEVQNNSVVIKCDGLYIIYLKGSFFQEVKIDLHFREDHNPISIPMLNDGRRIVFTVVASL
AFKDKVYLTVNAPDTLCEHLQINDGELIVVQLTPGYCAPEGSYHSTVNQVPLGSGATNFSLLKQ
AGDVEENPGPMEFGLSWVFLVALFRGVQCGGGGGSQVSHRYPRQLSSSPAKDPPIQRLRGAVTR
CEDGQLFISSYKNEYQTMEVQNNSVVIKCDGLYIIYLKGSFFQEVKIDLHFREDHNPISIPMLN
DGRRIVFTVVASLAFKDKVYLTVNAPDTLCEHLQINDGELIVVQLTPGYCAPEGSYHSTVNQVP
```

| ADDITIONAL SEQUENCES |
|---|
| LGSGEGRGSLLTCGDVEENPGPMVSKGEELFTGVVPILVELDGDVNGHKFSVSGEGEGDATYGK<br>LTLKFICTTGKLPVPWPTLVTTLTYGVQCFSRYPDHMKQHDFFKSAMPEGYVQERTIFFKPDGN<br>YKTRAEVKFEGDTLVNRIELKGIDFKEDGNILGHKLEYNYNSHNVYIMADKQKNGIKVNFKIRH<br>NIEDGSVQLADHYQQNTPIGDGPVLLPDNHYLSTQSALSKDPNEKRDHMVLLEFVTAAGITLGM<br>DELYK*<br><br>SEQ ID NO: 54-Protein sequence of OX40L ectodomain from *Homo sapien*<br>QVSHRYPRIQSIKVQFTEYKKEKGFILTSQKEDEIMKVQNNSVIINCDGFYLISLKGYFSQEVN<br>ISLHYQKDEEPLFQLKKVRSVNSLMVASLTYKDKVYLNVTTDNTSLDDFHVNGGELILIHQNPG<br>EFCVL<br><br>SEQ ID NO: 55-Protein sequence of OX40L ectodomain from *Mus musculus*<br>QLSSSPAKDPPIQRLRGAVTRCEDGQLFISSYKNEYQTMEVQNNSWIKCDGLYIIYLKGSFFQ<br>EVKIDLHFREDHNPISIPMLNDGRRIVFTWASLAFKDKVYLTVNAPDTLCEHLQINDGELIVV<br>QLTPGYCAPEGSYHSTVNQVPL<br><br>SEQ ID NO: 56-Amino acid sequence of OX40L signal<br>MEFGLSWVFLVALFRGVQC<br><br>SEQ ID NO: 57-Amino acid sequence of Acid-base zipper for OX40L<br>TTAPSAQLEKELQALEKENAQLEWELQALEKELAQAAS<br><br>SEQ ID NO: 58-Peptide sequence of Porcine Teschovirus-1 2A ("P2A")<br>GSGATNFSLLKQAGDVEENPGP<br><br>SEQ ID NO: 59-Amino Acid sequence of trimeric coiled-coil for OX40L<br>LIALAEEVRKLKARVDELERIRRSI<br><br>SEQ ID NO: 60-Protein sequence of Enhanced Green Fluorescent Protein ("eGFP")<br>from Human cytomegalovirus (Human herpesvirus 5)<br>MVSKGEELFTGVVPILVELDGDVNGHKFSVSGEGEGDATYGKLTLKFICTTGKLPVPWPTLVTT<br>LTYGVQCFSRYPDHMKQHDFFKSAMPEGYVQERTIFFKDDGNYKTRAEVKFEGDTLVNRIELKG<br>IDFKEDGKILGHKLEYNYNSHNVYIMADKQKNGIKVNFKIRHNIEDGSVQLADHYQQNTPIGDG<br>PVLLPDNHYLSTQSALSKDPNEKRDHMVLLEFVTAAGITLGMDELYK<br><br>SEQ ID NO: 61-Protein sequence of Human Jagged-1 ("JAG1")<br>MDMRVPAQLLGLLLLWLSGARCMRSPRTRGRSGRPLSLLLALLCALRAKVCGASGQFELEILSM<br>QNVNGELQNGNCCGGARNPGDRKCTRDECDTYFKVCLKEYQSRVTAGGPCSFGSGSTPVIGGNT<br>FNLKASRGNDRNRIVLPFSFAWPRSYTLLVEAWDSSNDTVQPDSIIEKASHSGMINPSRQWQTL<br>KQNTGVAHFEYQIRVTCDDYYYGFGCNKFCRPRDDFFGHYACDQNGNKTCMEGWMGPECNRAIC<br>RQGCSPKHGSCKLPGDCRCQYGWQGLYCDKCIPHPGCVHGICNEPWQCLCETNWGGQLCDKDGG<br>GGSTTAPSAQLKKKLQALKKKNAQLKWKLQALKKKLAQGGGGGSRKCCVECPPCPAPPVAGPS<br>VFLFPPKPKDTLMISRTPEVTCVVVDVSHEDPEVQFNWYVDGVEVHNAKTKPREEQFNSTFRVV<br>SVLTVVHQDWLNGKEYKCKVSNKGLPAPIEKTISKTKGQPREPQVYTLPPSREEMTKNQVSLTC<br>LVKGFYPSDIAVEWESNGQPENNYKTTPPMLDSDGSFFLYSKLTVDKSRWQQGNVFSCSVMHEA<br>LHNHYTQKSLSLSPGKGSGEGRGSLLTCGDVEENPGPMASSEDVIKEFMRFKVRMEGSVNGHEF<br>EIEGEGEGRPYEGTQTAKLKVTKGGPLPFAWDILSPQFQYGSKAYVKHPADIPDYLKLSFPEGF<br>KWERVMNFEDGGWTVTQDSSLQDGEFIYKVKLRGTNFPSDGPVMQPCKTMGWEASTERMYPEDG<br>ALKGEIKMRLKLKDGGHYDAEVKTTYMAKKPVQLPGAYKTDIKLDITSHNEDYTIVEQYERAEG<br>RHSTGA*<br><br>SEQ ID NO: 62-Protein sequence of Mouse Jagged-1 ("JAG1")<br>MDMRVPAQLLGLLLLWLSGARCMRSPRTRGRPGRPLSLLLALLCALRAKVCGASGQFELEILSM<br>QNVNGELQNGNCCGGVRNPGDRKCTRDECDTYFKVCLKEYQSRVTAGGPCSFGSGSTPVIGGNT<br>FNLKASRGNDRNRIVLPFSFAWPRSYTLLVEAWDSSNDTIQPDSIIEKASHSGMINPSRQWQTL<br>KQNTGIAHFEYQIRVTCDDHYYGFGCNKFCRPRDDFFGHYACDQNGNKTCMEGWMGPDCNKAIC<br>RQGCSPKHGSCKLPGDCRCQYGWQGLYCDKCIPHPGCVHGTCNEPWQCLCETNWGGQLCDKDGG<br>GGSTTAPSAQLKKKLQALKKKNAQLKWKLQALKKKLAQGGGGGSGNSISAMVRSGCKFCICTV<br>PEVSSVFIFPPKPKDVLTITLTPKVTCVVVDISKDDPEVQFSWFVDDVEVHTAQTQPREEQFNS<br>TFRSVSELPIMHQDWLNGKEFKCRVNSAAFPAPIEKTISKTKGRPKAPQVYTIPPPKEQMAKDK<br>VSLTCHITDFFPEDITVEWQWNGQPAENYKNTQPIMDTDGSVFVYSKLNVQKSNWEAGNTFTCS<br>VLHEGLHNHHTEKSLSHSPGKGSGEGRGSLLTCGDVEENPGPMASSEDVIKEFMRFKVRMEGSV<br>NGHEFEIEGEGEGRPYEGTQTAKLKVTKGGPLPFAWDILSPQFQYGSKAYVKHPADIPDYLKLS<br>FPEGFKWERVMNFEDGGVVTVTQDSSLQDGEFIYKVKLRGTNFPSDGPVMQKKTMGWEASTERM<br>YPEDGALKGEIKMRLKLKDGGHYDAEVKTTYMAKKPVQLPGAYKTDIKLDITSHNEDYTIVEQY<br>ERAEGRHSTGA*<br><br>SEQ ID NO: 63-Protein sequence of Jagged-1 from *H. sapien*<br>MRSPRTRGRSGRPLSLLLALLCALRAKVCGASGQFELEILSMQNVNGELQNGNCCGGARNPGDR<br>KCTRDECDTYFKVCLKEYQSRVTAGGPCSFGSGSTPVIGGNTFNLKASRGNDRNRIVLPFSFAW<br>PRSYTLLVEAWDSSNDTVQPDSIIEKASHSGMINPSRQWQTLKQNTGVAHFEYQIRVTCDDYYY<br>GFGCNKFCRPRDDFFGHYACDQNGNKTCMEGWMGPECNRAICRQGCSPKHGSCKLPGDCRCQYG<br>WQGLYCDKCIPHPGCVHGICNEPWQCLCETNWGGQLCDKDGGGGS<br><br>SEQ ID NO: 64-Protein sequence of Jagged-1 from *M. musculus*<br>MRSPRTRGRPGRPLSLLLALLCALRAKVCGASGQFELEILSMQNVNGELQNGNCCGGVRNPGDR<br>KCTRDECDTYFKVCLKEYQSRVTAGGPCSFGSGSTPVTGGNTFNLKASRGNDRNRIVLPFSFAW |

| ADDITIONAL SEQUENCES |
| --- |
| PRSYTLLVEAWDSSNDTIQPDSIIEKASHSGMINPSRQWQTLKQNTGIAHFEYQIRVTCDDHYY<br>GFGCNKFCRPRDDFEGHYACDQNGNKTCMEGWHGPDCNKAICRQGCSPKHGSCKLPGDCRCQYG<br>WQGLYCDKCIPHPGCVHGTCNEPWQCLCETNWGGQLCDKDGGGS<br><br>SEQ ID NO: 65-Amino acid sequence of Jagged-1 signal<br>MDMRVPAQLLGLLLLWLSGARC<br><br>SEQ ID NO: 66-Amino acid sequence of Acid-base dimer for Jagged-1<br>TTAPSAQLKKKLQALKKKKNAQLKWKLQALKKKLAQ<br><br>SEQ ID NO: 67-Peptide sequence of Thosea asigna virus 2A ("T2A")<br>GSGEGRGSLLTCGDVEENPGP<br><br>SEQ ID NO: 68-Protein sequence of Human Immunoglobulin G2 Fc ("IgG2Fc") region<br>RKCCVECPPCPAPPVAGPSVFLFPPKPKDTLMISRTPEVTCVVVDVSHEDPEVQFNWYVDGVEV<br>HKAKTKPREEQFNSTFRVVSVLTVVHQDWLNGKEYKCKVSNKGLPAPIEKTISKTKGQPREPQV<br>YTLPPSREEMTKNQVSLTCLVKGFYPSDIAVEWESNGQPENNYKTTPPMLDSDGSFFLYSKLTV<br>DKSRWQQGNVFSCSYMHEALHNHYTQKSLSLSPGK<br><br>SEQ ID NO: 69-Protein sequence of Mouse Immunoglobulin G2a Fc ("IgG2aFc") region<br>GNSISAMVRSGCKPCICTVPEVSSVFIFPPKPKDVLTITLTPKVTCVVVDISKDDPEVQFSWFV<br>DDVEVHTAQTQPREEQFNSTFRSVSELPIMHQDWLNGKEFKCRVNSAAFPAPIEKTISKTKGRP<br>KAPQVYTIPPPKEQMAKDKVSLTCMITDFFPEDITVEWQWNGQPAENYKNTQPTMDTDGSYFVY<br>SKLNVQKSNWEAGNTFTCSVLHEGLHNHHTEKSLSHSPGK<br><br>SEQ ID NO: 70-Protein sequence of Monomer Red Fluorescent Protein ("mRFP")<br>MASSEDVIKEFMRFKVRMEGSVNGHEFEIEGEGEGRPYEGTQTAKLKVTKGGPLPFAWDILSPQ<br>FQYGSKAYVKHPADIPDYLKLSFPEGFKWERVMNFEDGGVVTVTQDSSLQDGEFIYKVKLRGTN<br>FPSDGPVMQKKTMGWEASTERMYPEDGALKGEIKMRLKLKDGGHYDAEVKTTYMAKKPVQLPGA<br>YKTDIKLDITSHNEDYTIVEQYERAEGRHSTGA* |

REFERENCES

1. Vasu et al., 2003, Selective induction of dendritic cells using granulocyte macrophage-colony stimulating factor, but not fms-like tyrosine kinase receptor 3-ligand, activates thyroglobulin-specific CD4+/CD25+ T cells and suppresses experimental autoimmune thyroiditis. *J. Immunol* 170: 5511-22
2. Sheng et al., 2006. Suppression of experimental autoimmune myasthenia gravis by granulocyte-macrophage colony-stimulating factor is associated with an expansion of FoxP3+ regulatory T cells. *J Immunol* 177: 5296-306
3. Cheatem et al., 2009. Modulation of dendritic cells using granulocyte-macrophage colony-stimulating factor (GM-CSF) delays type 1 diabetes by enhancing CD4+CD25+ regulatory T cell function. *Clin Immunol* 131: 260-70
4. Gaudreau el al., 2007. Granulocyte-macrophage colony-stimulating factor prevents diabetes development in NOD mice by inducing tolerogenic dendritic cells that sustain the suppressive function of CD4+CD25+ regulatory T cells. *J Immunol* 179: 3638-47
5. Bernasconi et al., 2010. Granulocyte-macrophage colony-stimulating factor elicits bone marrow-derived cells that promote efficient colonic mucosa] healing. *Inflamm Bowel Dis* 16: 428-41
6. Ganesh et al., 2009. GM-CSF-induced CD11c+CD8a-dendritic cells facilitate Foxp3+ and IL-10+ regulatory T cell expansion resulting in suppression of autoimmune thyroiditis. *Int Immunol* 21: 269-82
7. Gangi et al., 2005. IL-10-producing CD4+CD25+ regulatory T cells play a critical role in granulocyte-macrophage colony-stimulating factor-induced suppression of experimental autoimmune thyroiditis. *J Immunol* 174: 7006-13
8. Bhattacharya et al., 2011. GM-CSF-induced, bone-marrow-derived dendritic cells can expand natural Tregs and induce adaptive Tregs by different mechanisms. *Journal of leukocyte biology* 89: 235-49
9. Godfrey et al., 1994. Identification of a human OX-40 ligand, a co-stimulator of CD4+T cells with homology to tumor necrosis factor. *J Exp Med* 180: 757-62
10. Ruby et al., 2009. Cutting Edge: OX40 agonists can drive regulatory T cell expansion if the cytokine milieu is right. *Journal of immunology* 183: 4853-7
11. Griseri et al., 2010. OX40 is required for regulatory T cell-mediated control of colitis. *The Journal of experimental medicine* 207: 699-709
12. Kared et al., 2006. Jagged2-expressing hematopoietic progenitors promote regulatory T cell expansion in the periphery through notch signaling. *Immunity* 25: 823-34
13. Hoyne et al., 2000. Serratel-induced notch signaling regulates the decision between immunity and tolerance made by peripheral CD4(+) T cells. *Int Immunol* 12: 177-85
14. Minter et al., 2005. Inhibitors of gamma-secretase block in vivo and in vitro T helper type 1 polarization by preventing Notch upregulation of Tbx21. *Nat Immunol* 6: 680-8
15. Fortini, 2009. Notch signaling: the core pathway and its posttranslational regulation. *Dev Cell* 16: 633-47
16. Amsen et al., 2004. Instruction of distinct CD4 T helper cell fates by different notch ligands on antigen-presenting cells. *Cell* 117: 515-26
17. Yvon et al., 2003. Overexpression of the Notch ligand, Jagged-1, induces alloantigen-specific human regulatory T cells. *Blood* 102: 3815-21
18. Vigouroux et al., 2003. Induction of antigen-specific regulatory T cells following overexpression of a Notch ligand by human B lymphocytes. *J Virol* 77: 10872-80
19. Elyaman et al., 2007. JAGGED-1 and delta 1 differentially regulate the outcome of experimental autoimmune encephalomyelitis. *Journal of immunology* 179: 5990-8

20. Bassil et al., 2011. Notch ligand delta-like 4 blockade alleviates experimental autoimmune encephalomyelitis by promoting regulatory T cell development. *J Immunol* 187: 2322-8
21. Lee et al., 2009. Arachidonic acid potentiates hypoxia-induced VEGF expression in mouse embryonic stem cells: involvement of Notch, Wnt, and HIF-1alpha. *Am J Physiol Cell Physiol* 297: C207-16
22. Esquivel et al., 1977. Induction of autoimmunity in good and poor responder mice with mouse thyroglobulin and lipopolysaccharide. *J Fxp Med* 145:1250-63
23. Okamoto et al., 2009. Jagged-1 on dendritic cells and Notch on CD4+ T cells initiate lung allergic responsiveness by inducing IL-4 production. *J Immunol* 183: 2995-3003
24. Anastasi et al., 2003. Expression of activated Notch3 in transgenic mice enhances generation of T regulatory cells and protects against experimental autoimmune diabetes. *J Immunol* 171: 4504-11
25. Abbas et al., 1996. Functional diversity of helper T lymphocytes. *Nature* 383: 787-93
26. Campese et al., 2009. Notch3 and pTalpha/preTCR sustain the in vivo function of naturally occurring regulatory T cells. *International immunology* 21: 727-43
27. Vu et al., 2007. OX40 co-stimulation turns off Foxp3+ Tregs. *Blood* 110: 2501-10
28. Song et al., 2004. The co-stimulation-regulated duration of PKB activation controls T cell longevity. *Nat Immunol* 5: 150-8
29. Rogers et al., 2001. OX40 promotes Bcl-xL and Bcl-2 expression and is essential for long-term survival of CD4 T cells. *Immunity* 15: 445-55
30. So et al., 2011. OX40 complexes with phosphoinositide 3-kinase and protein kinase B (PKB) to augment TCR-dependent PKB signaling. *Journal of immunology* 186: 3547-55
31. Vacca et al., 2006. Notch3 and pre-TCR interaction unveils distinct NF-kappaB pathways in T-cell development and leukemia. *EMBO J* 25: 1000-8
32. Barbarulo et al., 2011. Notch3 and canonical NF-kappaB signaling pathways cooperatively regulate Foxp3 transcription. *J Immunol* 186: 6199-206
33. Samon et al., 2008. Notch1 and TGF-beta1 cooperatively regulate Foxp3 expression and the maintenance of peripheral regulatory T cells. *Blood* 112: 1813-21
34. Shevach et al., 2006. The lifestyle of naturally occurring CD4+CD25+ Foxp3+ regulatory T cells. *Immunological reviews* 212: 60-73
35. Allan et al., 2005. The role of 2 FOXP3 isoforms in the generation of human CD4+ Tregs. *The Journal of clinical investigation* 115: 3276-84
36. Sakaguchi, 2004. Naturally arising CD4+ regulatory t cells for immunologic self-tolerance and negative control of immune responses. *Annu Rev Immunol* 22: 531-62
37. Sakaguchi et al., 1985. Organ-specific autoimmune diseases induced in mice by elimination of T cell subset. I. Evidence for the active participation of T cells in natural self-tolerance; deficit of a T cell subset as a possible cause of autoimmune disease. *J Exp Med* 161: 72-87
38. Zwar et al., 2006. CD4+CD25+ regulatory T cells inhibit the antigen-dependent expansion of self-reactive T cells in vivo. *J Immunol* 176: 1609-17
39. Tang et al., 2004. In vitro-expanded antigen-specific regulatory T cells suppress autoimmune diabetes. *J Exp Med* 199: 1455-65
40. Joetham et al., 2009. Antigen specificity is not required for modulation of lung allergic responses by naturally occurring regulatory T cells. *J Immunol* 183: 1821-7
41. Stephens et al., 2009. Curing CNS autoimmune disease with myelin-reactive Foxp3+ Treg. *Eur J Immunol* 39, 1108-1117
42. Kieback et al., 2016. Thymus-Derived Regulatory T Cells Are Positively Selected on Natural Self-Antigen through Cognate Interactions of High Functional Avidity. *Immunity* 44: 1114-1126
43. Hoffmann et al., 2009. Loss of FOXP3 expression in natural human CD4+CD25+ regulatory T cells upon repetitive in vitro stimulation. *Eur. J Immunol* 39: 1088-1097
44. Wohlfert et al., 2011. GATA3 controls Foxp3(+) regulatory T cell fate during inflammation in mice. *J Clin Invest* 121: 4503-4515
45. Rudra et al., 2009. Runx-CBFbeta complexes control expression of the transcription factor Foxp3 in regulatory T cells. *Nat Immunol* 10: 1170-1177
46. VanValkenburgh et al., 2011. Critical role of Bc11b in suppressor function of T regulatory cells and prevention of inflammatory bowel disease. *J Exp Med* 208: 2069-2081
47. Fletcher et al., 2009. CD39+ Foxp3+ regulatory T Cells suppress pathogenic Th17 cells and are impaired in multiple sclerosis. *J Immunol* 183: 7602-7610
48. Joller et al., 2014. Treg cells expressing the coinhibitory molecule TIGIT selectively inhibit proinflammatory Th1 and Th17 cell responses *Immunity* 40: 569-581
49. Takatori et al., 2015. Helios Enhances Treg Cell Function in Cooperation With FoxP3. *Arthritis Rheumatol* 67: 1491-1502
50. Du et al., 2013. Foxp3+ Treg expanded from patients with established diabetes reduce Helios expression while retaining normal function compared to healthy individuals. *PLoS One* 8: e56209
51. Bresson et al., 2011. Antigen-specific prevention of type 1 diabetes in NOD mice is ameliorated by OX40 agonist treatment. *J Autoimmun* 37: 342-351
52. Haddad et al., 2016. Age-dependent divergent effects of OX40L treatment on the development of diabetes in NOD mice. *Autoimmunity* 49:1-14
53. Denes et al., 2010. Autoantigens plus interleukin-10 suppress diabetes autoimmunity. *Diabetes Technol Ther* 12: 649-661
54. Rapoport et al., 1993. Interleukin 4 reverses T cell proliferative unresponsiveness and prevents the onset of diabetes in nonobese diabetic mice. *J Exp Med* 178: 87-99
55. Zaccone et al., 1999. Interleukin-13 prevents autoimmune diabetes in NOD mice. *Diabetes* 48: 1522-1528
56. Piconese et al., 2010. A non-redundant role for OX40 in the competitive fitness of Treg in response to IL-2. *Eur J Immunol* 40: 2902-2913
57. Piconese et al., 2008. OX40 triggering blocks suppression by regulatory T cells and facilitates tumor rejection. *J Exp Med* 205: 825-839
58. Xiao et al., 2012. New insights on OX40 in the control of T cell immunity and immune tolerance in vivo. *J Immunol* 188: 892-901
59. Valzasina et al., 2005. Triggering of OX40 (CD134) on CD4(+)CD25+ T cells blocks their inhibitory activity: a novel regulatory role for OX40 and its comparison with GITR. *Blood* 105:2845-2851
60. Song et al., 2008. Activation of NF-kappaB1 by OX40 contributes to antigen-driven T cell expansion and survival. *J Immunol* 180: 7240-7248

61. Kawamata et al., 1998. Activation of OX40 signal transduction pathways leads to tumor necrosis factor receptor-associated factor (TRAF) 2- and TRAF5-mediated NF-kappaB activation. *J Biol Chem* 273: 5808-5814
62. So et al., 2011. Antigen-independent signalosome of CARMAI, PKCtheta, and TNF receptorassociated factor 2 (TRAF2) determines NF-kappaB signaling in T cells. *Proc Natl Acad Sci USA* 108: 2903-2908
63. Zorn et al., 2006. IL-2 regulates FOXP3 expression in human CD4+CD25+regulatory T cells through a STAT-dependent mechanism and induces the expansion of these cells in vivo. *Blood* 108: 1571-1579
64. Burchill et al., 2007. IL-2 receptor beta-dependent STAT5 activation is required for the development of Foxp3+ regulatory T cells. *J Immunol* 178: 280-290
65. Murawski et al., 2006. Upregulation of Foxp3 expression in mouse and human Treg is IL-2/STAT5 dependent: implications for the NOD STAT5B mutation in diabetes pathogenesis. *Ann N Y Acad Sci* 1079: 198-204
66. Lai et al., 2009. Epigenetic regulation of Foxp3 expression in regulatory T cells by DNA methylation. *J Immunol* 182:259-273
67. Mahmud et al., 2013. Interleukin-2 and STAT5 in regulatory T cell development and function. *JAKSIAT* 2: e23154
68. Gopisetty et al., 2013. OX40L/Jagged1 cosignaling by GM-CSF-induced bone marrow-derived dendritic cells is required for the expansion of functional regulatory T cells. *J Immunol* 190:5516-5525
69. Charbonnier et al., 2015. Control of peripheral tolerance by regulatory T cell-intrinsic Notch signaling. *Nat Immunol* 16: 1162-1173
70. Shimizu et al., 1999. Mouse jagged1 physically interacts with notch2 and other notch receptors. Assessment by quantitative methods. *J Biol Chem* 274: 32961-32969
71. Choi et al., 2008. Jagged-1 and Notch3 juxtacrine loop regulates ovarian tumor growth and adhesion. *Cancer Res* 68: 5716-5723

Various changes and modifications to the disclosed embodiments will be apparent to those skilled in the art. Such changes and modifications may be made without departing from the spirit and scope thereof.

---

The invention claimed is:

1. A method of treating systemic lupus erythematosus in a patient in need of such treatment comprising administering to the patient a therapeutically effective amount of soluble OX40L and soluble Jagged-1 wherein the soluble OX40L comprises the amino acid sequence set forth in any one of SEQ ID NOs: 51 and 54, and wherein the soluble Jagged-1 comprises the amino acid sequence set forth in any one of SEQ ID NOs:61 and 63.

2. The method of claim 1, wherein the OX40L and Jagged-1 are recombinantly produced.

3. The method of claim 1, wherein the patient is a human patient.

* * * * *

UNITED STATES PATENT AND TRADEMARK OFFICE
CERTIFICATE OF CORRECTION

PATENT NO. : 11,873,510 B2
APPLICATION NO. : 16/879923
DATED : January 16, 2024
INVENTOR(S) : Bellur Prabhakar It is certified that error appears in the above-identified patent and that said Letters Patent is hereby corrected as shown below:

In the Specification

Column 1, Lines 3-7 – "This application claims priority to U.S. patent application Ser. No. 14/186,766 filed Feb. 21, 2014, which claims priority to U.S. Provisional Patent application 61/768,204 filed Feb. 22, 2013, the contents of which are incorporated herein by reference in the entirety" should be "This application claims priority to U.S. patent application Ser. No. 15/803,232 filed November 3, 2017, which claims priority to U.S. patent application Ser. No. 14/186,766 filed Feb. 21, 2014, which claims priority to U.S. Provisional Patent application 61/768,204 filed Feb. 22, 2013, the contents of which are incorporated herein by reference in the entirety.";
Column 2, Line 60 – "OX40L'" should be "OX40L+";
Column 3, Line 67 – "CD4'" should be "CD4+";
Column 6, Line 23 – "OX40LJAG1" should be "OX40L-JAG1";
Column 6, Line 51 – "OX40 L" should be "OX40L";
Column 10, Line 34 – "CD4'CD25+" should be "CD4+CD25+";
Column 11, Line 34 – "OX40L*GM-BMDC" should be "OX40L+GM-BMDC";
Column 13, Line 63 – "1×106/ml" should be "1×10^6 cells/ml";
Column 14, Line 5 – "CD4+CD25+" should be "CD4$^+$CD25F$^+$";
Column 14, Line 10 – "IOU/ml" should be "10 U/ml"; and
Column 28, Lines 5-6 – "phospo-NF-uBp65" should be "phospo-NF-κBp65".

Signed and Sealed this
First Day of October, 2024

*Katherine Kelly Vidal*

Katherine Kelly Vidal
*Director of the United States Patent and Trademark Office*

SEQUENCE LISTING

<160> NUMBER OF SEQ ID NOS: 70

<210> SEQ ID NO 1
<211> LENGTH: 25
<212> TYPE: DNA
<213> ORGANISM: Artificial Sequence
<220> FEATURE:
<223> OTHER INFORMATION: HPRT - Forward primer

<400> SEQUENCE: 1
gttggataca ggccagactt tgttg                                              25

<210> SEQ ID NO 2
<211> LENGTH: 23
<212> TYPE: DNA
<213> ORGANISM: Artificial Sequence
<220> FEATURE:
<223> OTHER INFORMATION: HPRT - Reverse primer

<400> SEQUENCE: 2
tactaggcag atggccagga cta                                                23

<210> SEQ ID NO 3
<211> LENGTH: 21
<212> TYPE: DNA
<213> ORGANISM: Artificial Sequence
<220> FEATURE:
<223> OTHER INFORMATION: Notch1 - Forward primer

<400> SEQUENCE: 3
tgttaatgag tgcatctcca a                                                  21

<210> SEQ ID NO 4
<211> LENGTH: 23
<212> TYPE: DNA
<213> ORGANISM: Artificial Sequence
<220> FEATURE:
<223> OTHER INFORMATION: Notch1 - Reverse primer

<400> SEQUENCE: 4
cattcgtagc catcaatctt gtc                                                23

<210> SEQ ID NO 5

-continued

```
<211> LENGTH: 22
<212> TYPE: DNA
<213> ORGANISM: Artificial Sequence
<220> FEATURE:
<223> OTHER INFORMATION: Notch2 - Forward primer

<400> SEQUENCE: 5
tggaggtaaa tgaatgccag ag                                              22

<210> SEQ ID NO 6
<211> LENGTH: 19
<212> TYPE: DNA
<213> ORGANISM: Artificial Sequence
<220> FEATURE:
<223> OTHER INFORMATION: Notch2 - Reverse primer

<400> SEQUENCE: 6
tgtagcgatt gatgccgtc                                                  19

<210> SEQ ID NO 7
<211> LENGTH: 18
<212> TYPE: DNA
<213> ORGANISM: Artificial Sequence
<220> FEATURE:
<223> OTHER INFORMATION: Notch3 - Forward primer

<400> SEQUENCE: 7
acactgggag ttctctgt                                                   18

<210> SEQ ID NO 8
<211> LENGTH: 18
<212> TYPE: DNA
<213> ORGANISM: Artificial Sequence
<220> FEATURE:
<223> OTHER INFORMATION: Notch3 - Reverse primer

<400> SEQUENCE: 8
gtctgctggc atgggata                                                   18

<210> SEQ ID NO 9
<211> LENGTH: 22
<212> TYPE: DNA
<213> ORGANISM: Artificial Sequence
<220> FEATURE:
<223> OTHER INFORMATION: Notch4 - Forward primer

<400> SEQUENCE: 9
cacctcctgc cataacacct tg                                              22

<210> SEQ ID NO 10
<211> LENGTH: 25
<212> TYPE: DNA
<213> ORGANISM: Artificial Sequence
<220> FEATURE:
<223> OTHER INFORMATION: Notch4 - Reverse primer

<400> SEQUENCE: 10
acacagtcat ctgggttcat ctcac                                           25

<210> SEQ ID NO 11
<211> LENGTH: 22
<212> TYPE: DNA
<213> ORGANISM: Artificial Sequence
<220> FEATURE:
<223> OTHER INFORMATION: Foxp3 - Forward primer

<400> SEQUENCE: 11
```

-continued cgaacatgcg agtaaaccaa tg                                            22

<210> SEQ ID NO 12
<211> LENGTH: 21
<212> TYPE: DNA
<213> ORGANISM: Artificial Sequence
<220> FEATURE:
<223> OTHER INFORMATION: Foxp3 - Reverse primer

<400> SEQUENCE: 12
ctttcaccta tgccacccgtt a                                            21

<210> SEQ ID NO 13
<211> LENGTH: 23
<212> TYPE: DNA
<213> ORGANISM: Artificial Sequence
<220> FEATURE:
<223> OTHER INFORMATION: GAPDH - Forward primer

<400> SEQUENCE: 13
gtggagtcat actggaacat gta                                           23

<210> SEQ ID NO 14
<211> LENGTH: 19
<212> TYPE: DNA
<213> ORGANISM: Artificial Sequence
<220> FEATURE:
<223> OTHER INFORMATION: GAPDH - Reverse primer

<400> SEQUENCE: 14
aatggtgaag gtcggtgtg                                                19

<210> SEQ ID NO 15
<211> LENGTH: 21
<212> TYPE: DNA
<213> ORGANISM: Artificial Sequence
<220> FEATURE:
<223> OTHER INFORMATION: Notch3 - Forward primer

<400> SEQUENCE: 15
agtgccgatc tggtacaact t                                             21

<210> SEQ ID NO 16
<211> LENGTH: 20
<212> TYPE: DNA
<213> ORGANISM: Artificial Sequence
<220> FEATURE:
<223> OTHER INFORMATION: Notch3 - Reverse primer

<400> SEQUENCE: 16
cactacgggg ttctcacaca                                               20

<210> SEQ ID NO 17
<211> LENGTH: 23
<212> TYPE: DNA
<213> ORGANISM: Artificial Sequence
<220> FEATURE:
<223> OTHER INFORMATION: Prkcq - Forward primer

<400> SEQUENCE: 17
tatccaactt tgactgtggg acc                                           23

<210> SEQ ID NO 18
<211> LENGTH: 21
<212> TYPE: DNA

```
<213> ORGANISM: Artificial Sequence
<220> FEATURE:
<223> OTHER INFORMATION: Prkcq - Reverse primer

<400> SEQUENCE: 18
cccttccctt gttaatgtgg g                                          21

<210> SEQ ID NO 19
<211> LENGTH: 21
<212> TYPE: DNA
<213> ORGANISM: Artificial Sequence
<220> FEATURE:
<223> OTHER INFORMATION: NF-KB1 - Forward primer

<400> SEQUENCE: 19
atggcagacg atgatcccta c                                          21

<210> SEQ ID NO 20
<211> LENGTH: 23
<212> TYPE: DNA
<213> ORGANISM: Artificial Sequence
<220> FEATURE:
<223> OTHER INFORMATION: NF-KB1 - Reverse primer

<400> SEQUENCE: 20
tgttgacagt ggtatttctg gtg                                        23

<210> SEQ ID NO 21
<211> LENGTH: 22
<212> TYPE: DNA
<213> ORGANISM: Artificial Sequence
<220> FEATURE:
<223> OTHER INFORMATION: NF-KB2 - Forward primer

<400> SEQUENCE: 21
ggccggaaag acctatccta ct                                         22

<210> SEQ ID NO 22
<211> LENGTH: 20
<212> TYPE: DNA
<213> ORGANISM: Artificial Sequence
<220> FEATURE:
<223> OTHER INFORMATION: NF-KB2 - Reverse primer

<400> SEQUENCE: 22
ctacagacac agcgcacact                                            20

<210> SEQ ID NO 23
<211> LENGTH: 22
<212> TYPE: DNA
<213> ORGANISM: Artificial Sequence
<220> FEATURE:
<223> OTHER INFORMATION: Il-2ra - Forward primer

<400> SEQUENCE: 23
aaccatagta cccagttgtc gg                                         22

<210> SEQ ID NO 24
<211> LENGTH: 23
<212> TYPE: DNA
<213> ORGANISM: Artificial Sequence
<220> FEATURE:
<223> OTHER INFORMATION: Il-2ra - Reverse primer

<400> SEQUENCE: 24
tcctaagcaa cgcatataga cca                                        23
```

<210> SEQ ID NO 25
<211> LENGTH: 22
<212> TYPE: DNA
<213> ORGANISM: Artificial Sequence
<220> FEATURE:
<223> OTHER INFORMATION: Nras - Forward primer

<400> SEQUENCE: 25
actgagtaca aactggtggt gg                                          22

<210> SEQ ID NO 26
<211> LENGTH: 23
<212> TYPE: DNA
<213> ORGANISM: Artificial Sequence
<220> FEATURE:
<223> OTHER INFORMATION: Nras - Reverse primer

<400> SEQUENCE: 26
tcggtaagaa tcctctatgg tgg                                         23

<210> SEQ ID NO 27
<211> LENGTH: 20
<212> TYPE: DNA
<213> ORGANISM: Artificial Sequence
<220> FEATURE:
<223> OTHER INFORMATION: Dlgap5 - Forward primer

<400> SEQUENCE: 27
gtgtcacgtt ttgccagtcg                                             20

<210> SEQ ID NO 28
<211> LENGTH: 21
<212> TYPE: DNA
<213> ORGANISM: Artificial Sequence
<220> FEATURE:
<223> OTHER INFORMATION: Dlgap5 - Reverse primer

<400> SEQUENCE: 28
tctgtttcgc tcatacaccc t                                           21

<210> SEQ ID NO 29
<211> LENGTH: 21
<212> TYPE: DNA
<213> ORGANISM: Artificial Sequence
<220> FEATURE:
<223> OTHER INFORMATION: OX40 - Forward primer

<400> SEQUENCE: 29
tacctacccc agtggtcaca a                                           21

<210> SEQ ID NO 30
<211> LENGTH: 23
<212> TYPE: DNA
<213> ORGANISM: Artificial Sequence
<220> FEATURE:
<223> OTHER INFORMATION: OX40 - Reverse primer

<400> SEQUENCE: 30
acggatgaca tagagtatcc ctg                                         23

<210> SEQ ID NO 31
<211> LENGTH: 21
<212> TYPE: DNA
<213> ORGANISM: Artificial Sequence
<220> FEATURE:

<223> OTHER INFORMATION: Bcl10 - Forward primer

<400> SEQUENCE: 31
accaacaacc tctctaggtg c                                           21

<210> SEQ ID NO 32
<211> LENGTH: 20
<212> TYPE: DNA
<213> ORGANISM: Artificial Sequence
<220> FEATURE:
<223> OTHER INFORMATION: Bcl10 - Reverse primer

<400> SEQUENCE: 32
ccctccgggt gggtacatga                                             20

<210> SEQ ID NO 33
<211> LENGTH: 21
<212> TYPE: DNA
<213> ORGANISM: Artificial Sequence
<220> FEATURE:
<223> OTHER INFORMATION: IFN-Gamma - Forward primer

<400> SEQUENCE: 33
atgaacgcta cacactgcat c                                           21

<210> SEQ ID NO 34
<211> LENGTH: 21
<212> TYPE: DNA
<213> ORGANISM: Artificial Sequence
<220> FEATURE:
<223> OTHER INFORMATION: IFN-Gamma - Revers primer

<400> SEQUENCE: 34
ccatcctttt gccagttcct c                                           21

<210> SEQ ID NO 35
<211> LENGTH: 20
<212> TYPE: DNA
<213> ORGANISM: Artificial Sequence
<220> FEATURE:
<223> OTHER INFORMATION: IL-12alpha - Forward primer

<400> SEQUENCE: 35
cccttgccct cctaaaccac                                             20

<210> SEQ ID NO 36
<211> LENGTH: 23
<212> TYPE: DNA
<213> ORGANISM: Artificial Sequence
<220> FEATURE:
<223> OTHER INFORMATION: IL-12alpha - Reverse primer

<400> SEQUENCE: 36
aaggaaccct tagagtgctt act                                         23

<210> SEQ ID NO 37
<211> LENGTH: 21
<212> TYPE: DNA
<213> ORGANISM: Artificial Sequence
<220> FEATURE:
<223> OTHER INFORMATION: IL-12beta - Forward primer

<400> SEQUENCE: 37
tggtttgcca tcgttttgct g                                           21

```
<210> SEQ ID NO 38
<211> LENGTH: 22
<212> TYPE: DNA
<213> ORGANISM: Artificial Sequence
<220> FEATURE:
<223> OTHER INFORMATION: IL-12beta - Reverse primer

<400> SEQUENCE: 38
acaggtgagg ttcactgttt ct                                              22

<210> SEQ ID NO 39
<211> LENGTH: 23
<212> TYPE: DNA
<213> ORGANISM: Artificial Sequence
<220> FEATURE:
<223> OTHER INFORMATION: TNF-alpha - Forward primer

<400> SEQUENCE: 39
ccctcacact cagatcatct tct                                             23

<210> SEQ ID NO 40
<211> LENGTH: 19
<212> TYPE: DNA
<213> ORGANISM: Artificial Sequence
<220> FEATURE:
<223> OTHER INFORMATION: TNF-alpha - Reverse primer

<400> SEQUENCE: 40
gctacgacgt gggctacag                                                  19

<210> SEQ ID NO 41
<211> LENGTH: 20
<212> TYPE: DNA
<213> ORGANISM: Artificial Sequence
<220> FEATURE:
<223> OTHER INFORMATION: IL-4 - Forward primer

<400> SEQUENCE: 41
ggtctcaacc cccagctagt                                                 20

<210> SEQ ID NO 42
<211> LENGTH: 23
<212> TYPE: DNA
<213> ORGANISM: Artificial Sequence
<220> FEATURE:
<223> OTHER INFORMATION: IL-4 - Reverse primer

<400> SEQUENCE: 42
gccgatgatc tctctcaagt gat                                             23

<210> SEQ ID NO 43
<211> LENGTH: 23
<212> TYPE: DNA
<213> ORGANISM: Artificial Sequence
<220> FEATURE:
<223> OTHER INFORMATION: IL-5 - Forward primer

<400> SEQUENCE: 43
ctctgttgac aagcaatgag acg                                             23

<210> SEQ ID NO 44
<211> LENGTH: 22
<212> TYPE: DNA
<213> ORGANISM: Artificial Sequence
<220> FEATURE:
<223> OTHER INFORMATION: IL-5 - Reverse primer
```

<400> SEQUENCE: 44
tcttcagtat gtctagcccc tg                                          22

<210> SEQ ID NO 45
<211> LENGTH: 19
<212> TYPE: DNA
<213> ORGANISM: Artificial Sequence
<220> FEATURE:
<223> OTHER INFORMATION: IL-13 - Forward primer

<400> SEQUENCE: 45
cctggctctt gcttgccttt                                             19

<210> SEQ ID NO 46
<211> LENGTH: 21
<212> TYPE: DNA
<213> ORGANISM: Artificial Sequence
<220> FEATURE:
<223> OTHER INFORMATION: IL-13 - Reverse primer

<400> SEQUENCE: 46
ggtcttgtgt gatgttgctc a                                           21

<210> SEQ ID NO 47
<211> LENGTH: 23
<212> TYPE: DNA
<213> ORGANISM: Artificial Sequence
<220> FEATURE:
<223> OTHER INFORMATION: IL-6 - Forward primer

<400> SEQUENCE: 47
tagtccttcc tacccaatt tcc                                          23

<210> SEQ ID NO 48
<211> LENGTH: 21
<212> TYPE: DNA
<213> ORGANISM: Artificial Sequence
<220> FEATURE:
<223> OTHER INFORMATION: IL-6 - Reverse primer

<400> SEQUENCE: 48
ttggtcctta gccactcctt c                                           21

<210> SEQ ID NO 49
<211> LENGTH: 21
<212> TYPE: DNA
<213> ORGANISM: Artificial Sequence
<220> FEATURE:
<223> OTHER INFORMATION: IL-17 - Forward primer

<400> SEQUENCE: 49
tttaactccc ttggcgcaaa a                                           21

<210> SEQ ID NO 50
<211> LENGTH: 20
<212> TYPE: DNA
<213> ORGANISM: Artificial Sequence
<220> FEATURE:
<223> OTHER INFORMATION: IL-17 - Reverse primer

<400> SEQUENCE: 50
ctttccctcc gcattgacac                                             20

<210> SEQ ID NO 51
<211> LENGTH: 941

<212> TYPE: PRT
<213> ORGANISM: Artificial Sequence
<220> FEATURE:
<223> OTHER INFORMATION: Human OX40L trimer

<400> SEQUENCE: 51

```
Met Glu Phe Gly Leu Ser Trp Val Phe Leu Val Ala Leu Phe Arg Gly
1               5                   10                  15

Val Gln Cys His His His His His His His His Thr Thr Ala
            20                  25                  30

Pro Ser Ala Gln Leu Glu Lys Glu Leu Gln Ala Leu Glu Lys Glu Asn
            35                  40                  45

Ala Gln Leu Glu Trp Glu Leu Gln Ala Leu Glu Lys Glu Leu Ala Gln
50                  55                  60

Ala Ala Ser Gly Gly Gly Gly Ser Asp Lys Thr His Thr Cys Pro
65                  70                  75                  80

Pro Cys Pro Leu Ile Ala Leu Ala Glu Glu Val Arg Lys Leu Lys Ala
                85                  90                  95

Arg Val Asp Glu Leu Glu Arg Ile Arg Arg Ser Ile Gly Gly Gly Gly
            100                 105                 110

Gly Ser Gln Val Ser His Arg Tyr Pro Arg Gln Val Ser His Arg Tyr
        115                 120                 125

Pro Arg Ile Gln Ser Ile Lys Val Gln Phe Thr Glu Tyr Lys Lys Glu
130                 135                 140

Lys Gly Phe Ile Leu Thr Ser Gln Lys Glu Asp Glu Ile Met Lys Val
145                 150                 155                 160

Gln Asn Asn Ser Val Ile Ile Asn Cys Asp Gly Phe Tyr Leu Ile Ser
                165                 170                 175

Leu Lys Gly Tyr Phe Ser Gln Glu Val Asn Ile Ser Leu His Tyr Gln
            180                 185                 190

Lys Asp Glu Glu Pro Leu Phe Gln Leu Lys Lys Val Arg Ser Val Asn
        195                 200                 205

Ser Leu Met Val Ala Ser Leu Thr Tyr Lys Asp Lys Val Tyr Leu Asn
210                 215                 220

Val Thr Thr Asp Asn Thr Ser Leu Asp Asp Phe His Val Asn Gly Gly
225                 230                 235                 240

Glu Leu Ile Leu Ile His Gln Asn Pro Gly Glu Phe Cys Val Leu
                245                 250                 255

Ser Gly Ala Thr Asn Phe Ser Leu Leu Lys Gln Ala Gly Asp Val Glu
            260                 265                 270

Glu Asn Pro Gly Pro Met Glu Phe Gly Leu Ser Trp Val Phe Leu Val
        275                 280                 285

Ala Leu Phe Arg Gly Val Gln Cys Leu Ile Ala Leu Ala Glu Glu Val
290                 295                 300

Arg Lys Leu Lys Ala Arg Val Asp Glu Leu Glu Arg Ile Arg Arg Ser
305                 310                 315                 320

Ile Gly Gly Gly Gly Gly Ser Gln Val Ser His Arg Tyr Pro Arg Gln
                325                 330                 335

Val Ser His Arg Tyr Pro Arg Ile Gln Ser Ile Lys Val Gln Phe Thr
            340                 345                 350

Glu Tyr Lys Lys Glu Lys Gly Phe Ile Leu Thr Ser Gln Lys Glu Asp
        355                 360                 365

Glu Ile Met Lys Val Gln Asn Asn Ser Val Ile Ile Asn Cys Asp Gly
370                 375                 380
```

```
Phe Tyr Leu Ile Ser Leu Lys Gly Tyr Phe Gln Glu Val Asn Ile
385                 390                 395                 400

Ser Leu His Tyr Gln Lys Asp Glu Glu Pro Leu Phe Gln Leu Lys Lys
            405                 410                 415

Val Arg Ser Val Asn Ser Leu Met Val Ala Ser Leu Thr Tyr Lys Asp
        420                 425                 430

Lys Val Tyr Leu Asn Val Thr Thr Asp Asn Thr Ser Leu Asp Asp Phe
            435                 440                 445

His Val Asn Gly Gly Glu Leu Ile Leu Ile His Gln Asn Pro Gly Glu
        450                 455                 460

Phe Cys Val Leu Gly Ser Gly Ala Thr Asn Phe Ser Leu Leu Lys Gln
465                 470                 475                 480

Ala Gly Asp Val Glu Glu Asn Pro Gly Pro Met Glu Phe Gly Leu Ser
            485                 490                 495

Trp Val Phe Leu Val Ala Leu Phe Arg Gly Val Gln Cys Leu Ile Ala
        500                 505                 510

Leu Ala Glu Glu Val Arg Lys Leu Lys Ala Arg Val Asp Glu Leu Glu
        515                 520                 525

Arg Ile Arg Arg Ser Ile Gly Gly Gly Gly Ser Gln Val Ser His
530                 535                 540

Arg Tyr Pro Arg Gln Val Ser His Arg Tyr Pro Arg Ile Gln Ser Ile
545                 550                 555                 560

Lys Val Gln Phe Thr Glu Tyr Lys Lys Glu Lys Gly Phe Ile Leu Thr
            565                 570                 575

Ser Gln Lys Glu Asp Glu Ile Met Lys Val Gln Asn Asn Ser Val Ile
        580                 585                 590

Ile Asn Cys Asp Gly Phe Tyr Leu Ile Ser Leu Lys Gly Tyr Phe Ser
        595                 600                 605

Gln Glu Val Asn Ile Ser Leu His Tyr Gln Lys Asp Glu Glu Pro Leu
610                 615                 620

Phe Gln Leu Lys Lys Val Arg Ser Val Asn Ser Leu Met Val Ala Ser
625                 630                 635                 640

Leu Thr Tyr Lys Asp Lys Val Tyr Leu Asn Val Thr Thr Asp Asn Thr
            645                 650                 655

Ser Leu Asp Asp Phe His Val Asn Gly Gly Glu Leu Ile Leu Ile His
        660                 665                 670

Gln Asn Pro Gly Glu Phe Cys Val Leu Gly Ser Gly Glu Gly Arg Gly
        675                 680                 685

Ser Leu Leu Thr Cys Gly Asp Val Glu Glu Asn Pro Gly Pro Met Val
        690                 695                 700

Ser Lys Gly Glu Glu Leu Phe Thr Gly Val Val Pro Ile Leu Val Glu
705                 710                 715                 720

Leu Asp Gly Asp Val Asn Gly His Lys Phe Ser Val Ser Gly Glu Gly
            725                 730                 735

Glu Gly Asp Ala Thr Tyr Gly Lys Leu Thr Leu Lys Phe Ile Cys Thr
        740                 745                 750

Thr Gly Lys Leu Pro Val Pro Trp Pro Thr Leu Val Thr Thr Leu Thr
        755                 760                 765

Tyr Gly Val Gln Cys Phe Ser Arg Tyr Pro Asp His Met Lys Gln His
        770                 775                 780

Asp Phe Phe Lys Ser Ala Met Pro Glu Gly Tyr Val Gln Glu Arg Thr
785                 790                 795                 800

Ile Phe Phe Lys Asp Asp Gly Asn Tyr Lys Thr Arg Ala Glu Val Lys
```

```
                    805                 810                 815
Phe Glu Gly Asp Thr Leu Val Asn Arg Ile Glu Leu Lys Gly Ile Asp
                820                 825                 830

Phe Lys Glu Asp Gly Asn Ile Leu Gly His Lys Leu Glu Tyr Asn Tyr
            835                 840                 845

Asn Ser His Asn Val Tyr Ile Met Ala Asp Lys Gln Lys Asn Gly Ile
        850                 855                 860

Lys Val Asn Phe Lys Ile Arg His Asn Ile Glu Asp Gly Ser Val Gln
865                 870                 875                 880

Leu Ala Asp His Tyr Gln Gln Asn Thr Pro Ile Gly Asp Gly Pro Val
                885                 890                 895

Leu Leu Pro Asp Asn His Tyr Leu Ser Thr Gln Ser Ala Leu Ser Lys
            900                 905                 910

Asp Pro Asn Glu Lys Arg Asp His Met Val Leu Leu Glu Phe Val Thr
        915                 920                 925

Ala Ala Gly Ile Thr Leu Gly Met Asp Glu Leu Tyr Lys
    930                 935                 940

<210> SEQ ID NO 52
<211> LENGTH: 992
<212> TYPE: PRT
<213> ORGANISM: Artificial Sequence
<220> FEATURE:
<223> OTHER INFORMATION: Mouse OX40L trimer

<400> SEQUENCE: 52

Met Glu Phe Gly Leu Ser Trp Val Phe Leu Val Ala Leu Phe Arg Gly
1               5                   10                  15

Val Gln Cys His His His His His His His His Thr Thr Ala
            20                  25                  30

Pro Ser Ala Gln Leu Glu Lys Glu Leu Gln Ala Leu Glu Lys Glu Asn
        35                  40                  45

Ala Gln Leu Glu Trp Glu Leu Gln Ala Leu Glu Lys Glu Leu Ala Gln
    50                  55                  60

Ala Ala Ser Gly Gly Gly Gly Ser Asp Lys Thr His Thr Cys Pro
65                  70                  75                  80

Pro Cys Pro Leu Ile Ala Leu Ala Glu Glu Val Arg Lys Leu Lys Ala
                85                  90                  95

Arg Val Asp Glu Leu Glu Arg Ile Arg Arg Ser Ile Gly Gly Gly Gly
            100                 105                 110

Gly Ser Gln Val Ser His Arg Tyr Pro Arg Gln Leu Ser Ser Ser Pro
        115                 120                 125

Ala Lys Asp Pro Pro Ile Gln Arg Leu Arg Gly Ala Val Thr Arg Cys
    130                 135                 140

Glu Asp Gly Gln Leu Phe Ile Ser Ser Tyr Lys Asn Glu Tyr Gln Thr
145                 150                 155                 160

Met Glu Val Gln Asn Asn Ser Val Val Ile Lys Cys Asp Gly Leu Tyr
                165                 170                 175

Ile Ile Tyr Leu Lys Gly Ser Phe Phe Gln Glu Val Lys Ile Asp Leu
            180                 185                 190

His Phe Arg Glu Asp His Asn Pro Ile Ser Ile Pro Met Leu Asn Asp
        195                 200                 205

Gly Arg Arg Ile Val Phe Thr Val Val Ala Ser Leu Ala Phe Lys Asp
    210                 215                 220

Lys Val Tyr Leu Thr Val Asn Ala Pro Asp Thr Leu Cys Glu His Leu
```

```
            225                 230                 235                 240
Gln Ile Asn Asp Gly Glu Leu Ile Val Val Gln Leu Thr Pro Gly Tyr
                    245                 250                 255
Cys Ala Pro Glu Gly Ser Tyr His Ser Thr Val Asn Gln Val Pro Leu
                    260                 265                 270
Gly Ser Gly Ala Thr Asn Phe Ser Leu Leu Lys Gln Ala Gly Asp Val
                    275                 280                 285
Glu Glu Asn Pro Gly Pro Met Glu Phe Gly Leu Ser Trp Val Phe Leu
            290                 295                 300
Val Ala Leu Phe Arg Gly Val Gln Cys Leu Ile Ala Leu Ala Glu Glu
305                 310                 315                 320
Val Arg Lys Leu Lys Ala Arg Val Asp Glu Leu Glu Arg Ile Arg Arg
                    325                 330                 335
Ser Ile Gly Gly Gly Gly Ser Gln Val Ser His Arg Tyr Pro Arg
                    340                 345                 350
Gln Leu Ser Ser Pro Ala Lys Asp Pro Pro Ile Gln Arg Leu Arg
            355                 360                 365
Gly Ala Val Thr Arg Cys Glu Asp Gly Gln Leu Phe Ile Ser Ser Tyr
            370                 375                 380
Lys Asn Glu Tyr Gln Thr Met Glu Val Gln Asn Asn Ser Val Val Ile
385                 390                 395                 400
Lys Cys Asp Gly Leu Tyr Ile Ile Tyr Leu Lys Gly Ser Phe Phe Gln
                    405                 410                 415
Glu Val Lys Ile Asp Leu His Phe Arg Glu Asp His Asn Pro Ile Ser
                    420                 425                 430
Ile Pro Met Leu Asn Asp Gly Arg Arg Ile Val Phe Thr Val Val Ala
            435                 440                 445
Ser Leu Ala Phe Lys Asp Lys Val Tyr Leu Thr Val Asn Ala Pro Asp
            450                 455                 460
Thr Leu Cys Glu His Leu Gln Ile Asn Asp Gly Glu Leu Ile Val Val
465                 470                 475                 480
Gln Leu Thr Pro Gly Tyr Cys Ala Pro Glu Gly Ser Tyr His Ser Thr
                    485                 490                 495
Val Asn Gln Val Pro Leu Gly Ser Gly Ala Thr Asn Phe Ser Leu Leu
                    500                 505                 510
Lys Gln Ala Gly Asp Val Glu Glu Asn Pro Gly Pro Met Glu Phe Gly
            515                 520                 525
Leu Ser Trp Val Phe Leu Val Ala Leu Phe Arg Gly Val Gln Cys Leu
            530                 535                 540
Ile Ala Leu Ala Glu Glu Val Arg Lys Leu Lys Ala Arg Val Asp Glu
545                 550                 555                 560
Leu Glu Arg Ile Arg Arg Ser Ile Gly Gly Gly Gly Ser Gln Val
                    565                 570                 575
Ser His Arg Tyr Pro Arg Gln Leu Ser Ser Pro Ala Lys Asp Pro
            580                 585                 590
Pro Ile Gln Arg Leu Arg Gly Ala Val Thr Arg Cys Glu Asp Gly Gln
            595                 600                 605
Leu Phe Ile Ser Ser Tyr Lys Asn Glu Tyr Gln Thr Met Glu Val Gln
            610                 615                 620
Asn Asn Ser Val Val Ile Lys Cys Asp Gly Leu Tyr Ile Ile Tyr Leu
625                 630                 635                 640
Lys Gly Ser Phe Phe Gln Glu Val Lys Ile Asp Leu His Phe Arg Glu
                    645                 650                 655
```

```
Asp His Asn Pro Ile Ser Ile Pro Met Leu Asn Asp Gly Arg Arg Ile
            660                 665                 670

Val Phe Thr Val Val Ala Ser Leu Ala Phe Lys Asp Lys Val Tyr Leu
        675                 680                 685

Thr Val Asn Ala Pro Asp Thr Leu Cys Glu His Leu Gln Ile Asn Asp
    690                 695                 700

Gly Glu Leu Ile Val Val Gln Leu Thr Pro Gly Tyr Cys Ala Pro Glu
705                 710                 715                 720

Gly Ser Tyr His Ser Thr Val Asn Gln Val Pro Leu Gly Ser Gly Glu
                725                 730                 735

Gly Arg Gly Ser Leu Leu Thr Cys Gly Asp Val Glu Glu Asn Pro Gly
            740                 745                 750

Pro Met Val Ser Lys Gly Glu Glu Leu Phe Thr Gly Val Val Pro Ile
        755                 760                 765

Leu Val Glu Leu Asp Gly Asp Val Asn Gly His Lys Phe Ser Val Ser
    770                 775                 780

Gly Glu Gly Glu Gly Asp Ala Thr Tyr Gly Lys Leu Thr Leu Lys Phe
785                 790                 795                 800

Ile Cys Thr Thr Gly Lys Leu Pro Val Pro Trp Pro Thr Leu Val Thr
                805                 810                 815

Thr Leu Thr Tyr Gly Val Gln Cys Phe Ser Arg Tyr Pro Asp His Met
            820                 825                 830

Lys Gln His Asp Phe Phe Lys Ser Ala Met Pro Glu Gly Tyr Val Gln
        835                 840                 845

Glu Arg Thr Ile Phe Phe Lys Asp Asp Gly Asn Tyr Lys Thr Arg Ala
    850                 855                 860

Glu Val Lys Phe Glu Gly Asp Thr Leu Val Asn Arg Ile Glu Leu Lys
865                 870                 875                 880

Gly Ile Asp Phe Lys Glu Asp Gly Asn Ile Leu Gly His Lys Leu Glu
                885                 890                 895

Tyr Asn Tyr Asn Ser His Asn Val Tyr Ile Met Ala Asp Lys Gln Lys
            900                 905                 910

Asn Gly Ile Lys Val Asn Phe Lys Ile Arg His Asn Ile Glu Asp Gly
        915                 920                 925

Ser Val Gln Leu Ala Asp His Tyr Gln Gln Asn Thr Pro Ile Gly Asp
    930                 935                 940

Gly Pro Val Leu Leu Pro Asp Asn His Tyr Leu Ser Thr Gln Ser Ala
945                 950                 955                 960

Leu Ser Lys Asp Pro Asn Glu Lys Arg Asp His Met Val Leu Leu Glu
                965                 970                 975

Phe Val Thr Ala Ala Gly Ile Thr Leu Gly Met Asp Glu Leu Tyr Lys
            980                 985                 990

<210> SEQ ID NO 53
<211> LENGTH: 901
<212> TYPE: PRT
<213> ORGANISM: Artificial Sequence
<220> FEATURE:
<223> OTHER INFORMATION: Mouse OX40L without trimerization motif

<400> SEQUENCE: 53

Met Glu Phe Gly Leu Ser Trp Val Phe Leu Val Ala Leu Phe Arg Gly
1               5                   10                  15

Val Gln Cys His His His His His His His His Thr Thr Ala
            20                  25                  30
```

```
Pro Ser Ala Gln Leu Glu Lys Glu Leu Gln Ala Leu Glu Lys Glu Asn
        35                  40                  45
Ala Gln Leu Glu Trp Glu Leu Gln Ala Leu Glu Lys Glu Leu Ala Gln
 50                  55                  60
Ala Ala Ser Gly Gly Gly Gly Ser Gln Val Ser His Arg Tyr Pro
 65                  70                  75                  80
Arg Gln Leu Ser Ser Pro Ala Lys Asp Pro Pro Ile Gln Arg Leu
                 85                  90                  95
Arg Gly Ala Val Thr Arg Cys Glu Asp Gly Gln Leu Phe Ile Ser Ser
                100                 105                 110
Tyr Lys Asn Glu Tyr Gln Thr Met Glu Val Gln Asn Asn Ser Val Val
        115                 120                 125
Ile Lys Cys Asp Gly Leu Tyr Ile Ile Tyr Leu Lys Gly Ser Phe Phe
130                 135                 140
Gln Glu Val Lys Ile Asp Leu His Phe Arg Glu Asp His Asn Pro Ile
145                 150                 155                 160
Ser Ile Pro Met Leu Asn Asp Gly Arg Arg Ile Val Phe Thr Val Val
                165                 170                 175
Ala Ser Leu Ala Phe Lys Asp Lys Val Tyr Leu Thr Val Asn Ala Pro
            180                 185                 190
Asp Thr Leu Cys Glu His Leu Gln Ile Asn Asp Gly Glu Leu Ile Val
            195                 200                 205
Val Gln Leu Thr Pro Gly Tyr Cys Ala Pro Glu Gly Ser Tyr His Ser
    210                 215                 220
Thr Val Asn Gln Val Pro Leu Gly Ser Gly Ala Thr Asn Phe Ser Leu
225                 230                 235                 240
Leu Lys Gln Ala Gly Asp Val Glu Glu Asn Pro Gly Pro Met Glu Phe
                245                 250                 255
Gly Leu Ser Trp Val Phe Leu Val Ala Leu Phe Arg Gly Val Gln Cys
            260                 265                 270
Gly Gly Gly Gly Ser Gln Val Ser His Arg Tyr Pro Arg Gln Leu
        275                 280                 285
Ser Ser Ser Pro Ala Lys Asp Pro Pro Ile Gln Arg Leu Arg Gly Ala
    290                 295                 300
Val Thr Arg Cys Glu Asp Gly Gln Leu Phe Ile Ser Ser Tyr Lys Asn
305                 310                 315                 320
Glu Tyr Gln Thr Met Glu Val Gln Asn Asn Ser Val Val Ile Lys Cys
                325                 330                 335
Asp Gly Leu Tyr Ile Ile Tyr Leu Lys Gly Ser Phe Phe Gln Glu Val
            340                 345                 350
Lys Ile Asp Leu His Phe Arg Glu Asp His Asn Pro Ile Ser Ile Pro
            355                 360                 365
Met Leu Asn Asp Gly Arg Arg Ile Val Phe Thr Val Val Ala Ser Leu
    370                 375                 380
Ala Phe Lys Asp Lys Val Tyr Leu Thr Val Asn Ala Pro Asp Thr Leu
385                 390                 395                 400
Cys Glu His Leu Gln Ile Asn Asp Gly Glu Leu Ile Val Val Gln Leu
                405                 410                 415
Thr Pro Gly Tyr Cys Ala Pro Glu Gly Ser Tyr His Ser Thr Val Asn
            420                 425                 430
Gln Val Pro Leu Gly Ser Gly Ala Thr Asn Phe Ser Leu Leu Lys Gln
    435                 440                 445
```

```
Ala Gly Asp Val Glu Glu Asn Pro Gly Pro Met Glu Phe Gly Leu Ser
    450                 455                 460

Trp Val Phe Leu Val Ala Leu Phe Arg Gly Val Gln Cys Gly Gly Gly
465                 470                 475                 480

Gly Gly Ser Gln Val Ser His Arg Tyr Pro Arg Gln Leu Ser Ser Ser
            485                 490                 495

Pro Ala Lys Asp Pro Pro Ile Gln Arg Leu Arg Gly Ala Val Thr Arg
        500                 505                 510

Cys Glu Asp Gly Gln Leu Phe Ile Ser Ser Tyr Lys Asn Glu Tyr Gln
        515                 520                 525

Thr Met Glu Val Gln Asn Asn Ser Val Val Ile Lys Cys Asp Gly Leu
530                 535                 540

Tyr Ile Ile Tyr Leu Lys Gly Ser Phe Phe Gln Glu Val Lys Ile Asp
545                 550                 555                 560

Leu His Phe Arg Glu Asp His Asn Pro Ile Ser Ile Pro Met Leu Asn
                565                 570                 575

Asp Gly Arg Arg Ile Val Phe Thr Val Val Ala Ser Leu Ala Phe Lys
            580                 585                 590

Asp Lys Val Tyr Leu Thr Val Asn Ala Pro Asp Thr Leu Cys Glu His
            595                 600                 605

Leu Gln Ile Asn Asp Gly Glu Leu Ile Val Val Gln Leu Thr Pro Gly
    610                 615                 620

Tyr Cys Ala Pro Glu Gly Ser Tyr His Ser Thr Val Asn Gln Val Pro
625                 630                 635                 640

Leu Gly Ser Gly Glu Gly Arg Gly Ser Leu Leu Thr Cys Gly Asp Val
                645                 650                 655

Glu Glu Asn Pro Gly Pro Met Val Ser Lys Gly Glu Glu Leu Phe Thr
            660                 665                 670

Gly Val Val Pro Ile Leu Val Glu Leu Asp Gly Asp Val Asn Gly His
            675                 680                 685

Lys Phe Ser Val Ser Gly Glu Gly Glu Gly Asp Ala Thr Tyr Gly Lys
690                 695                 700

Leu Thr Leu Lys Phe Ile Cys Thr Thr Gly Lys Leu Pro Val Pro Trp
705                 710                 715                 720

Pro Thr Leu Val Thr Thr Leu Thr Tyr Gly Val Gln Cys Phe Ser Arg
                725                 730                 735

Tyr Pro Asp His Met Lys Gln His Asp Phe Phe Lys Ser Ala Met Pro
            740                 745                 750

Glu Gly Tyr Val Gln Glu Arg Thr Ile Phe Phe Lys Asp Asp Gly Asn
            755                 760                 765

Tyr Lys Thr Arg Ala Glu Val Lys Phe Glu Gly Asp Thr Leu Val Asn
770                 775                 780

Arg Ile Glu Leu Lys Gly Ile Asp Phe Lys Glu Asp Gly Asn Ile Leu
785                 790                 795                 800

Gly His Lys Leu Glu Tyr Asn Tyr Asn Ser His Asn Val Tyr Ile Met
                805                 810                 815

Ala Asp Lys Gln Lys Asn Gly Ile Lys Val Asn Phe Lys Ile Arg His
            820                 825                 830

Asn Ile Glu Asp Gly Ser Val Gln Leu Ala Asp His Tyr Gln Gln Asn
            835                 840                 845

Thr Pro Ile Gly Asp Gly Pro Val Leu Leu Pro Asp Asn His Tyr Leu
    850                 855                 860

Ser Thr Gln Ser Ala Leu Ser Lys Asp Pro Asn Glu Lys Arg Asp His
```

```
                865                 870                 875                 880
Met Val Leu Leu Glu Phe Val Thr Ala Ala Gly Ile Thr Leu Gly Met
                885                 890                 895
Asp Glu Leu Tyr Lys
        900
```

<210> SEQ ID NO 54
<211> LENGTH: 133
<212> TYPE: PRT
<213> ORGANISM: Homo sapiens

<400> SEQUENCE: 54

```
Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130
```

<210> SEQ ID NO 55
<211> LENGTH: 150
<212> TYPE: PRT
<213> ORGANISM: Mus musculus

<400> SEQUENCE: 55

```
Gln Leu Ser Ser Pro Ala Lys Asp Pro Pro Ile Gln Arg Leu Arg
1               5                   10                  15

Gly Ala Val Thr Arg Cys Glu Asp Gly Gln Leu Phe Ile Ser Ser Tyr
            20                  25                  30

Lys Asn Glu Tyr Gln Thr Met Glu Val Gln Asn Asn Ser Val Val Ile
        35                  40                  45

Lys Cys Asp Gly Leu Tyr Ile Ile Tyr Leu Lys Gly Ser Phe Phe Gln
    50                  55                  60

Glu Val Lys Ile Asp Leu His Phe Arg Glu Asp His Asn Pro Ile Ser
65                  70                  75                  80

Ile Pro Met Leu Asn Asp Gly Arg Arg Ile Val Phe Thr Val Val Ala
                85                  90                  95

Ser Leu Ala Phe Lys Asp Lys Val Tyr Leu Thr Val Asn Ala Pro Asp
            100                 105                 110

Thr Leu Cys Glu His Leu Gln Ile Asn Asp Gly Glu Leu Ile Val Val
        115                 120                 125

Gln Leu Thr Pro Gly Tyr Cys Ala Pro Glu Gly Ser Tyr His Ser Thr
    130                 135                 140

Val Asn Gln Val Pro Leu
```

<210> SEQ ID NO 56
<211> LENGTH: 19
<212> TYPE: PRT
<213> ORGANISM: Artificial Sequence
<220> FEATURE:
<223> OTHER INFORMATION: OX40L signal

<400> SEQUENCE: 56

Met Glu Phe Gly Leu Ser Trp Val Phe Leu Val Ala Leu Phe Arg Gly
1               5                   10                  15

Val Gln Cys

<210> SEQ ID NO 57
<211> LENGTH: 38
<212> TYPE: PRT
<213> ORGANISM: Artificial Sequence
<220> FEATURE:
<223> OTHER INFORMATION: Acid-base zipper for OX40L

<400> SEQUENCE: 57

Thr Thr Ala Pro Ser Ala Gln Leu Glu Lys Glu Leu Gln Ala Leu Glu
1               5                   10                  15

Lys Glu Asn Ala Gln Leu Glu Trp Glu Leu Gln Ala Leu Glu Lys Glu
                20                  25                  30

Leu Ala Gln Ala Ala Ser
        35

<210> SEQ ID NO 58
<211> LENGTH: 22
<212> TYPE: PRT
<213> ORGANISM: Porcine teschovirus-1

<400> SEQUENCE: 58

Gly Ser Gly Ala Thr Asn Phe Ser Leu Leu Lys Gln Ala Gly Asp Val
1               5                   10                  15

Glu Glu Asn Pro Gly Pro
        20

<210> SEQ ID NO 59
<211> LENGTH: 25
<212> TYPE: PRT
<213> ORGANISM: Artificial Sequence
<220> FEATURE:
<223> OTHER INFORMATION: trimeric coiled-coil for OX40L

<400> SEQUENCE: 59

Leu Ile Ala Leu Ala Glu Glu Val Arg Lys Leu Lys Ala Arg Val Asp
1               5                   10                  15

Glu Leu Glu Arg Ile Arg Arg Ser Ile
        20                  25

<210> SEQ ID NO 60
<211> LENGTH: 239
<212> TYPE: PRT
<213> ORGANISM: Human cytomegalovirus

<400> SEQUENCE: 60

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

-continued

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 61
<211> LENGTH: 838
<212> TYPE: PRT
<213> ORGANISM: Artificial Sequence
<220> FEATURE:
<223> OTHER INFORMATION: Human Jagged-1 ("JAG1")

<400> SEQUENCE: 61

Met Asp Met Arg Val Pro Ala Gln Leu Leu Gly Leu Leu Leu Leu Trp
 1               5                  10                  15

Leu Ser Gly Ala Arg Cys Met Arg Ser Pro Arg Thr Arg Gly Arg Ser
             20                  25                  30

Gly Arg Pro Leu Ser Leu Leu Leu Ala Leu Leu Cys Ala Leu Arg Ala
         35                  40                  45

Lys Val Cys Gly Ala Ser Gly Gln Phe Glu Leu Glu Ile Leu Ser Met
 50                  55                  60

Gln Asn Val Asn Gly Glu Leu Gln Asn Gly Asn Cys Cys Gly Gly Ala
65                  70                  75                  80

Arg Asn Pro Gly Asp Arg Lys Cys Thr Arg Asp Glu Cys Asp Thr Tyr
                 85                  90                  95

Phe Lys Val Cys Leu Lys Glu Tyr Gln Ser Arg Val Thr Ala Gly Gly
                100                 105                 110

Pro Cys Ser Phe Gly Ser Gly Ser Thr Pro Val Ile Gly Gly Asn Thr
            115                 120                 125

Phe Asn Leu Lys Ala Ser Arg Gly Asn Asp Arg Asn Arg Ile Val Leu
            130                 135                 140

Pro Phe Ser Phe Ala Trp Pro Arg Ser Tyr Thr Leu Leu Val Glu Ala
145                 150                 155                 160

-continued

```
Trp Asp Ser Ser Asn Asp Thr Val Gln Pro Asp Ser Ile Ile Glu Lys
                165                 170                 175
Ala Ser His Ser Gly Met Ile Asn Pro Ser Arg Gln Trp Gln Thr Leu
            180                 185                 190
Lys Gln Asn Thr Gly Val Ala His Phe Glu Tyr Gln Ile Arg Val Thr
        195                 200                 205
Cys Asp Asp Tyr Tyr Tyr Gly Phe Gly Cys Asn Lys Phe Cys Arg Pro
    210                 215                 220
Arg Asp Asp Phe Phe Gly His Tyr Ala Cys Asp Gln Asn Gly Asn Lys
225                 230                 235                 240
Thr Cys Met Glu Gly Trp Met Gly Pro Glu Cys Asn Arg Ala Ile Cys
                245                 250                 255
Arg Gln Gly Cys Ser Pro Lys His Gly Ser Cys Lys Leu Pro Gly Asp
            260                 265                 270
Cys Arg Cys Gln Tyr Gly Trp Gln Gly Leu Tyr Cys Asp Lys Cys Ile
        275                 280                 285
Pro His Pro Gly Cys Val His Gly Ile Cys Asn Glu Pro Trp Gln Cys
    290                 295                 300
Leu Cys Glu Thr Asn Trp Gly Gly Gln Leu Cys Asp Lys Asp Gly Gly
305                 310                 315                 320
Gly Gly Ser Thr Thr Ala Pro Ser Ala Gln Leu Lys Lys Lys Leu Gln
                325                 330                 335
Ala Leu Lys Lys Lys Lys Asn Ala Gln Leu Lys Trp Lys Leu Gln Ala
            340                 345                 350
Leu Lys Lys Lys Leu Ala Gln Gly Gly Gly Gly Ser Arg Lys Cys
        355                 360                 365
Cys Val Glu Cys Pro Pro Cys Pro Ala Pro Pro Val Ala Gly Pro Ser
    370                 375                 380
Val Phe Leu Phe Pro Pro Lys Pro Lys Asp Thr Leu Met Ile Ser Arg
385                 390                 395                 400
Thr Pro Glu Val Thr Cys Val Val Asp Val Ser His Glu Asp Pro
                405                 410                 415
Glu Val Gln Phe Asn Trp Tyr Val Asp Gly Val Glu Val His Asn Ala
            420                 425                 430
Lys Thr Lys Pro Arg Glu Glu Gln Phe Asn Ser Thr Phe Arg Val Val
        435                 440                 445
Ser Val Leu Thr Val Val His Gln Asp Trp Leu Asn Gly Lys Glu Tyr
    450                 455                 460
Lys Cys Lys Val Ser Asn Lys Gly Leu Pro Ala Pro Ile Glu Lys Thr
465                 470                 475                 480
Ile Ser Lys Thr Lys Gly Gln Pro Arg Glu Pro Gln Val Tyr Thr Leu
                485                 490                 495
Pro Pro Ser Arg Glu Glu Met Thr Lys Asn Gln Val Ser Leu Thr Cys
            500                 505                 510
Leu Val Lys Gly Phe Tyr Pro Ser Asp Ile Ala Val Glu Trp Glu Ser
        515                 520                 525
Asn Gly Gln Pro Glu Asn Asn Tyr Lys Thr Thr Pro Pro Met Leu Asp
    530                 535                 540
Ser Asp Gly Ser Phe Phe Leu Tyr Ser Lys Leu Thr Val Asp Lys Ser
545                 550                 555                 560
Arg Trp Gln Gln Gly Asn Val Phe Ser Cys Ser Val Met His Glu Ala
                565                 570                 575
```

```
Leu His Asn His Tyr Thr Gln Lys Ser Leu Ser Leu Ser Pro Gly Lys
            580                 585                 590

Gly Ser Gly Glu Gly Arg Gly Ser Leu Leu Thr Cys Gly Asp Val Glu
        595                 600                 605

Glu Asn Pro Gly Pro Met Ala Ser Ser Glu Asp Val Ile Lys Glu Phe
    610                 615                 620

Met Arg Phe Lys Val Arg Met Glu Gly Ser Val Asn Gly His Glu Phe
625                 630                 635                 640

Glu Ile Glu Gly Glu Gly Gly Arg Pro Tyr Glu Gly Thr Gln Thr
            645                 650                 655

Ala Lys Leu Lys Val Thr Lys Gly Gly Pro Leu Pro Phe Ala Trp Asp
            660                 665                 670

Ile Leu Ser Pro Gln Phe Gln Tyr Gly Ser Lys Ala Tyr Val Lys His
            675                 680                 685

Pro Ala Asp Ile Pro Asp Tyr Leu Lys Leu Ser Phe Pro Glu Gly Phe
    690                 695                 700

Lys Trp Glu Arg Val Met Asn Phe Glu Asp Gly Gly Val Val Thr Val
705                 710                 715                 720

Thr Gln Asp Ser Ser Leu Gln Asp Gly Glu Phe Ile Tyr Lys Val Lys
                725                 730                 735

Leu Arg Gly Thr Asn Phe Pro Ser Asp Gly Pro Val Met Gln Lys Lys
            740                 745                 750

Thr Met Gly Trp Glu Ala Ser Thr Glu Arg Met Tyr Pro Glu Asp Gly
            755                 760                 765

Ala Leu Lys Gly Glu Ile Lys Met Arg Leu Lys Leu Lys Asp Gly Gly
770                 775                 780

His Tyr Asp Ala Glu Val Lys Thr Thr Tyr Met Ala Lys Lys Pro Val
785                 790                 795                 800

Gln Leu Pro Gly Ala Tyr Lys Thr Asp Ile Lys Leu Asp Ile Thr Ser
                805                 810                 815

His Asn Glu Asp Tyr Thr Ile Val Glu Gln Tyr Glu Arg Ala Glu Gly
            820                 825                 830

Arg His Ser Thr Gly Ala
        835

<210> SEQ ID NO 62
<211> LENGTH: 843
<212> TYPE: PRT
<213> ORGANISM: Artificial Sequence
<220> FEATURE:
<223> OTHER INFORMATION: Mouse Jagged-1 ("JAG1")

<400> SEQUENCE: 62

Met Asp Met Arg Val Pro Ala Gln Leu Leu Gly Leu Leu Leu Leu Trp
1               5                   10                  15

Leu Ser Gly Ala Arg Cys Met Arg Ser Pro Arg Thr Arg Gly Arg Pro
            20                  25                  30

Gly Arg Pro Leu Ser Leu Leu Leu Ala Leu Leu Cys Ala Leu Arg Ala
        35                  40                  45

Lys Val Cys Gly Ala Ser Gly Gln Phe Glu Leu Glu Ile Leu Ser Met
    50                  55                  60

Gln Asn Val Asn Gly Glu Leu Gln Asn Gly Asn Cys Cys Gly Gly Val
65                  70                  75                  80

Arg Asn Pro Gly Asp Arg Lys Cys Thr Arg Asp Glu Cys Asp Thr Tyr
                85                  90                  95
```

```
Phe Lys Val Cys Leu Lys Glu Tyr Gln Ser Arg Val Thr Ala Gly Gly
            100                 105                 110

Pro Cys Ser Phe Gly Ser Gly Ser Thr Pro Val Ile Gly Gly Asn Thr
            115                 120                 125

Phe Asn Leu Lys Ala Ser Arg Gly Asn Asp Arg Asn Arg Ile Val Leu
            130                 135                 140

Pro Phe Ser Phe Ala Trp Pro Arg Ser Tyr Thr Leu Leu Val Glu Ala
145                 150                 155                 160

Trp Asp Ser Ser Asn Asp Thr Ile Gln Pro Asp Ser Ile Ile Glu Lys
            165                 170                 175

Ala Ser His Ser Gly Met Ile Asn Pro Ser Arg Gln Trp Gln Thr Leu
            180                 185                 190

Lys Gln Asn Thr Gly Ile Ala His Phe Glu Tyr Gln Ile Arg Val Thr
            195                 200                 205

Cys Asp Asp His Tyr Tyr Gly Phe Gly Cys Asn Lys Phe Cys Arg Pro
            210                 215                 220

Arg Asp Asp Phe Phe Gly His Tyr Ala Cys Asp Gln Asn Gly Asn Lys
225                 230                 235                 240

Thr Cys Met Glu Gly Trp Met Gly Pro Asp Cys Asn Lys Ala Ile Cys
            245                 250                 255

Arg Gln Gly Cys Ser Pro Lys His Gly Ser Cys Lys Leu Pro Gly Asp
            260                 265                 270

Cys Arg Cys Gln Tyr Gly Trp Gln Gly Leu Tyr Cys Asp Lys Cys Ile
            275                 280                 285

Pro His Pro Gly Cys Val His Gly Thr Cys Asn Glu Pro Trp Gln Cys
            290                 295                 300

Leu Cys Glu Thr Asn Trp Gly Gly Gln Leu Cys Asp Lys Asp Gly Gly
305                 310                 315                 320

Gly Gly Ser Thr Thr Ala Pro Ser Ala Gln Leu Lys Lys Leu Gln
            325                 330                 335

Ala Leu Lys Lys Lys Asn Ala Gln Leu Lys Trp Lys Leu Gln Ala
            340                 345                 350

Leu Lys Lys Lys Leu Ala Gln Gly Gly Gly Gly Ser Gly Asn Ser
            355                 360                 365

Ile Ser Ala Met Val Arg Ser Gly Cys Lys Pro Cys Ile Cys Thr Val
370                 375                 380

Pro Glu Val Ser Ser Val Phe Ile Phe Pro Pro Lys Pro Lys Asp Val
385                 390                 395                 400

Leu Thr Ile Thr Leu Thr Pro Lys Val Thr Cys Val Val Val Asp Ile
            405                 410                 415

Ser Lys Asp Asp Pro Glu Val Gln Phe Ser Trp Phe Val Asp Asp Val
            420                 425                 430

Glu Val His Thr Ala Gln Thr Gln Pro Arg Glu Glu Gln Phe Asn Ser
            435                 440                 445

Thr Phe Arg Ser Val Ser Glu Leu Pro Ile Met His Gln Asp Trp Leu
            450                 455                 460

Asn Gly Lys Glu Phe Lys Cys Arg Val Asn Ser Ala Ala Phe Pro Ala
465                 470                 475                 480

Pro Ile Glu Lys Thr Ile Ser Lys Thr Lys Gly Arg Pro Lys Ala Pro
            485                 490                 495

Gln Val Tyr Thr Ile Pro Pro Pro Lys Glu Gln Met Ala Lys Asp Lys
            500                 505                 510

Val Ser Leu Thr Cys Met Ile Thr Asp Phe Phe Pro Glu Asp Ile Thr
```

```
            515                 520                 525
Val Glu Trp Gln Trp Asn Gly Gln Pro Ala Glu Asn Tyr Lys Asn Thr
530                 535                 540

Gln Pro Ile Met Asp Thr Asp Gly Ser Tyr Phe Val Tyr Ser Lys Leu
545                 550                 555                 560

Asn Val Gln Lys Ser Asn Trp Glu Ala Gly Asn Thr Phe Thr Cys Ser
                565                 570                 575

Val Leu His Glu Gly Leu His Asn His His Thr Glu Lys Ser Leu Ser
            580                 585                 590

His Ser Pro Gly Lys Gly Ser Gly Glu Gly Arg Gly Ser Leu Leu Thr
        595                 600                 605

Cys Gly Asp Val Glu Glu Asn Pro Gly Pro Met Ala Ser Ser Glu Asp
610                 615                 620

Val Ile Lys Glu Phe Met Arg Phe Lys Val Arg Met Glu Gly Ser Val
625                 630                 635                 640

Asn Gly His Glu Phe Glu Ile Glu Gly Glu Gly Glu Gly Arg Pro Tyr
                645                 650                 655

Glu Gly Thr Gln Thr Ala Lys Leu Lys Val Thr Lys Gly Gly Pro Leu
            660                 665                 670

Pro Phe Ala Trp Asp Ile Leu Ser Pro Gln Phe Gln Tyr Gly Ser Lys
        675                 680                 685

Ala Tyr Val Lys His Pro Ala Asp Ile Pro Asp Tyr Leu Lys Leu Ser
    690                 695                 700

Phe Pro Glu Gly Phe Lys Trp Glu Arg Val Met Asn Phe Glu Asp Gly
705                 710                 715                 720

Gly Val Val Thr Val Thr Gln Asp Ser Ser Leu Gln Asp Gly Glu Phe
                725                 730                 735

Ile Tyr Lys Val Lys Leu Arg Gly Thr Asn Phe Pro Ser Asp Gly Pro
            740                 745                 750

Val Met Gln Lys Lys Thr Met Gly Trp Glu Ala Ser Thr Glu Arg Met
        755                 760                 765

Tyr Pro Glu Asp Gly Ala Leu Lys Gly Glu Ile Lys Met Arg Leu Lys
    770                 775                 780

Leu Lys Asp Gly Gly His Tyr Asp Ala Glu Val Lys Thr Thr Tyr Met
785                 790                 795                 800

Ala Lys Lys Pro Val Gln Leu Pro Gly Ala Tyr Lys Thr Asp Ile Lys
                805                 810                 815

Leu Asp Ile Thr Ser His Asn Glu Asp Tyr Thr Ile Val Glu Gln Tyr
            820                 825                 830

Glu Arg Ala Glu Gly Arg His Ser Thr Gly Ala
        835                 840

<210> SEQ ID NO 63
<211> LENGTH: 301
<212> TYPE: PRT
<213> ORGANISM: Homo sapiens

<400> SEQUENCE: 63

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45
```

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
 65                  70                  75                  80

Glu Tyr Gln Ser Arg Val Thr Ala Gly Gly Pro Cys Ser Phe Gly Ser
                 85                  90                  95

Gly Ser Thr Pro Val Ile Gly Gly Asn Thr Phe Asn Leu Lys Ala Ser
             100                 105                 110

Arg Gly Asn Asp Arg Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
            195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
    275                 280                 285

Gly Gly Gln Leu Cys Asp Lys Asp Gly Gly Gly Ser
    290                 295                 300

<210> SEQ ID NO 64
<211> LENGTH: 301
<212> TYPE: PRT
<213> ORGANISM: Mus musculus

<400> SEQUENCE: 64

Met Arg Ser Pro Arg Thr Arg Gly Arg Pro Gly Arg Pro Leu Ser Leu
 1               5                  10                  15

Leu Leu Ala Leu Leu Cys Ala Leu Arg Ala Lys Val Cys Gly Ala Ser
             20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Val Arg Asn Pro Gly Asp Arg
    50                  55                  60

Lys Cys Thr Arg Asp Glu Cys Asp Thr Tyr Phe Lys Val Cys Leu Lys
 65                  70                  75                  80

Glu Tyr Gln Ser Arg Val Thr Ala Gly Gly Pro Cys Ser Phe Gly Ser
                 85                  90                  95

Gly Ser Thr Pro Val Ile Gly Gly Asn Thr Phe Asn Leu Lys Ala Ser
             100                 105                 110

Arg Gly Asn Asp Arg Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
            130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
            195                 200                 205

His Tyr Ala Cys Asp Gln Asn Gly Asn Lys Thr Cys Met Glu Gly Trp
            210                 215                 220

Met Gly Pro Asp Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Thr Cys Asn Glu Pro Trp Gln Cys Leu Cys Glu Thr Asn Trp
            275                 280                 285

Gly Gly Gln Leu Cys Asp Lys Asp Gly Gly Gly Ser
            290                 295                 300

<210> SEQ ID NO 65
<211> LENGTH: 22
<212> TYPE: PRT
<213> ORGANISM: Artificial Sequence
<220> FEATURE:
<223> OTHER INFORMATION: Jagged-1 signal

<400> SEQUENCE: 65

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 66
<211> LENGTH: 36
<212> TYPE: PRT
<213> ORGANISM: Artificial Sequence
<220> FEATURE:
<223> OTHER INFORMATION: Acid-base dimer for Jagged-1

<400> SEQUENCE: 66

Thr Thr Ala Pro Ser Ala Gln Leu Lys Lys Lys Leu Gln Ala Leu Lys
1               5                   10                  15

Lys Lys Lys Asn Ala Gln Leu Lys Trp Lys Leu Gln Ala Leu Lys Lys
            20                  25                  30

Lys Leu Ala Gln
        35

<210> SEQ ID NO 67
<211> LENGTH: 21
<212> TYPE: PRT
<213> ORGANISM: Thosea asigna virus 2A

<400> SEQUENCE: 67

Gly Ser Gly Glu Gly Arg Gly Ser Leu Leu Thr Cys Gly Asp Val Glu
1               5                   10                  15

<210> SEQ ID NO 68
<211> LENGTH: 227
<212> TYPE: PRT
<213> ORGANISM: Artificial Sequence
<220> FEATURE:
<223> OTHER INFORMATION: Human Immunoglobulin G2 Fc ("IgG2Fc") region

<400> SEQUENCE: 68

Arg Lys Cys Cys Val Glu Cys Pro Pro Cys Pro Ala Pro Pro Val Ala
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Gln Phe Asn Trp Tyr Val Asp Gly Val Glu Val
    50                  55                  60

His Asn Ala Lys Thr Lys Pro Arg Glu Glu Gln Phe Asn Ser Thr Phe
65                  70                  75                  80

Arg Val Val Ser Val Leu Thr Val Val His Gln Asp Trp Leu Asn Gly
                85                  90                  95

Lys Glu Tyr Lys Cys Lys Val Ser Asn Lys Gly Leu Pro Ala Pro Ile
            100                 105                 110

Glu Lys Thr Ile Ser Lys Thr Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 69
<211> LENGTH: 232
<212> TYPE: PRT
<213> ORGANISM: Artificial Sequence
<220> FEATURE:
<223> OTHER INFORMATION: Mouse Immunoglobulin G2a Fc ("IgG2aFc") region

<400> SEQUENCE: 69

Gly Asn Ser Ile Ser Ala Met Val Arg Ser Gly Cys Lys Pro Cys Ile
1               5                   10                  15

Cys Thr Val Pro Glu Val Ser Ser Val Phe Ile Phe Pro Pro Lys Pro
            20                  25                  30

Lys Asp Val Leu Thr Ile Thr Leu Thr Pro Lys Val Thr Cys Val Val
        35                  40                  45

Val Asp Ile Ser Lys Asp Asp Pro Glu Val Gln Phe Ser Trp Phe Val

```
            50                  55                  60
Asp Asp Val Glu Val His Thr Ala Gln Thr Gln Pro Arg Glu Glu Gln
 65                  70                  75                  80

Phe Asn Ser Thr Phe Arg Ser Val Ser Glu Leu Pro Ile Met His Gln
                 85                  90                  95

Asp Trp Leu Asn Gly Lys Glu Phe Lys Cys Arg Val Asn Ser Ala Ala
            100                 105                 110

Phe Pro Ala Pro Ile Glu Lys Thr Ile Ser Lys Thr Lys Gly Arg Pro
        115                 120                 125

Lys Ala Pro Gln Val Tyr Thr Ile Pro Pro Lys Glu Gln Met Ala
    130                 135                 140

Lys Asp Lys Val Ser Leu Thr Cys Met Ile Thr Asp Phe Phe Pro Glu
145                 150                 155                 160

Asp Ile Thr Val Glu Trp Gln Trp Asn Gly Gln Pro Ala Glu Asn Tyr
                165                 170                 175

Lys Asn Thr Gln Pro Ile Met Asp Thr Asp Gly Ser Tyr Phe Val Tyr
            180                 185                 190

Ser Lys Leu Asn Val Gln Lys Ser Asn Trp Glu Ala Gly Asn Thr Phe
        195                 200                 205

Thr Cys Ser Val Leu His Glu Gly Leu His Asn His Thr Glu Lys
    210                 215                 220

Ser Leu Ser His Ser Pro Gly Lys
225                 230

<210> SEQ ID NO 70
<211> LENGTH: 225
<212> TYPE: PRT
<213> ORGANISM: Artificial Sequence
<220> FEATURE:
<223> OTHER INFORMATION: Monomer Red Fluorescent Protein ("mRFP")

<400> SEQUENCE: 70

Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
 50                 55                  60

Phe Gln Tyr Gly Ser Lys Ala Tyr Val Lys His Pro Ala Asp Ile Pro
 65                 70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
```

```
                    180                 185                 190
Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
        210                 215                 220

Ala
225
```